(12) United States Patent
Goshima et al.

(10) Patent No.: US 10,836,814 B2
(45) Date of Patent: Nov. 17, 2020

(54) ANTI-SEMAPHORIN 3A ANTIBODY AND TREATMENT OF ALZHEIMER'S DISEASE AND INFLAMMATORY IMMUNE DISEASES USING SAME

(71) Applicants: Yokohama City University, Yokohama (JP); Chiome Bioscience Inc., Tokyo (JP)

(72) Inventors: Yoshio Goshima, Yokohama (JP); Fumio Nakamura, Yokohama (JP); Naoya Yamashita, Yokohama (JP); Hidetaka Seo, Tokyo (JP); Shuichi Hashimoto, Tokyo (JP); Koji Murakami, Tokyo (JP); Naoki Takahashi, Chiba (JP); Yukie Sasakura, Tokyo (JP)

(73) Assignees: YOKOHAMA CITY UNIVERSITY, Kanagawa (JP); CHIOME BEOSCIENCE INC., Tokyo (JP)

( * ) Notice: Subject to any disclaimer, the term of this patent is extended or adjusted under 35 U.S.C. 154(b) by 72 days.

(21) Appl. No.: 15/847,740

(22) Filed: Dec. 19, 2017

(65) Prior Publication Data
US 2018/0208644 A1 Jul. 26, 2018

Related U.S. Application Data

(62) Division of application No. 14/766,062, filed as application No. PCT/JP2014/052758 on Feb. 6, 2014, now Pat. No. 9,879,075.

(30) Foreign Application Priority Data

Feb. 6, 2013 (JP) .................................. 2013-021309

(51) Int. Cl.
C07K 16/18 (2006.01)
A61K 39/00 (2006.01)
A61P 25/28 (2006.01)

(52) U.S. Cl.
CPC ........ C07K 16/18 (2013.01); *A61K 2039/505* (2013.01); *A61P 25/28* (2018.01); *C07K 2317/22* (2013.01); *C07K 2317/24* (2013.01); *C07K 2317/33* (2013.01); *C07K 2317/76* (2013.01); *C07K 2317/92* (2013.01)

(58) Field of Classification Search
CPC .......... A61P 17/06; A61P 37/08; A61P 37/06; A61P 1/16; A61P 7/04; A61P 19/02; A61P 5/14; A61P 25/00; A61P 1/04; A61P 7/06; A61P 37/02; A61P 1/02; A61P 3/10; A61P 37/00; A61P 15/08; A61P 19/08; A61P 27/02; A61P 17/00; A61P 11/00; A61P 29/00; A61P 9/00; G01N 33/566; G01N 33/53; G01N 2500/04; C07K 16/18; C07K 16/2863; C07K 2317/34

See application file for complete search history.

(56) References Cited

U.S. PATENT DOCUMENTS

2003/0032070 A1 2/2003 Good et al.
2012/0251539 A1 10/2012 Ting et al.
2012/0322085 A1 12/2012 Kumanogoh

FOREIGN PATENT DOCUMENTS

| EP | 2497498 A1 | 9/2012 |
| WO | WO 03/007803 A2 | 1/2003 |
| WO | WO 2005/080432 | 9/2005 |
| WO | WO 2011/055550 A1 | 5/2011 |
| WO | WO 2011/066284 A1 | 6/2011 |

OTHER PUBLICATIONS

Rudikoff et al., PNAS, 79:1979-1982, Mar. 1983.*
Rudikoff et al., Proc Natl Acad Sci USA vol. 79, (Year: 1982).*
Vajdos et al., J Mol Biol., 320:415-428, (Year: 2002).*
Lewis et al., Current Murine Models of Sepsis, Surgical Infections 17(4): 385-393, (Year: 2016).*
Asakura. J Intensive Car, 2:20, (Year: 2014).*
Kramer et al., Mutation Research, 752:10-24, (Year: 2013).*
Stepanichev et al., Physiology and Behavior, 80:647-655, (Year: 2004).*
Catalano, Alfonso, et al. "Semaphorin-3A is expressed by tumor cells and alters T-cell signal transduction and function." Blood 107.8 (2006): 3321-3329.
Chakraborty, Goutam et al., "Semaphorin 3A Suppresses Tumor Growth and Metastasis in Mice Melanoma Model" PLoS ONE, Mar. 2012, pp. 1-13, vol. 7, Issue 3, No. e33633.
Chiome Bioscience Inc. (press release), 'Hitoka Ko Sema3A Kotai' Tokkyo Shutsugan no Oshirase, 06 Feb. 6, 2013 http://minkabu.jp/announcements/4583/140120130206081066.pdf.

(Continued)

*Primary Examiner* — Kimberly Ballard
*Assistant Examiner* — Stacey N MacFarlane
(74) *Attorney, Agent, or Firm* — Knobbe Martens Olson & Bear LLP

(57) ABSTRACT

The present invention mainly addresses the problem of providing an antibody against semaphorin 3A protein, said antibody enabling effective prevention and/or treatment of a disease, in which Sema 3A protein participates, such as a neurodegenerative disease, autoimmune disease, inflammatory disease, cancer, infectious disease, etc. or disseminated intravascular coagulation syndrome. An anti-Sema 3A antibody comprising CDRs having specific amino acid sequences (SEQ ID NOS: 1-6, 60-62, 64-66, 68-70, 72-74, 76-78, 80-82, 84-86 and 88-90) enables effective prevention and/or treatment of a disease, in which Sema 3A protein participates, such as a neurodegenerative disease, autoimmune disease, inflammatory disease, cancer, infectious disease, etc. or disseminated intravascular coagulation syndrome and, therefore, remarkably ameliorates symptoms associated with such a disease.

6 Claims, 21 Drawing Sheets

Specification includes a Sequence Listing.

(56) References Cited

OTHER PUBLICATIONS

Chiome Bioscience Inc. (press release), Nanjisei Shikkan Model ni Okeru 'Hitoka Ko Sema3A Kotai' Yakko Shiken Kekka no Oshirase, Dec. 26, 2012 http://contents.x-storage.jp/contents/45830/T/PDF-GENERAL/140120121226054007.pdf.
Chiome Bioscience Inc. (press release), Yokohama City University tono Kyodo Kenkyu Henko Keiyakusho Teiketsu no Oshirase, Apr. 2, 2012 http://minkabu.jp/annoucements/4583/140120120402004082.pdf.
Goodman, C. S., et al. "Unified nomenclature for the semaphorins/collapsins." Cell 97.5 (1999): 551-552.
Goshima, Yoshio et al., "Class 3 semaphorins as a therapeutic target" Expert Opinion, Ther. Targets, 2012, pp. 933-944, vol. 16, No. 9.
Hashimoto-Gotoh, Tamotsu, et al. "An oligodeoxyribonucleotide-directed dual amber method for site-directed mutagenesis." *Gene* 152.2 (1995): 271-275.
International Search Report for PCT/JP2014/052758 dated Apr. 8, 2014.
Jones, Peter T., et al. "Replacing the complementarity-determining regions in a human antibody with those from a mouse." *Nature* 321.6069 (1986): 522-525.
Kabat, E. A., et al. "Sequences of proteins of immunological interest, NIH publication No. 91-3242. US Department of Health and Human Services." Public Health Service, National Institutes of Health, Bethesda, MD (1991).
Kaneko, et al. A selective Sema3A inhibitor enhances regenerative responses and functional recovery of the injured spinal cord. Nature Med. 12: 1380-1389, 2006.
Kolodkin, Alex L., et al. "The semaphorin genes encode a family of transmembrane and secreted growth cone guidance molecules." Cell 75.7 (1993): 1389-1399.
Kramer, Wilfried, and Hans-Joachim Fritz. "[18] Oligonucleotide-directed construction of mutations via gapped duplex DNA." *Methods in enzymology* 154 (1987): 350-367.
Kramer, Wilfried, et al. "The gapped duplex DNA approach to oligonucleotide-directed mutation construction." *Nucleic Acids Research* 12.24 (1984): 9441-9456.
Kunkel, Thomas A. "Rapid and efficient site-specific mutagenesis without phenotypic selection." *Proceedings of the National Academy of Sciences* 82.2 (1985): 488-492.
Lepelletier, Yves et al., "Immunosuppressive role of semaphoring-3A on T cell proliferation is mediated by inhibition of actin cytoskeleton reorganization" European Journal of Immunology, 2006, pp. 1782-1793, vol. 36, No. 7.
Luo, Yuling, David Raible, and Jonathan A. Raper. "Collapsin: a protein in brain that induces the collapse and paralysis of neuronal growth cones." Cell 75.2 (1993): 217-227.

Morrison, Sherie L., et al. "Chimeric human antibody molecules: mouse antigen-binding domains with human constant region domains." *Proceedings of the National Academy of Sciences* 81.21 (1984): 6851-6855.
Müller, Michael W., et al. "Association of axon guidance factor semaphorin 3A with poor outcome in pancreatic cancer." International journal of cancer 121.11 (2007): 2421-2433.
Nasarre, Cecile et al., "Neuropilin-2 acts as a modulator of Sema3A-dependent glioma cell migration" Cell Adhesion & Migration, Oct. 1, 2009, pp. 383-389, vol. 3, No. 4.
Neuberger, Michael S., Gareth T. Williams, and Robert O. Fox. "Recombinant antibodies possessing novel effector functions." *Nature* 312.5995 (1984): 604-608.
OMIM Entry No. 603961 Semaphorin 3A; SEMA3A. Published on Jul. 9, 2014 [online] Retrieved on Jan. 18, 2017. Retrieved from www.omim.org/entry/603961 ?search-SEMA%203A&highlight=3a%20sema.
Riechmann, Lutz, et al. "Reshaping human antibodies for therapy." *Nature* 332.6162 (1988): 323-327.
Sato, Koh, et al. "Reshaping a human antibody to inhibit the interleukin 6-dependent tumor cell growth." *Cancer Research* 53.4 (1993): 851-856.
Shirvan, Anat et al., "Anti-semaphorin 3A antibodies rescue retinal ganglion cells from cell death following optic nerve axotomy" The Journal of Biological Chemistry, Dec. 20, 2002, pp. 49799-49807, vol. 277, No. 51.
Supplementary Partial European Search Report for EP 14749177 dated Jun. 15, 2016.
Takagawa, Shu et al., "Decreased Semaphorin3A expression correlates with disease activity and histological features of rheumatoid arthritis" BMC Musculoskeletal Disorders, 2013, pp. 1-11, vol. 14, No. 40.
Takamatsu, Hyota, et al. "Semaphorins guide the entry of dendritic cells into the lymphatics by activating myosin II." Nature immunology 11.7 (2010): 594-600.
Takeda, Shun-ichi, et al. "Construction of chimaeric processed immunoglobulin genes containing mouse variable and human constant region sequences." *Nature* 314.6010 (1985): 452-454.
Verhoeyen, Martine, Cesar Milstein, and Greg Winter. "Reshaping human antibodies: grafting an antilysozyme activity." *Science* 239.4847 (1988): 1534-1536.
Wen, Haitao et al., "Plexin-A4-semaphorin 3A signaling is required for Toll-like receptor- and sepsis-induced cytokine storm" NEURON, Nov. 2010, vol. 45, No. 4.
Wen, Haitao, et al. "Plexin-A4-semaphorin 3A signaling is required for Toll-like receptor- and sepsis-induced cytokine storm." Journal of Experimental Medicine 207.13 (2010): 2943-2957.
Yamashita, Naoya et al., "Anti-Semaphorin 3A neutralization monoclonal antibody prevents sepsis development in lipopolysaccharide-treated mice" International Immunology, Apr. 7, 2015, pp. 459-466, vol. 27, No. 9.
Zoller, Mark J., and Michael Smith. "Oligonucleotide-directed mutagenesis of DNA fragments cloned into M13 vectors." *Methods in enzymology* 100 (1983): 468-500.

* cited by examiner

Reduction    Non-reduction

1: Humanized antibody (Humanized-1)
2: Humanized antibody (Humanized-2)
3: Avian-human chimeric antibody
4: Avian-mouse chimeric antibody
5: CL18M (+) Avian-mouse chimeric antibody (control)

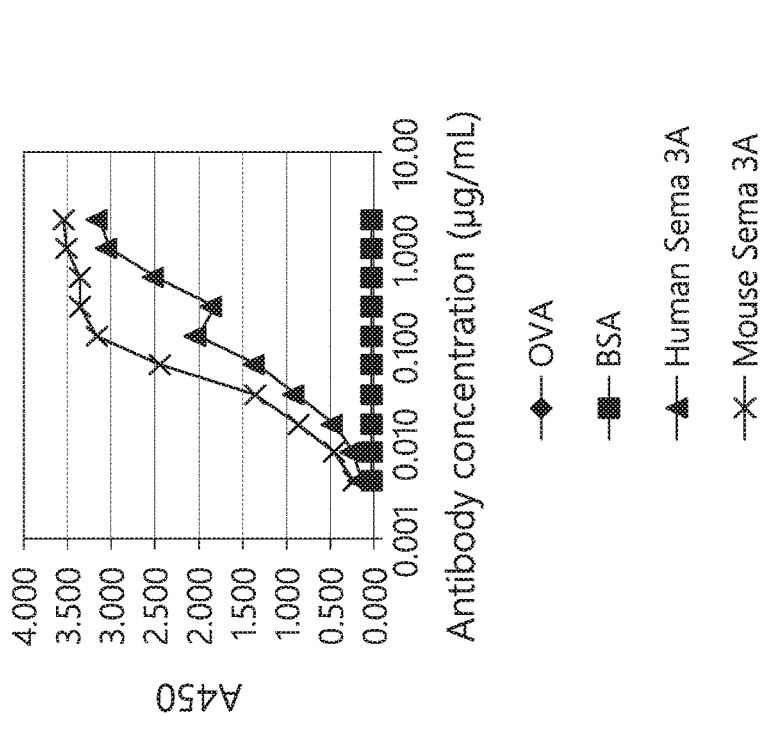
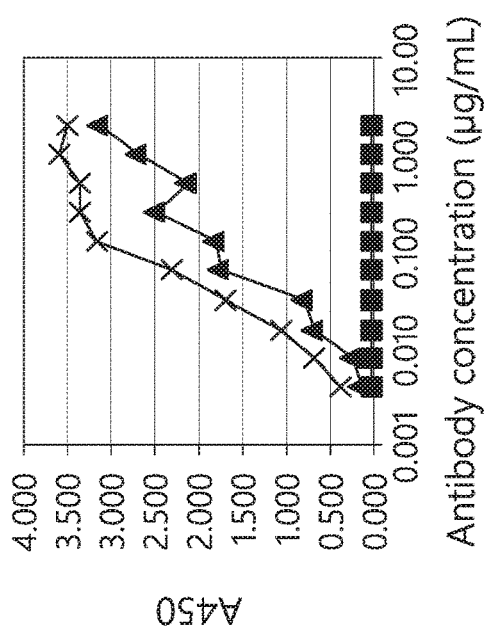
FIG. 4B
FIG. 4A

Wild-type COS-7 cells
Addition of human Sema 3A

NRP1-expressing COS-7 cells
Addition of human Sema 3A

NRP1-expressing COS-7 cells
Addition of human Sema 3A
& Rabbit IgG

NRP1-expressing COS-7 cells
Addition of human Sema 3A &
anti-Sema 3A avian antibody Wild-type COS-7 cells
Addition of human Sema 3A NRP1-expressing COS-7 cells
Addition of human Sema 3A NRP1-expressing COS-7 cells
Addition of human Sema 3A
& Rabbit IgG NRP1-expressing COS-7 cells
Addition of human Sema 3A &
anti-Sema 3A avian-mouse
chimeric antibody Wild-type COS-7 cells
Addition of human Sema 3F NRP1-expressing COS-7 cells
Addition of human Sema 3F NRP1-expressing COS-7 cells
Addition of human Sema 3F &
Rabbit IgG NRP1-expressing COS-7 cells
Addition of human Sema 3F &
anti-Sema 3A avian-mouse
chimeric antibody

SEQUENCE LISTING

```
<160> NUMBER OF SEQ ID NOS: 128

<210> SEQ ID NO 1
<211> LENGTH: 5
<212> TYPE: PRT
<213> ORGANISM: Gallus gallus

<400> SEQUENCE: 1

Ser Tyr Pro Met Gly
1               5

<210> SEQ ID NO 2
<211> LENGTH: 18
<212> TYPE: PRT
<213> ORGANISM: Gallus gallus

<400> SEQUENCE: 2

Gly Ile Asp Asp Asp Gly Asp Ser Asp Thr Arg Tyr Ala Pro Ala Val
1               5                   10                  15

Lys Gly

<210> SEQ ID NO 3
<211> LENGTH: 14
<212> TYPE: PRT
<213> ORGANISM: Gallus gallus

<400> SEQUENCE: 3

His Thr Gly Ile Gly Ala Asn Ser Ala Gly Ser Ile Asp Ala
1               5                   10

<210> SEQ ID NO 4
<211> LENGTH: 13
<212> TYPE: PRT
<213> ORGANISM: Gallus gallus

<400> SEQUENCE: 4

Ser Gly Gly Gly Ser Tyr Thr Gly Ser Tyr Tyr Tyr Gly
1               5                   10

<210> SEQ ID NO 5
<211> LENGTH: 7
<212> TYPE: PRT
<213> ORGANISM: Gallus gallus

<400> SEQUENCE: 5

Tyr Asn Asn Lys Arg Pro Ser
1               5

<210> SEQ ID NO 6
<211> LENGTH: 9
<212> TYPE: PRT
<213> ORGANISM: Gallus gallus

<400> SEQUENCE: 6

Gly Ser Ala Asp Asn Ser Gly Asp Ala
1               5
```

```
<210> SEQ ID NO 7
<211> LENGTH: 124
<212> TYPE: PRT
<213> ORGANISM: Artificial
<220> FEATURE:
<223> OTHER INFORMATION: Heavy chain variable region of chicken-human
      chimera antibody

<400> SEQUENCE: 7

Ala Val Thr Leu Asp Glu Ser Gly Gly Leu Gln Thr Pro Gly Gly
1               5                   10                  15

Ala Leu Ser Leu Val Cys Lys Ala Ser Gly Phe Thr Phe Ser Ser Tyr
            20                  25                  30

Pro Met Gly Trp Val Arg Gln Ala Pro Gly Lys Gly Leu Glu Trp Val
        35                  40                  45

Ala Gly Ile Asp Asp Asp Gly Asp Ser Asp Thr Arg Tyr Ala Pro Ala
    50                  55                  60

Val Lys Gly Arg Ala Thr Ile Ser Arg Asp Asn Gly Gln Ser Thr Val
65                  70                  75                  80

Arg Leu Gln Leu Asn Asn Leu Arg Ala Glu Asp Thr Gly Thr Tyr Tyr
                85                  90                  95

Cys Ala Lys His Thr Gly Ile Gly Ala Asn Ser Ala Gly Ser Ile Asp
            100                 105                 110

Ala Trp Gly His Gly Thr Glu Val Ile Val Ser Ser
        115                 120

<210> SEQ ID NO 8
<211> LENGTH: 124
<212> TYPE: PRT
<213> ORGANISM: Artificial
<220> FEATURE:
<223> OTHER INFORMATION: Heavy chain variable region of chicken-human
      chimera antibody

<400> SEQUENCE: 8

Ala Val Thr Leu Asp Glu Ser Gly Gly Leu Gln Thr Pro Gly Gly
1               5                   10                  15

Ala Leu Ser Leu Val Cys Lys Ala Ser Gly Phe Thr Phe Ser Ser Tyr
            20                  25                  30

Pro Met Gly Trp Val Arg Gln Ala Pro Gly Lys Gly Leu Glu Trp Val
        35                  40                  45

Ala Gly Ile Asp Asp Asp Gly Asp Ser Asp Thr Arg Tyr Ala Pro Ala
    50                  55                  60

Val Lys Gly Arg Ala Thr Ile Ser Arg Asp Asn Gly Gln Ser Thr Val
65                  70                  75                  80

Arg Leu Gln Leu Asn Asn Leu Arg Ala Glu Asp Thr Gly Thr Tyr Tyr
                85                  90                  95

Cys Ala Lys His Thr Gly Ile Gly Ala Asn Ser Ala Gly Ser Ile Asp
            100                 105                 110

Ala Trp Gly His Gly Thr Glu Val Ile Val Ser Ser
        115                 120

<210> SEQ ID NO 9
<211> LENGTH: 107
<212> TYPE: PRT
<213> ORGANISM: Artificial
<220> FEATURE:
<223> OTHER INFORMATION: Light chain variable region of chicken-human
      chimera antibody
```

<400> SEQUENCE: 9

Ala Leu Thr Gln Pro Ala Ser Val Ser Ala Asn Leu Gly Gly Thr Val
1               5                   10                  15

Lys Ile Thr Cys Ser Gly Gly Ser Tyr Thr Gly Ser Tyr Tyr Tyr
            20                  25                  30

Gly Trp Tyr Gln Gln Lys Ser Pro Gly Ser Ala Leu Val Thr Met Ile
        35                  40                  45

Tyr Tyr Asn Asn Lys Arg Pro Ser Asp Ile Pro Ser Arg Phe Ser Gly
    50                  55                  60

Ser Leu Ser Gly Ser Thr Asn Thr Leu Thr Ile Thr Gly Val Arg Ala
65                  70                  75                  80

Asp Asp Glu Ala Val Tyr Phe Cys Gly Ser Ala Asp Asn Ser Gly Asp
                85                  90                  95

Ala Phe Gly Ala Gly Thr Thr Leu Thr Val Leu
                100                 105

<210> SEQ ID NO 10
<211> LENGTH: 107
<212> TYPE: PRT
<213> ORGANISM: Artificial
<220> FEATURE:
<223> OTHER INFORMATION: Light chain variable region of chicken-human
      chimera antibody

<400> SEQUENCE: 10

Ala Leu Thr Gln Pro Ala Ser Val Ser Ala Asn Leu Gly Gly Thr Val
1               5                   10                  15

Lys Ile Thr Cys Ser Gly Gly Ser Tyr Thr Gly Ser Tyr Tyr Tyr
            20                  25                  30

Gly Trp Tyr Gln Gln Lys Ser Pro Gly Ser Ala Leu Val Thr Met Ile
        35                  40                  45

Tyr Tyr Asn Asn Lys Arg Pro Ser Asp Ile Pro Ser Arg Phe Ser Gly
    50                  55                  60

Ser Leu Ser Gly Ser Thr Asn Thr Leu Thr Ile Thr Gly Val Arg Ala
65                  70                  75                  80

Asp Asp Glu Ala Val Tyr Phe Cys Gly Ser Ala Asp Asn Ser Gly Asp
                85                  90                  95

Ala Phe Gly Ala Gly Thr Thr Leu Thr Val Leu
                100                 105

<210> SEQ ID NO 11
<211> LENGTH: 124
<212> TYPE: PRT
<213> ORGANISM: Artificial
<220> FEATURE:
<223> OTHER INFORMATION: Heavy chain variable region of humanized
      antibody

<400> SEQUENCE: 11

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Gly Trp Val Arg Gln Ala Pro Gly Lys Gly Leu Glu Trp Val
        35                  40                  45

Ala Gly Ile Asp Asp Asp Gly Asp Ser Asp Thr Arg Tyr Ala Pro Ala
    50                  55                  60

```
Val Lys Gly Arg Ala Thr Ile Ser Arg Asp Asn Ser Lys Asn Thr Val
 65                  70                  75                  80

Tyr Leu Gln Met Asn Ser Leu Arg Ala Glu Asp Thr Ala Val Tyr Tyr
                 85                  90                  95

Cys Ala Lys His Thr Gly Ile Gly Ala Asn Ser Ala Gly Ser Ile Asp
                100                 105                 110

Ala Trp Gly Gln Gly Thr Leu Val Thr Val Ser Ser
            115                 120

<210> SEQ ID NO 12
<211> LENGTH: 108
<212> TYPE: PRT
<213> ORGANISM: Artificial
<220> FEATURE:
<223> OTHER INFORMATION: Light chain variable region of humanized
      antibody Humanized-1

<400> SEQUENCE: 12

Ser Tyr Glu Leu Thr Gln Pro Pro Ser Val Ser Val Ser Pro Gly Gln
  1               5                  10                  15

Thr Ala Arg Ile Thr Cys Ser Gly Gly Ser Tyr Thr Gly Ser Tyr
                 20                  25                  30

Tyr Tyr Gly Trp Tyr Gln Gln Lys Pro Gly Gln Ala Pro Val Thr Met
                 35                  40                  45

Ile Tyr Tyr Asn Asn Lys Arg Pro Ser Asp Ile Pro Glu Arg Phe Ser
 50                  55                  60

Gly Ser Leu Ser Gly Thr Thr Asn Thr Leu Thr Ile Ser Gly Val Gln
 65                  70                  75                  80

Ala Glu Asp Glu Ala Asp Tyr Tyr Cys Gly Ser Ala Asp Asn Ser Gly
                 85                  90                  95

Asp Ala Phe Gly Thr Gly Thr Lys Val Thr Val Leu
                100                 105

<210> SEQ ID NO 13
<211> LENGTH: 108
<212> TYPE: PRT
<213> ORGANISM: Artificial
<220> FEATURE:
<223> OTHER INFORMATION: Light chain variable region of humanized
      antibody Humanized-2

<400> SEQUENCE: 13

Ser Tyr Glu Leu Thr Gln Pro Pro Ser Val Ser Val Ser Pro Gly Gln
  1               5                  10                  15

Thr Ala Arg Ile Thr Cys Ser Gly Gly Gly Ser Tyr Thr Gly Ser Tyr
                 20                  25                  30

Tyr Tyr Gly Trp Tyr Gln Gln Lys Pro Gly Gln Ala Pro Val Thr Val
                 35                  40                  45

Ile Tyr Tyr Asn Asn Lys Arg Pro Ser Asp Ile Pro Glu Arg Phe Ser
 50                  55                  60

Gly Ser Leu Ser Gly Thr Thr Asn Thr Leu Thr Ile Ser Gly Val Gln
 65                  70                  75                  80

Ala Glu Asp Glu Ala Asp Tyr Tyr Cys Gly Ser Ala Asp Asn Ser Gly
                 85                  90                  95

Asp Ala Phe Gly Thr Gly Thr Lys Val Thr Val Leu
                100                 105

<210> SEQ ID NO 14
<211> LENGTH: 372
```

```
<212> TYPE: DNA
<213> ORGANISM: Artificial
<220> FEATURE:
<223> OTHER INFORMATION: Base sequence coding amino acid sequence of
      heavy chain variable region of chicken-human chimera antibody

<400> SEQUENCE: 14
gccgtgacgt tggacgagtc cggggcggc ctccagacgc ccggggagc gctcagcctc      60 gtctgcaagg cctccgggtt caccttcagc agttatccca tgggttgggt gcgacaggcg    120
cccggcaagg gctggagtg gtcgctggt attgatgatg atggtgatag tgacacaaga      180
tacgcgccgg cggtgaaggg ccgtgccacc atctcgaggg acaacgggca gagcacagtg    240
aggctgcagc tgaacaacct cagggctgag gacaccggca cctactactg cgccaaacat    300
actggtattg gtgctaatag tgctggtagc atcgacgcat ggggccacgg gaccgaagtc    360
atcgtctcct cc                                                         372

<210> SEQ ID NO 15
<211> LENGTH: 372
<212> TYPE: DNA
<213> ORGANISM: Artificial
<220> FEATURE:
<223> OTHER INFORMATION: Base sequence coding amino acid sequence of
      heavy chain variable region of chicken-human chimera antibody

<400> SEQUENCE: 15
gccgtgacgt tggacgagtc cggggcggc ctccagacgc ccggggagc gctcagcctc      60 gtctgcaagg cctccgggtt caccttcagc agttatccca tgggttgggt gcgacaggcg    120
cccggcaagg gctggagtg gtcgctggt attgatgatg atggtgatag tgacacaaga      180
tacgcgccgg cggtgaaggg ccgtgccacc atctcgaggg acaacgggca gagcacagtg    240
aggctgcagc tgaacaacct cagggctgag gacaccggca cctactactg cgccaaacat    300
actggtattg gtgctaatag tgctggtagc atcgacgcat ggggccacgg gaccgaagtc    360
atcgtctcct cc                                                         372

<210> SEQ ID NO 16
<211> LENGTH: 321
<212> TYPE: DNA
<213> ORGANISM: Artificial
<220> FEATURE:
<223> OTHER INFORMATION: Base sequence coding amino acid sequence of
      light chain variable region of chicken-human chimera antibody

<400> SEQUENCE: 16
gcgctgactc agccggcctc ggtgtcagca aacctgggag gaaccgtcaa gatcacctgc     60
tccgggggtg gcagctatac tggaagttac tattatggct ggtaccagca gaagtctcct    120
ggcagtgccc ttgtcactat gatctattac aacaacaaga ccctcggaa catcccttca     180 cgattctccg gttccctatc cggctccaca aacacattaa ccatcactgg ggtccgagcc    240
gatgacgagg ctgtctatt ctgtgggagt gcagacaaca gtggtgatgc atttggggcc    300
gggacaaccc tgaccgtcct a                                               321

<210> SEQ ID NO 17
<211> LENGTH: 321
<212> TYPE: DNA
<213> ORGANISM: Artificial
<220> FEATURE:
<223> OTHER INFORMATION: Base sequence coding amino acid sequence of
      light chain variable region of chicken-human chimera antibody
```

```
<400> SEQUENCE: 17
gcgctgactc agccggcctc ggtgtcagca aacctgggag gaaccgtcaa gatcacctgc      60
tccgggggtg gcagctatac tggaagttac tattatggct ggtaccagca gaagtctcct     120
ggcagtgccc ttgtcactat gatctattac aacaacaaga gaccctcgga catcccttca     180
cgattctccg gttccctatc cggctccaca aacacattaa ccatcactgg ggtccgagcc     240
gatgacgagg ctgtctattt ctgtgggagt gcagacaaca gtggtgatgc atttggggcc     300
gggacaaccc tgaccgtcct a                                               321

<210> SEQ ID NO 18
<211> LENGTH: 15
<212> TYPE: DNA
<213> ORGANISM: Gallus gallus

<400> SEQUENCE: 18
agttatccca tgggt                                                       15

<210> SEQ ID NO 19
<211> LENGTH: 54
<212> TYPE: DNA
<213> ORGANISM: Gallus gallus

<400> SEQUENCE: 19
ggtattgatg atgatggtga tagtgacaca agatacgcgc cggcggtgaa gggc            54

<210> SEQ ID NO 20
<211> LENGTH: 42
<212> TYPE: DNA
<213> ORGANISM: Gallus gallus

<400> SEQUENCE: 20
catactggta ttggtgctaa tagtgctggt agcatcgacg ca                         42

<210> SEQ ID NO 21
<211> LENGTH: 39
<212> TYPE: DNA
<213> ORGANISM: Gallus gallus

<400> SEQUENCE: 21
tccgggggtg gcagctatac tggaagttac tattatggc                             39

<210> SEQ ID NO 22
<211> LENGTH: 21
<212> TYPE: DNA
<213> ORGANISM: Gallus gallus

<400> SEQUENCE: 22
tacaacaaca agagaccctc g                                                21

<210> SEQ ID NO 23
<211> LENGTH: 27
<212> TYPE: DNA
<213> ORGANISM: Gallus gallus

<400> SEQUENCE: 23
gggagtgcag acaacagtgg tgatgca                                          27

<210> SEQ ID NO 24
<211> LENGTH: 372
<212> TYPE: DNA
<213> ORGANISM: Artificial
```

<220> FEATURE:
<223> OTHER INFORMATION: Base sequence coding amino acid sequence of
     heavy chain variable region of humanized antibody

<400> SEQUENCE: 24

| | | |
|---|---|---|
| gaagtgcagc tgctggagag cgggggggga ctggtgcagc ccggcgggag tctgagactg | 60 |
| tcatgcgccg ctagcgggtt cacttttagc tcctacccaa tgggatgggt caggcaggca | 120 |
| cctggcaagg gactggagtg ggtggctggc atcgacgatg acggggattc tgacacccga | 180 |
| tacgctcctg cagtgaaggg acgagccacc atttccagag ataactctaa aaatacagtc | 240 |
| tatctgcaga tgaacagcct gcgagctgaa gacactgcag tgtactattg cgccaagcac | 300 |
| accggaatcg gcgccaattc tgctggcagt attgatgctt ggggcaggg aaccctggtc | 360 |
| acagtgtcta gt | 372 |

<210> SEQ ID NO 25
<211> LENGTH: 324
<212> TYPE: DNA
<213> ORGANISM: Artificial
<220> FEATURE:
<223> OTHER INFORMATION: Base sequence coding amino acid sequence of
     light chain variable region of humanized antibody Humanized-1

<400> SEQUENCE: 25

| | | |
|---|---|---|
| tcatacgaac tgacccagcc ccctagcgtc tccgtgtctc ccgggcagac tgcaaggatc | 60 |
| acctgcagcg gaggaggatc ctataccggg tcttactatt acggatggta ccagcagaag | 120 |
| ccaggacagg ctcccgtgac aatgatctat acaacaaca gcggccttc tgacattcca | 180 |
| gagcggttca gcggatcact gagcggcacc acaaacactc tgaccattag cggggtgcag | 240 |
| gccgaggacg aagctgatta ttactgcggc agtgcagaca tagcgggga tgccttcggc | 300 |
| acagggacta aagtgactgt cctg | 324 |

<210> SEQ ID NO 26
<211> LENGTH: 324
<212> TYPE: DNA
<213> ORGANISM: Artificial
<220> FEATURE:
<223> OTHER INFORMATION: Base sequence coding amino acid sequence of
     light chain variable region of humanized antibody Humanized-2

<400> SEQUENCE: 26

| | | |
|---|---|---|
| tcatacgaac tgacccagcc ccctagcgtc tccgtgtctc ccgggcagac tgcaaggatc | 60 |
| acctgcagcg gaggaggatc ctataccggg tcttactatt acggatggta ccagcagaag | 120 |
| ccaggacagg ctcccgtgac agtgatctat acaacaaca gcggccttc tgacattcca | 180 |
| gagcggttca gcggatcact gagcggcacc acaaacactc tgaccattag cggggtgcag | 240 |
| gccgaggacg aagctgatta ttactgcggc agtgcagaca tagcggggga tgccttcggc | 300 |
| acagggacta aagtgactgt cctg | 324 |

<210> SEQ ID NO 27
<211> LENGTH: 40
<212> TYPE: DNA
<213> ORGANISM: Artificial
<220> FEATURE:
<223> OTHER INFORMATION: Primer1

<400> SEQUENCE: 27

| | | |
|---|---|---|
| gaagatctaa gcttgccatg gcctgggctc ctctcctcct | 40 |

```
<210> SEQ ID NO 28
<211> LENGTH: 27
<212> TYPE: DNA
<213> ORGANISM: Artificial
<220> FEATURE:
<223> OTHER INFORMATION: Primer2

<400> SEQUENCE: 28
tggcgaagac ttcggctggc ctaggac                                          27

<210> SEQ ID NO 29
<211> LENGTH: 30
<212> TYPE: DNA
<213> ORGANISM: Artificial
<220> FEATURE:
<223> OTHER INFORMATION: Primer3

<400> SEQUENCE: 29
gaagatctaa gcttaccatg agcccactcg                                       30

<210> SEQ ID NO 30
<211> LENGTH: 39
<212> TYPE: DNA
<213> ORGANISM: Artificial
<220> FEATURE:
<223> OTHER INFORMATION: Primer4

<400> SEQUENCE: 30
cgatggggct gttgttttgg cggaggagac gatgacttc                             39

<210> SEQ ID NO 31
<211> LENGTH: 30
<212> TYPE: DNA
<213> ORGANISM: Artificial
<220> FEATURE:
<223> OTHER INFORMATION: Primer5

<400> SEQUENCE: 31
aagtcttcgc catcagtcac cctgtttcca                                       30

<210> SEQ ID NO 32
<211> LENGTH: 27
<212> TYPE: DNA
<213> ORGANISM: Artificial
<220> FEATURE:
<223> OTHER INFORMATION: Primer6

<400> SEQUENCE: 32
tatgcggccg cttactagga acagtca                                          27

<210> SEQ ID NO 33
<211> LENGTH: 39
<212> TYPE: DNA
<213> ORGANISM: Artificial
<220> FEATURE:
<223> OTHER INFORMATION: Primer7

<400> SEQUENCE: 33
gccaaaacaa cagccccatc ggtctatcca ctggcccct                             39

<210> SEQ ID NO 34
<211> LENGTH: 28
<212> TYPE: DNA
<213> ORGANISM: Artificial
<220> FEATURE:
<223> OTHER INFORMATION: Primer8
```

<400> SEQUENCE: 34
agatagcggc cgcttatcat ttacccgg                28

<210> SEQ ID NO 35
<211> LENGTH: 454
<212> TYPE: PRT
<213> ORGANISM: Artificial
<220> FEATURE:
<223> OTHER INFORMATION: Heavy chain of chicken-mouse chimera antibody

<400> SEQUENCE: 35

```
Ala Val Thr Leu Asp Glu Ser Gly Gly Leu Gln Thr Pro Gly Gly
1               5                   10                  15

Ala Leu Ser Leu Val Cys Lys Ala Ser Gly Phe Thr Phe Ser Ser Tyr
            20                  25                  30

Pro Met Gly Trp Val Arg Gln Ala Pro Gly Lys Gly Leu Glu Trp Val
        35                  40                  45

Ala Gly Ile Asp Asp Asp Gly Asp Ser Asp Thr Arg Tyr Ala Pro Ala
    50                  55                  60

Val Lys Gly Arg Ala Thr Ile Ser Arg Asp Asn Gly Gln Ser Thr Val
65                  70                  75                  80

Arg Leu Gln Leu Asn Asn Leu Arg Ala Glu Asp Thr Gly Thr Tyr Tyr
                85                  90                  95

Cys Ala Lys His Thr Gly Ile Gly Ala Asn Ser Ala Gly Ser Ile Asp
            100                 105                 110

Ala Trp Gly His Gly Thr Glu Val Ile Val Ser Ser Ala Lys Thr Thr
        115                 120                 125

Ala Pro Ser Val Tyr Pro Leu Ala Pro Val Cys Gly Asp Thr Thr Gly
    130                 135                 140

Ser Ser Val Thr Leu Gly Cys Leu Val Lys Gly Tyr Phe Pro Glu Pro
145                 150                 155                 160

Val Thr Leu Thr Trp Asn Ser Gly Ser Leu Ser Ser Gly Val His Thr
                165                 170                 175

Phe Pro Ala Val Leu Gln Ser Asp Leu Tyr Thr Leu Ser Ser Ser Val
            180                 185                 190

Thr Val Thr Ser Ser Thr Trp Pro Ser Gln Ser Ile Thr Cys Asn Val
        195                 200                 205

Ala His Pro Ala Ser Ser Thr Lys Val Asp Lys Lys Ile Glu Pro Arg
    210                 215                 220

Gly Pro Thr Ile Lys Pro Cys Pro Pro Cys Lys Cys Pro Ala Pro Asn
225                 230                 235                 240

Leu Leu Gly Gly Pro Ser Val Phe Ile Phe Pro Pro Lys Ile Lys Asp
                245                 250                 255

Val Leu Met Ile Ser Leu Ser Pro Ile Val Thr Cys Val Val Val Asp
            260                 265                 270

Val Ser Glu Asp Asp Pro Asp Val Gln Ile Ser Trp Phe Val Asn Asn
        275                 280                 285

Val Glu Val His Thr Ala Gln Thr Gln Thr His Arg Glu Asp Tyr Asn
    290                 295                 300

Ser Thr Leu Arg Val Val Ser Ala Leu Pro Ile Gln His Gln Asp Trp
305                 310                 315                 320

Met Ser Gly Lys Glu Phe Lys Cys Lys Val Asn Asn Lys Asp Leu Pro
                325                 330                 335

Ala Pro Ile Glu Arg Thr Ile Ser Lys Pro Lys Gly Ser Val Arg Ala
            340                 345                 350
```

```
Pro Gln Val Tyr Val Leu Pro Pro Glu Glu Met Thr Lys Lys
        355                 360                 365

Gln Val Thr Leu Thr Cys Met Val Thr Asp Phe Met Pro Glu Asp Ile
370                 375                 380

Tyr Val Glu Trp Thr Asn Asn Gly Lys Thr Glu Leu Asn Tyr Lys Asn
385                 390                 395                 400

Thr Glu Pro Val Leu Asp Ser Asp Gly Ser Tyr Phe Met Tyr Ser Lys
                405                 410                 415

Leu Arg Val Glu Lys Lys Asn Trp Val Glu Arg Asn Ser Tyr Ser Cys
                420                 425                 430

Ser Val Val His Glu Gly Leu His Asn His His Thr Thr Lys Ser Phe
                435                 440                 445

Ser Arg Thr Pro Gly Lys
        450

<210> SEQ ID NO 36
<211> LENGTH: 213
<212> TYPE: PRT
<213> ORGANISM: Artificial
<220> FEATURE:
<223> OTHER INFORMATION: Light chain of chicken-mouse chimera antibody

<400> SEQUENCE: 36

Ala Leu Thr Gln Pro Ala Ser Val Ser Ala Asn Leu Gly Gly Thr Val
1               5                   10                  15

Lys Ile Thr Cys Ser Gly Gly Gly Ser Tyr Thr Gly Ser Tyr Tyr Tyr
                20                  25                  30

Gly Trp Tyr Gln Gln Lys Ser Pro Gly Ser Ala Leu Val Thr Met Ile
            35                  40                  45

Tyr Tyr Asn Asn Lys Arg Pro Ser Asp Ile Pro Ser Arg Phe Ser Gly
50                  55                  60

Ser Leu Ser Gly Ser Thr Asn Thr Leu Thr Ile Thr Gly Val Arg Ala
65                  70                  75                  80

Asp Asp Glu Ala Val Tyr Phe Cys Gly Ser Ala Asp Asn Ser Gly Asp
                85                  90                  95

Ala Phe Gly Ala Gly Thr Thr Leu Thr Val Leu Gly Gln Pro Lys Ser
            100                 105                 110

Ser Pro Ser Val Thr Leu Phe Pro Pro Ser Ser Glu Glu Leu Glu Thr
        115                 120                 125

Asn Lys Ala Thr Leu Val Cys Thr Ile Thr Asp Phe Tyr Pro Gly Val
130                 135                 140

Val Thr Val Asp Trp Lys Val Asp Gly Thr Pro Val Thr Gln Gly Met
145                 150                 155                 160

Glu Thr Thr Gln Pro Ser Lys Gln Ser Asn Asn Lys Tyr Met Ala Ser
                165                 170                 175

Ser Tyr Leu Thr Leu Thr Ala Arg Ala Trp Glu Arg His Ser Ser Tyr
            180                 185                 190

Ser Cys Gln Val Thr His Glu Gly His Thr Val Glu Lys Ser Leu Ser
        195                 200                 205

Arg Ala Asp Cys Ser
        210

<210> SEQ ID NO 37
<211> LENGTH: 26
<212> TYPE: DNA
<213> ORGANISM: Artificial
```

```
<220> FEATURE:
<223> OTHER INFORMATION: Primer A gamma

<400> SEQUENCE: 37
gaagatctaa gcttccacca tggcat                                        26

<210> SEQ ID NO 38
<211> LENGTH: 24
<212> TYPE: DNA
<213> ORGANISM: Artificial
<220> FEATURE:
<223> OTHER INFORMATION: Primer B gamma

<400> SEQUENCE: 38
ttgtaataga tcactgtcac ggga                                          24

<210> SEQ ID NO 39
<211> LENGTH: 24
<212> TYPE: DNA
<213> ORGANISM: Artificial
<220> FEATURE:
<223> OTHER INFORMATION: Primer C gamma

<400> SEQUENCE: 39
tcccgtgaca gtgatctatt acaa                                          24

<210> SEQ ID NO 40
<211> LENGTH: 25
<212> TYPE: DNA
<213> ORGANISM: Artificial
<220> FEATURE:
<223> OTHER INFORMATION: Primer D gamma

<400> SEQUENCE: 40
agatagcggc cgcttaggaa cattc                                         25

<210> SEQ ID NO 41
<211> LENGTH: 36
<212> TYPE: DNA
<213> ORGANISM: Artificial
<220> FEATURE:
<223> OTHER INFORMATION: Primer E gamma

<400> SEQUENCE: 41
gaagatctaa gcttccacca tggcctgggc tcctct                             36

<210> SEQ ID NO 42
<211> LENGTH: 31
<212> TYPE: DNA
<213> ORGANISM: Artificial
<220> FEATURE:
<223> OTHER INFORMATION: Primer F gamma

<400> SEQUENCE: 42
ctttgggctg gcctaggacg gtcagggttg t                                  31

<210> SEQ ID NO 43
<211> LENGTH: 32
<212> TYPE: DNA
<213> ORGANISM: Artificial
<220> FEATURE:
<223> OTHER INFORMATION: Primer G gamma

<400> SEQUENCE: 43
gaagatctaa gcttccacca tgagcccact cg                                 32
```

<210> SEQ ID NO 44
<211> LENGTH: 34
<212> TYPE: DNA
<213> ORGANISM: Artificial
<220> FEATURE:
<223> OTHER INFORMATION: Primer H gamma

<400> SEQUENCE: 44
gcccctttgt actagcggag gagacgatga cttc                              34

<210> SEQ ID NO 45
<211> LENGTH: 27
<212> TYPE: DNA
<213> ORGANISM: Artificial
<220> FEATURE:
<223> OTHER INFORMATION: Primer I gamma

<400> SEQUENCE: 45
ggccagccca aagccaaccc taccgtg                                      27

<210> SEQ ID NO 46
<211> LENGTH: 32
<212> TYPE: DNA
<213> ORGANISM: Artificial
<220> FEATURE:
<223> OTHER INFORMATION: Primer J gamma

<400> SEQUENCE: 46
agatagcggc cgcttattag gaacattcgg tt                                32

<210> SEQ ID NO 47
<211> LENGTH: 33
<212> TYPE: DNA
<213> ORGANISM: Artificial
<220> FEATURE:
<223> OTHER INFORMATION: Primer K gamma

<400> SEQUENCE: 47
gctagtacaa aggggccctc agtgttccca ctg                               33

<210> SEQ ID NO 48
<211> LENGTH: 34
<212> TYPE: DNA
<213> ORGANISM: Artificial
<220> FEATURE:
<223> OTHER INFORMATION: Primer L gamma

<400> SEQUENCE: 48
agatagcggc cgcttattat tttccaggtg acag                              34

<210> SEQ ID NO 49
<211> LENGTH: 473
<212> TYPE: PRT
<213> ORGANISM: Artificial
<220> FEATURE:
<223> OTHER INFORMATION: Heavy chain of humanized antibody

<400> SEQUENCE: 49

Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

```
Ser Ser Tyr Pro Met Gly Trp Val Arg Gln Ala Pro Gly Lys Gly Leu
    50              55                  60

Glu Trp Val Ala Gly Ile Asp Asp Gly Asp Ser Asp Thr Arg Tyr
 65              70              75                  80

Ala Pro Ala Val Lys Gly Arg Ala Thr Ile Ser Arg Asp Asn Ser Lys
                85              90                  95

Asn Thr Val Tyr Leu Gln Met Asn Ser Leu Arg Ala Glu Asp Thr Ala
                100             105                 110

Val Tyr Tyr Cys Ala Lys His Thr Gly Ile Gly Ala Asn Ser Ala Gly
            115             120             125

Ser Ile Asp Ala Trp Gly Gln Gly Thr Leu Val Thr Val Ser Ser Ala
    130             135             140

Ser Thr Lys Gly Pro Ser Val Phe Pro Leu Ala Pro Ser Ser Lys Ser
145             150             155                 160

Thr Ser Gly Gly Thr Ala Ala Leu Gly Cys Leu Val Lys Asp Tyr Phe
                165             170             175

Pro Glu Pro Val Thr Val Ser Trp Asn Ser Gly Ala Leu Thr Ser Gly
            180             185             190

Val His Thr Phe Pro Ala Val Leu Gln Ser Ser Gly Leu Tyr Ser Leu
        195             200             205

Ser Ser Val Val Thr Val Pro Ser Ser Ser Leu Gly Thr Gln Thr Tyr
    210             215             220

Ile Cys Asn Val Asn His Lys Pro Ser Asn Thr Lys Val Asp Lys Lys
225             230             235                 240

Val Glu Pro Lys Ser Cys Asp Lys Thr His Thr Cys Pro Pro Cys Pro
            245             250             255

Ala Pro Glu Leu Leu Gly Gly Pro Ser Val Phe Leu Phe Pro Pro Lys
        260             265             270

Pro Lys Asp Thr Leu Met Ile Ser Arg Thr Pro Glu Val Thr Cys Val
    275             280             285

Val Val Asp Val Ser His Glu Asp Pro Glu Val Lys Phe Asn Trp Tyr
            290             295             300

Val Asp Gly Val Glu Val His Asn Ala Lys Thr Lys Pro Arg Glu Glu
305             310             315                 320

Gln Tyr Asn Ser Thr Tyr Arg Val Val Ser Val Leu Thr Val Leu His
                325             330             335

Gln Asp Trp Leu Asn Gly Lys Glu Tyr Lys Cys Lys Val Ser Asn Lys
            340             345             350

Ala Leu Pro Ala Pro Ile Glu Lys Thr Ile Ser Lys Ala Lys Gly Gln
        355             360             365

Pro Arg Glu Pro Gln Val Tyr Thr Leu Pro Pro Ser Arg Glu Glu Met
    370             375             380

Thr Lys Asn Gln Val Ser Leu Thr Cys Leu Val Lys Gly Phe Tyr Pro
385             390             395                 400

Ser Asp Ile Ala Val Glu Trp Glu Ser Asn Gly Gln Pro Glu Asn Asn
                405             410             415

Tyr Lys Thr Thr Pro Pro Val Leu Asp Ser Asp Gly Ser Phe Phe Leu
            420             425             430

Tyr Ser Lys Leu Thr Val Asp Lys Ser Arg Trp Gln Gln Gly Asn Val
        435             440             445

Phe Ser Cys Ser Val Met His Glu Ala Leu His Asn His Tyr Thr Gln
    450             455             460

Lys Ser Leu Ser Leu Ser Pro Gly Lys
```

<210> SEQ ID NO 50
<211> LENGTH: 1422
<212> TYPE: DNA
<213> ORGANISM: Artificial
<220> FEATURE:
<223> OTHER INFORMATION: Base sequence coding amino acid sequence of heavy chain of humanized antibody

<400> SEQUENCE: 50

```
atggagtttg gcctgtcctg gctgttcctg gtcgcaatcc tgaagggcgt gcagtgtgaa      60
gtgcagctgc tggagagcgg ggggggactg gtgcagcccg gcgggagtct gagactgtca     120
tgcgccgcta gcgggttcac ttttagctcc tacccaatgg gatgggtcag gcaggcacct     180
ggcaagggac tggagtgggt ggctggcatc gacgatgacg gggattctga cacccgatac     240
gctcctgcag tgaagggacg agccaccatt tccagagata actctaaaaa tacagtctat     300
ctgcagatga cagcctgcg agctgaagac actgcagtgt actattgcgc caagcacacc     360
ggaatcggcg ccaattctgc tggcagtatt gatgcttggg ggcagggaac cctggtcaca     420
gtgtctagtg ctagtacaaa ggggccctca gtgttccac tggcaccctc aagcaaaagt     480
acttcaggag gaaccgcagc actgggatgt ctggtgaagg actactccc agagcccgtc     540
actgtgtcat ggaacagcgg agcactgacc agcggcgtcc atacatttcc tgccgtgctg     600
cagtcctctg gactgtactc cctgagttca gtggtcaccg tgccaagctc ctctctgggc     660
actcagacct atatctgcaa cgtgaatcac aagcctagta tacaaaagt cgataagaaa     720
gtggagccaa agagctgtga caaaacacat acttgccccc cttgtcctgc cccagaactg     780
ctgggggac caagcgtgtt cctgtttcca cccaagccca agatacccct gatgattagc     840
aggacaccag aggtcacttg cgtggtcgtg gatgtgtccc acgaggaccc cgaagtcaag     900
tttaactggt acgtggacgg cgtcgaagtg cataatgcca gacaaaacc cagggaggaa     960
cagtacaaca gcacatatcg cgtcgtgtcc gtcctgactg tgctgcacca ggattggctg    1020
aacggaaaag agtacaagtg caaagtgtct aataaggcac tgcccgcccc tatcgagaaa    1080
acaattagca aggcaaaagg ccagcctcga gaaccacagg tgtacactct gcctccatcc    1140
cgggaggaaa tgactaagaa ccaggtctct ctgacctgtc tggtgaaagg cttctatccc    1200
tcagacatcg ctgtggagtg ggaaagcaat gggcagcctg agaacaatta caagaccaca    1260
ccccctgtgc tggattccga cgggtctttc tttctgtatt ctaagctgac cgtggacaaa    1320
agtcggtggc agcagggaaa tgtctttagc tgttccgtga tgcacgaagc actgcacaac    1380
cactacactc agaagagcct gtcactgtca cctggaaaat aa                       1422
```

<210> SEQ ID NO 51
<211> LENGTH: 233
<212> TYPE: PRT
<213> ORGANISM: Artificial
<220> FEATURE:
<223> OTHER INFORMATION: Light chain of humanized antibody Humanized-1

<400> SEQUENCE: 51

Met Ala Trp Ile Pro Leu Leu Leu Pro Leu Leu Thr Leu Cys Thr Gly
1               5                   10                  15

Ser Glu Ala Ser Tyr Glu Leu Thr Gln Pro Pro Ser Val Ser Val Ser
                20                  25                  30

Pro Gly Gln Thr Ala Arg Ile Thr Cys Ser Gly Gly Gly Ser Tyr Thr
            35                  40                  45

Gly Ser Tyr Tyr Tyr Gly Trp Tyr Gln Gln Lys Pro Gly Gln Ala Pro
    50                  55                  60

Val Thr Met Ile Tyr Tyr Asn Asn Lys Arg Pro Ser Asp Ile Pro Glu
65                  70                  75                  80

Arg Phe Ser Gly Ser Leu Ser Gly Thr Thr Asn Thr Leu Thr Ile Ser
                85                  90                  95

Gly Val Gln Ala Glu Asp Glu Ala Asp Tyr Tyr Cys Gly Ser Ala Asp
                100                 105                 110

Asn Ser Gly Asp Ala Phe Gly Thr Gly Thr Lys Val Thr Val Leu Gly
                115                 120                 125

Gln Pro Lys Ala Asn Pro Thr Val Thr Leu Phe Pro Pro Ser Ser Glu
            130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
                180                 185                 190

Tyr Ala Ala Ser Ser Tyr Leu Ser Leu Thr Pro Glu Gln Trp Lys Ser
                195                 200                 205

His Arg Ser Tyr Ser Cys Gln Val Thr His Glu Gly Ser Thr Val Glu
            210                 215                 220

Lys Thr Val Ala Pro Thr Glu Cys Ser
225                 230

<210> SEQ ID NO 52
<211> LENGTH: 702
<212> TYPE: DNA
<213> ORGANISM: Artificial
<220> FEATURE:
<223> OTHER INFORMATION: Base sequence coding amino acid sequence of
      light chain of humanized antibody Humanized-1

<400> SEQUENCE: 52
atggcatgga ttcctctgct gctgcctctg ctgaccctgt gcaccgggag cgaagcctca      60
tacgaactga cccagccccc tagcgtctcc gtgtctcccg gcagactgc aaggatcacc     120 tgcagcggag gaggatccta taccgggtct tactattacg gatggtacca gcagaagcca     180
ggacaggctc ccgtgacaat gatctattac aacaacaagc ggccttctga cattccagag     240
cggttcagcg gatcactgag cggcaccaca aacactctga ccattagcgg ggtgcaggcc     300
gaggacgaag ctgattatta ctgcggcagt gcagacaata gcggggatgc cttcggcaca     360
gggactaaag tgactgtcct gggccagccc aaagccaacc ctaccgtgac actgtttccc     420
cctagctccg aggaactgca ggcaaataag gccacactgg tctgtctgat cagcgacttc     480
tatcctggag ctgtgactgt cgcttggaag gcagattcta gtccagtgaa agcaggcgtc     540
gagactacca cacccagtaa gcagtcaaac aacaagtatg ccgcttcaag ctacctgagc     600
ctgaccccag aacagtggaa atcccaccgg tcctactctt gtcaggtcac tcacgagggc     660
tcaactgtgg agaaaactgt cgcaccaacc gaatgttcct aa                       702

<210> SEQ ID NO 53
<211> LENGTH: 233
<212> TYPE: PRT
<213> ORGANISM: Artificial
<220> FEATURE:
<223> OTHER INFORMATION: Light chain of humanized antibody Humanized-2

<400> SEQUENCE: 53

```
Met Ala Trp Ile Pro Leu Leu Leu Pro Leu Leu Thr Leu Cys Thr Gly
1               5                   10                  15

Ser Glu Ala Ser Tyr Glu Leu Thr Gln Pro Pro Ser Val Ser Val Ser
            20                  25                  30

Pro Gly Gln Thr Ala Arg Ile Thr Cys Ser Gly Gly Ser Tyr Thr
        35                  40                  45

Gly Ser Tyr Tyr Tyr Gly Trp Tyr Gln Gln Lys Pro Gly Gln Ala Pro
    50                  55                  60

Val Thr Val Ile Tyr Tyr Asn Asn Lys Arg Pro Ser Asp Ile Pro Glu
65                  70                  75                  80

Arg Phe Ser Gly Ser Leu Ser Gly Thr Thr Asn Thr Leu Thr Ile Ser
                85                  90                  95

Gly Val Gln Ala Glu Asp Glu Ala Asp Tyr Tyr Cys Gly Ser Ala Asp
            100                 105                 110

Asn Ser Gly Asp Ala Phe Gly Thr Gly Thr Lys Val Thr Val Leu Gly
        115                 120                 125

Gln Pro Lys Ala Asn Pro Thr Val Thr Leu Phe Pro Pro Ser Ser Glu
130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230
```

<210> SEQ ID NO 54
<211> LENGTH: 702
<212> TYPE: DNA
<213> ORGANISM: Artificial
<220> FEATURE:
<223> OTHER INFORMATION: Base sequence coding amino acid sequence of light chain of humanized antibody Humanized-2

<400> SEQUENCE: 54

```
atggcatgga ttcctctgct gctgcctctg ctgaccctgt gcaccgggag cgaagcctca      60
tacgaactga cccagccccc tagcgtctcc gtgtctcccg gcagactgca aggatcacc     120 tgcagcggag gaggatccta taccgggtct tactattacg gatggtacca gcagaagcca     180
ggacaggctc ccgtgacagt gatctattac aacaacaagc ggccttctga cattccagag     240
cggttcagcg gatcactgag cggcaccaca aacactctga ccattagcgg ggtgcaggcc     300
gaggacgaag ctgattatta ctgcggcagt gcagacaata gcggggatgc cttcggcaca     360
gggactaaag tgactgtcct gggccagccc aaagccaacc ctaccgtgac actgtttccc     420
cctagctccg aggaactgca ggcaaataag gccacactgg tctgtctgat cagcgacttc     480
tatcctggag ctgtgactgt cgcttggaag gcagattcta gtccagtgaa agcaggcgtc     540
gagactacca cacccagtaa gcagtcaaac aacaagtatg ccgcttcaag ctacctgagc     600
```

```
ctgaccccag aacagtggaa atcccaccgg tcctactctt gtcaggtcac tcacgagggc    660
tcaactgtgg agaaaactgt cgcaccaacc gaatgttcct aa                       702
```

<210> SEQ ID NO 55
<211> LENGTH: 473
<212> TYPE: PRT
<213> ORGANISM: Artificial
<220> FEATURE:
<223> OTHER INFORMATION: Heavy chain of chicken-human chimera antibody

<400> SEQUENCE: 55

```
Met Ser Pro Leu Val Ser Ser Leu Leu Leu Ala Ala Leu Pro Gly
1               5                   10                  15

Leu Met Ala Ala Val Thr Leu Asp Glu Ser Gly Gly Gly Leu Gln Thr
            20                  25                  30

Pro Gly Gly Ala Leu Ser Leu Val Cys Lys Ala Ser Gly Phe Thr Phe
        35                  40                  45

Ser Ser Tyr Pro Met Gly Trp Val Arg Gln Ala Pro Gly Lys Gly Leu
    50                  55                  60

Glu Trp Val Ala Gly Ile Asp Asp Gly Asp Ser Asp Thr Arg Tyr
65                  70                  75                  80

Ala Pro Ala Val Lys Gly Arg Ala Thr Ile Ser Arg Asp Asn Gly Gln
                85                  90                  95

Ser Thr Val Arg Leu Gln Leu Asn Asn Leu Arg Ala Glu Asp Thr Gly
            100                 105                 110

Thr Tyr Tyr Cys Ala Lys His Thr Gly Ile Gly Ala Asn Ser Ala Gly
        115                 120                 125

Ser Ile Asp Ala Trp Gly His Gly Thr Glu Val Ile Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350
```

```
Ala Leu Pro Ala Pro Ile Glu Lys Thr Ile Ser Lys Ala Lys Gly Gln
            355                 360                 365
Pro Arg Glu Pro Gln Val Tyr Thr Leu Pro Pro Ser Arg Glu Glu Met
    370                 375                 380
Thr Lys Asn Gln Val Ser Leu Thr Cys Leu Val Lys Gly Phe Tyr Pro
385                 390                 395                 400
Ser Asp Ile Ala Val Glu Trp Glu Ser Asn Gly Gln Pro Glu Asn Asn
                405                 410                 415
Tyr Lys Thr Thr Pro Pro Val Leu Asp Ser Asp Gly Ser Phe Phe Leu
            420                 425                 430
Tyr Ser Lys Leu Thr Val Asp Lys Ser Arg Trp Gln Gln Gly Asn Val
            435                 440                 445
Phe Ser Cys Ser Val Met His Glu Ala Leu His Asn His Tyr Thr Gln
450                 455                 460
Lys Ser Leu Ser Leu Ser Pro Gly Lys
465                 470

<210> SEQ ID NO 56
<211> LENGTH: 1422
<212> TYPE: DNA
<213> ORGANISM: Artificial
<220> FEATURE:
<223> OTHER INFORMATION: Base sequence coding amino acid sequence of
      heavy chain of chicke n-human chimera antibody

<400> SEQUENCE: 56
atgagcccac tcgtctcctc cctcctgctc ctggccgccc tgccagggct gatggcggcc      60
gtgacgttgg acgagtccgg gggcggcctc cagacgcccg ggggagcgct cagcctcgtc     120
tgcaaggcct ccgggttcac cttcagcagt tatcccatgg gttgggtgcg acaggcgccc     180
ggcaaggggc tggagtgggt cgctggtatt gatgatgatg gtgatagtga cacaagatac     240
gcgccggcgc tgaagggccg tgccaccatc tcgaggacaa cgggcagag cacagtgagg      300 ctgcagctga acaacctcag ggctgaggac accggcacct actactgcgc caaacatact     360
ggtattggtg ctaatagtgc tggtagcatc gacgcatggg gccacgggac cgaagtcatc     420
gtctcctccg ctagtacaaa ggggccctca gtgttccaac tggcacccct aagcaaaagt     480
acttcaggag gaaccgcagc actgggatgt ctggtgaagg actacttccc agagcccgtc     540
actgtgtcat ggaacagcgg agcactgacc agcggcgtcc atacatttcc tgccgtgctg     600
cagtcctctg gactgtactc cctgagttca gtggtcaccg tgccaagctc ctctctgggc     660
actcagacct atatctgcaa cgtgaatcac aagcctagta atacaaaagt cgataagaaa     720
gtggagccaa agagctgtga caaaacacat acttgccccc cttgtcctgc cccagaactg     780 ctgggggggac caagcgtgtt cctgtttcca cccaagccca agatacccct gatgattagc     840
aggacaccag aggtcacttg cgtggtcgtg gatgtgtccc acgaggaccc cgaagtcaag     900
tttaactggt acgtggacgg cgtcgaagtg cataatgcca agacaaaacc caggaggaa      960 cagtacaaca gcacatatcg cgtcgtgtcc gtcctgactg tgctgcacca ggattggctg    1020
aacggaaaag agtacaagtg caaagtgtct aataaggcac tgcccgcccc tatcgagaaa    1080
acaattagca aggcaaaagg ccagcctcga gaaccacagg tgtacactct gcctccatcc    1140
cgggaggaaa tgactaagaa ccaggtctct ctgacctgtc tggtgaaagg cttctatccc    1200
tcagacatcg ctgtggagtg ggaaagcaat gggcagcctg agaacaatta caagaccaca    1260 cccccttgtgc tggattccga cgggtctttc tttctgtatt ctaagctgac cgtggacaaa    1320
```
agtcggtggc agcagggaaa tgtctttagc tgttccgtga tgcacgaagc actgcacaac    1380
cactacactc agaagagcct gtcactgtca cctggaaaat aa    1422

<210> SEQ ID NO 57
<211> LENGTH: 234
<212> TYPE: PRT
<213> ORGANISM: Artificial
<220> FEATURE:
<223> OTHER INFORMATION: Light chain of chicken-human chimera antibody

<400> SEQUENCE: 57

Met Ala Trp Ala Pro Leu Leu Leu Ala Val Leu Ala His Thr Ser Gly
1               5                   10                  15

Ser Leu Val Gln Ala Ala Leu Thr Gln Pro Ala Ser Val Ser Ala Asn
            20                  25                  30

Leu Gly Gly Thr Val Lys Ile Thr Cys Ser Gly Gly Ser Tyr Thr
        35                  40                  45

Gly Ser Tyr Tyr Tyr Gly Trp Tyr Gln Gln Lys Ser Pro Gly Ser Ala
    50                  55                  60

Leu Val Thr Met Ile Tyr Tyr Asn Asn Lys Arg Pro Ser Asp Ile Pro
65                  70                  75                  80

Ser Arg Phe Ser Gly Ser Leu Ser Gly Ser Thr Asn Thr Leu Thr Ile
                85                  90                  95

Thr Gly Val Arg Ala Asp Asp Glu Ala Val Tyr Phe Cys Gly Ser Ala
            100                 105                 110

Asp Asn Ser Gly Asp Ala Phe Gly Ala Gly Thr Thr Leu Thr Val Leu
        115                 120                 125

Gly Gln Pro Lys Ala Asn Pro Thr Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
        195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser
225                 230

<210> SEQ ID NO 58
<211> LENGTH: 705
<212> TYPE: DNA
<213> ORGANISM: Artificial
<220> FEATURE:
<223> OTHER INFORMATION: Base sequence coding amino acid sequence of
      light chain of chicke n-human chimera antibody

<400> SEQUENCE: 58
atggcctggg ctcctctcct cctggcggtg ctcgcccaca cctcaggttc cctggtgcag    60
gcagcgctga ctcagccggc ctcggtgtca gcaaacctgg gaggaaccgt caagatcacc    120
tgctccgggg gtggcagcta tactggaagt tactattatg gctggtacca gcagaagtct    180
cctggcagtg cccttgtcac tatgatctat tacaacaaca gagaccctcc ggacatccct    240

```
tcacgattct ccggttccct atccggctcc acaaacacat taaccatcac tggggtccga    300
gccgatgacg aggctgtcta tttctgtggg agtgcagaca acagtggtga tgcatttggg    360
gccgggacaa ccctgaccgt cctaggccag cccaaagcca accctaccgt gacactgttt    420 cccctagct ccgaggaact gcaggcaaat aaggccacac tggtctgtct gatcagcgac    480
ttctatcctg gagctgtgac tgtcgcttgg aaggcagatt ctagtccagt gaaagcaggc    540
gtcgagacta ccacacccag taagcagtca acaacaagt atgccgcttc aagctacctg    600
agcctgaccc cagaacagtg gaaatcccac cggtcctact cttgtcaggt cactcacgag    660
ggctcaactg tggagaaaac tgtcgcacca accgaatgtt cctaa                   705
```

```
<210> SEQ ID NO 59
<211> LENGTH: 120
<212> TYPE: PRT
<213> ORGANISM: Artificial
<220> FEATURE:
<223> OTHER INFORMATION: Heavy chain variable region of chicken-mouse
      chimera antibody clo ne No. 165

<400> SEQUENCE: 59

Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Thr Phe Ser Ser Tyr
            20                  25                  30

Glu Met Gln Trp Val Arg Gln Ala Pro Gly Lys Gly Leu Glu Trp Val
        35                  40                  45

Ala Gly Ile Tyr Thr Gly Ser Thr Trp Tyr Gly Ala Ala Val Lys Gly
    50                  55                  60

Arg Ala Thr Ile Ser Arg Asp Asn Gly Gln Ser Thr Val Arg Leu Gln
65                  70                  75                  80

Leu Asn Asn Leu Arg Ala Glu Asp Thr Ala Ile Tyr Tyr Cys Ala Lys
                85                  90                  95

Ser Gly Ile Gly Val Asn Ser Ala Ala Phe Ile Asp Ala Trp Gly His
            100                 105                 110

Gly Thr Glu Val Ile Val Ser Ser
        115                 120

<210> SEQ ID NO 60
<211> LENGTH: 5
<212> TYPE: PRT
<213> ORGANISM: Gallus gallus

<400> SEQUENCE: 60

Ser Tyr Glu Met Gln
1               5

<210> SEQ ID NO 61
<211> LENGTH: 15
<212> TYPE: PRT
<213> ORGANISM: Gallus gallus

<400> SEQUENCE: 61

Gly Ile Tyr Thr Gly Ser Thr Trp Tyr Gly Ala Ala Val Lys Gly
1               5                   10                  15

<210> SEQ ID NO 62
<211> LENGTH: 13
<212> TYPE: PRT
<213> ORGANISM: Gallus gallus
```

```
<400> SEQUENCE: 62

Ser Gly Ile Gly Val Asn Ser Ala Ala Phe Ile Asp Ala
1               5                   10

<210> SEQ ID NO 63
<211> LENGTH: 107
<212> TYPE: PRT
<213> ORGANISM: Artificial
<220> FEATURE:
<223> OTHER INFORMATION: Light chain variable region of chicken-mouse
      chimera antibody clo ne No. 165

<400> SEQUENCE: 63

Ala Leu Thr Gln Pro Ala Ser Val Ser Ala Asn Pro Gly Glu Thr Val
1               5                   10                  15

Lys Ile Thr Cys Ser Gly Gly Gly Ser Tyr Gly Gly Ser Tyr Tyr Tyr
            20                  25                  30

Gly Trp Tyr Gln Gln Lys Ala Pro Gly Ser Ala Pro Val Thr Val Ile
        35                  40                  45

Tyr Asn Asn Asn Lys Arg Pro Ser Asn Ile Pro Ser Arg Phe Ser Gly
50                  55                  60

Ser Leu Ser Gly Ser Thr Asn Thr Leu Thr Ile Thr Gly Val Arg Ala
65                  70                  75                  80

Asp Asp Glu Ala Val Tyr Phe Cys Gly Ser Ala Asp Asn Ser Gly Thr
                85                  90                  95

Ala Phe Gly Ala Gly Thr Thr Leu Thr Val Leu
            100                 105

<210> SEQ ID NO 64
<211> LENGTH: 13
<212> TYPE: PRT
<213> ORGANISM: Gallus gallus

<400> SEQUENCE: 64

Ser Gly Gly Gly Ser Tyr Gly Gly Ser Tyr Tyr Tyr Gly
1               5                   10

<210> SEQ ID NO 65
<211> LENGTH: 7
<212> TYPE: PRT
<213> ORGANISM: Gallus gallus

<400> SEQUENCE: 65

Asn Asn Asn Lys Arg Pro Ser
1               5

<210> SEQ ID NO 66
<211> LENGTH: 9
<212> TYPE: PRT
<213> ORGANISM: Gallus gallus

<400> SEQUENCE: 66

Gly Ser Ala Asp Asn Ser Gly Thr Ala
1               5

<210> SEQ ID NO 67
<211> LENGTH: 120
<212> TYPE: PRT
<213> ORGANISM: Artificial
<220> FEATURE:
<223> OTHER INFORMATION: Heavy chain variable region of chicken-mouse
      chimera antibody clo ne No. 582
```

<400> SEQUENCE: 67

Ala Val Thr Leu Asp Glu Ser Gly Gly Leu Gln Thr Pro Gly Gly
1               5                   10                  15

Ala Leu Ser Leu Val Cys Lys Ala Ser Gly Phe Thr Met Ser Ser Tyr
            20                  25                  30

Glu Met Gln Trp Val Arg Gln Ala Pro Gly Lys Gly Leu Glu Trp Val
        35                  40                  45

Ala Ala Ile Tyr Thr Arg Ser Thr Trp Tyr Gly Ala Ala Val Lys Gly
50                  55                  60

Arg Ala Thr Ile Ser Arg Asp Asn Gly Gln Ser Thr Val Arg Leu Gln
65                  70                  75                  80

Leu Asn Asn Leu Arg Ala Glu Asp Thr Gly Thr Tyr Tyr Cys Ala Lys
                85                  90                  95

Ser Gly Ile Gly Leu Asn Ser Ala Ala Phe Ile Asp Ala Trp Gly His
            100                 105                 110

Gly Thr Glu Val Ile Val Ser Ser
        115                 120

<210> SEQ ID NO 68
<211> LENGTH: 5
<212> TYPE: PRT
<213> ORGANISM: Gallus gallus

<400> SEQUENCE: 68

Ser Tyr Glu Met Gln
1               5

<210> SEQ ID NO 69
<211> LENGTH: 15
<212> TYPE: PRT
<213> ORGANISM: Gallus gallus

<400> SEQUENCE: 69

Ala Ile Tyr Thr Arg Ser Thr Trp Tyr Gly Ala Ala Val Lys Gly
1               5                   10                  15

<210> SEQ ID NO 70
<211> LENGTH: 13
<212> TYPE: PRT
<213> ORGANISM: Gallus gallus

<400> SEQUENCE: 70

Ser Gly Ile Gly Leu Asn Ser Ala Ala Phe Ile Asp Ala
1               5                   10

<210> SEQ ID NO 71
<211> LENGTH: 107
<212> TYPE: PRT
<213> ORGANISM: Artificial
<220> FEATURE:
<223> OTHER INFORMATION: Light chain variable region of chicken-mouse chimera antibody clo ne No. 582

<400> SEQUENCE: 71

Ala Leu Thr Gln Pro Ala Ser Val Ser Ala Asn Pro Gly Glu Thr Val
1               5                   10                  15

Lys Ile Thr Cys Ser Gly Gly Gly Ser Tyr Gly Gly Ser Tyr Tyr Tyr
            20                  25                  30

Gly Trp Tyr Gln Gln Lys Ala Pro Gly Ser Ala Pro Val Thr Val Ile
        35                  40                  45

```
Tyr Thr Asn Asn Lys Arg Pro Ser Asn Ile Pro Ser Arg Phe Ser Gly
    50                  55                  60

Ser Leu Ser Gly Ser Thr Asn Thr Leu Thr Ile Thr Gly Val Arg Ala
65                  70                  75                  80

Asp Asp Glu Ala Val Tyr Phe Cys Gly Ser Ala Asp Asn Ser Gly Thr
                85                  90                  95

Ala Phe Gly Ala Gly Thr Thr Leu Thr Val Leu
            100                 105
```

<210> SEQ ID NO 72
<211> LENGTH: 13
<212> TYPE: PRT
<213> ORGANISM: Gallus gallus

<400> SEQUENCE: 72

```
Ser Gly Gly Gly Ser Tyr Gly Gly Ser Tyr Tyr Tyr Gly
1               5                   10
```

<210> SEQ ID NO 73
<211> LENGTH: 7
<212> TYPE: PRT
<213> ORGANISM: Gallus gallus

<400> SEQUENCE: 73

```
Thr Asn Asn Lys Arg Pro Ser
1               5
```

<210> SEQ ID NO 74
<211> LENGTH: 9
<212> TYPE: PRT
<213> ORGANISM: Gallus gallus

<400> SEQUENCE: 74

```
Gly Ser Ala Asp Asn Ser Gly Thr Ala
1               5
```

<210> SEQ ID NO 75
<211> LENGTH: 121
<212> TYPE: PRT
<213> ORGANISM: Gallus gallus

<400> SEQUENCE: 75

```
Ala Val Thr Leu Asp Glu Ser Gly Gly Leu Gln Thr Pro Gly Gly
1               5                   10                  15

Ala Leu Ser Leu Val Cys Lys Ala Ser Gly Phe Thr Phe Ser Ser Tyr
            20                  25                  30

Asp Met Asn Trp Val Arg Gln Ala Pro Gly Lys Gly Leu Glu Trp Val
        35                  40                  45

Ala Gly Ile Tyr Ser Gly Ser Ser Thr Tyr Tyr Gly Ala Ala Val Lys
    50                  55                  60

Gly Arg Ala Thr Ile Ser Arg Asp Asn Gly Gln Ser Thr Leu Arg Leu
65                  70                  75                  80

Gln Leu Asn Asn Leu Arg Ala Glu Asp Thr Gly Ile Tyr Tyr Cys Ala
                85                  90                  95

Lys Ser Ala Ile Pro Val Asn Ser Ala Gly Ser Ile Asp Ala Trp Gly
            100                 105                 110

His Gly Thr Glu Val Ile Val Ser Ser
        115                 120
```

<210> SEQ ID NO 76

```
<211> LENGTH: 5
<212> TYPE: PRT
<213> ORGANISM: Gallus gallus

<400> SEQUENCE: 76

Ser Tyr Asp Met Asn
1               5

<210> SEQ ID NO 77
<211> LENGTH: 16
<212> TYPE: PRT
<213> ORGANISM: Gallus gallus

<400> SEQUENCE: 77

Gly Ile Tyr Ser Gly Ser Ser Thr Tyr Tyr Gly Ala Ala Val Lys Gly
1               5                   10                  15

<210> SEQ ID NO 78
<211> LENGTH: 13
<212> TYPE: PRT
<213> ORGANISM: Gallus gallus

<400> SEQUENCE: 78

Ser Ala Ile Pro Val Asn Ser Ala Gly Ser Ile Asp Ala
1               5                   10

<210> SEQ ID NO 79
<211> LENGTH: 107
<212> TYPE: PRT
<213> ORGANISM: Gallus gallus

<400> SEQUENCE: 79

Ala Leu Thr Gln Pro Ala Ser Val Ser Ala Asn Pro Gly Glu Thr Val
1               5                   10                  15

Lys Ile Thr Cys Ser Gly Gly Gly Ser Tyr Gly Gly Ser Tyr Tyr Tyr
            20                  25                  30

Ser Trp His Gln Gln Lys Ser Pro Gly Ser Ala Leu Val Thr Val Ile
        35                  40                  45

Tyr Tyr Asn Asn Lys Arg Pro Ser Asp Ile Pro Ser Arg Phe Ser Gly
    50                  55                  60

Ser Leu Ser Gly Ser Thr Asn Thr Leu Thr Ile Thr Gly Val Arg Ala
65                  70                  75                  80

Asp Asp Glu Ala Val Tyr Phe Cys Gly Ser Ala Asp Thr Ser Gly Thr
                85                  90                  95

Ala Phe Gly Ala Gly Thr Thr Leu Thr Val Leu
            100                 105

<210> SEQ ID NO 80
<211> LENGTH: 13
<212> TYPE: PRT
<213> ORGANISM: Gallus gallus

<400> SEQUENCE: 80

Ser Gly Gly Gly Ser Tyr Gly Gly Ser Tyr Tyr Tyr Ser
1               5                   10

<210> SEQ ID NO 81
<211> LENGTH: 7
<212> TYPE: PRT
<213> ORGANISM: Gallus gallus

<400> SEQUENCE: 81
```

-continued

Tyr Asn Asn Lys Arg Pro Ser
1               5

<210> SEQ ID NO 82
<211> LENGTH: 9
<212> TYPE: PRT
<213> ORGANISM: Gallus gallus

<400> SEQUENCE: 82

Gly Ser Ala Asp Thr Ser Gly Thr Ala
1               5

<210> SEQ ID NO 83
<211> LENGTH: 120
<212> TYPE: PRT
<213> ORGANISM: Gallus gallus

<400> SEQUENCE: 83

Ala Val Thr Leu Asp Glu Ser Gly Gly Leu Gln Thr Pro Gly Gly
1               5                   10                  15

Ala Leu Ser Leu Val Cys Lys Ala Ser Gly Phe Thr Phe Ser Ser Tyr
            20                  25                  30

Glu Met Gln Trp Val Arg Gln Ala Pro Gly Lys Gly Leu Glu Trp Val
        35                  40                  45

Ala Gly Ile Tyr Ser Gly Ser Thr Trp Tyr Gly Ala Ala Val Lys Gly
    50                  55                  60

Arg Ala Thr Ile Ser Arg Asp Asn Gly Gln Ser Thr Val Arg Leu Gln
65                  70                  75                  80

Leu Asn Asn Leu Arg Ala Glu Asp Thr Gly Thr Tyr Tyr Cys Ala Lys
                85                  90                  95

Ser Gly Ile Gly Phe Asn Ser Ala Gly Ser Ile Asp Ala Trp Gly His
            100                 105                 110

Gly Thr Glu Val Ile Val Ser Ser
        115                 120

<210> SEQ ID NO 84
<211> LENGTH: 5
<212> TYPE: PRT
<213> ORGANISM: Gallus gallus

<400> SEQUENCE: 84

Ser Tyr Glu Met Gln
1               5

<210> SEQ ID NO 85
<211> LENGTH: 15
<212> TYPE: PRT
<213> ORGANISM: Gallus gallus

<400> SEQUENCE: 85

Gly Ile Tyr Ser Gly Ser Thr Trp Tyr Gly Ala Ala Val Lys Gly
1               5                   10                  15

<210> SEQ ID NO 86
<211> LENGTH: 13
<212> TYPE: PRT
<213> ORGANISM: Gallus gallus

<400> SEQUENCE: 86

Ser Gly Ile Gly Phe Asn Ser Ala Gly Ser Ile Asp Ala
1               5                   10

<210> SEQ ID NO 87
<211> LENGTH: 107
<212> TYPE: PRT
<213> ORGANISM: Gallus gallus

<400> SEQUENCE: 87

Ala Leu Thr Gln Pro Ala Ser Val Ser Ala Asn Pro Gly Glu Thr Val
1               5                   10                  15

Lys Ile Thr Cys Ser Gly Gly Gly Ser Tyr Gly Gly Ser Tyr Tyr Tyr
            20                  25                  30

Ser Trp His Gln Gln Lys Ser Pro Gly Ser Ala Leu Val Thr Val Ile
        35                  40                  45

Tyr Tyr Asn Asn Lys Arg Pro Ser Asp Ile Pro Ser Arg Phe Ser Gly
    50                  55                  60

Ser Leu Ser Gly Ser Thr Asn Thr Leu Thr Ile Thr Gly Val Arg Ala
65                  70                  75                  80

Asp Asp Glu Ala Val Tyr Phe Cys Gly Ser Ala Asp Asn Ser Gly Ser
                85                  90                  95

Ala Phe Gly Ala Gly Thr Thr Leu Thr Val Leu
            100                 105

<210> SEQ ID NO 88
<211> LENGTH: 13
<212> TYPE: PRT
<213> ORGANISM: Gallus gallus

<400> SEQUENCE: 88

Ser Gly Gly Gly Ser Tyr Gly Gly Ser Tyr Tyr Tyr Ser
1               5                   10

<210> SEQ ID NO 89
<211> LENGTH: 7
<212> TYPE: PRT
<213> ORGANISM: Gallus gallus

<400> SEQUENCE: 89

Tyr Asn Asn Lys Arg Pro Ser
1               5

<210> SEQ ID NO 90
<211> LENGTH: 9
<212> TYPE: PRT
<213> ORGANISM: Gallus gallus

<400> SEQUENCE: 90

Gly Ser Ala Asp Asn Ser Gly Ser Ala
1               5

<210> SEQ ID NO 91
<211> LENGTH: 36
<212> TYPE: DNA
<213> ORGANISM: Artificial
<220> FEATURE:
<223> OTHER INFORMATION: Primer M gamma

<400> SEQUENCE: 91
agcttgctag cggccaccat ggcctgggct cctctc                    36

<210> SEQ ID NO 92
<211> LENGTH: 41
<212> TYPE: DNA
<213> ORGANISM: Artificial

-continued

```
<220> FEATURE:
<223> OTHER INFORMATION: Primer N gamma

<400> SEQUENCE: 92
tctggcggcc gctagactca cctaggacgg tcagggttgt c                    41

<210> SEQ ID NO 93
<211> LENGTH: 36
<212> TYPE: DNA
<213> ORGANISM: Artificial
<220> FEATURE:
<223> OTHER INFORMATION: Primer O gamma

<400> SEQUENCE: 93
agcttgctag cggccaccat gagcccactc gtctcc                          36

<210> SEQ ID NO 94
<211> LENGTH: 40
<212> TYPE: DNA
<213> ORGANISM: Artificial
<220> FEATURE:
<223> OTHER INFORMATION: Primer P gamma

<400> SEQUENCE: 94
tctggcggcc gctagactca ccggaggaga cgatgacttc                      40

<210> SEQ ID NO 95
<211> LENGTH: 1249
<212> TYPE: DNA
<213> ORGANISM: Homo sapiens

<400> SEQUENCE: 95
atatgcggcc gcctttctgg ggcacgccgg gcctgaccgg gtcatagctg tttcctgggc   60 tttgggcag ggggtgggct aaggtgacgc aggtggcgcc agccaggcgc acacccaatg    120
cccgtgagcc cagacactgg acgctgaacc tcgcggacag ttaagaaccc aggggcctct   180
gcgccctggg cccagctctg tcccacaccg cggtcacatg gcaccacctc tcttgcagcc   240
agcactaagg gaccatccgt gtttcctctg gctcctagta gcaaatcaac ttcaggggga   300
accgcagcac tgggatgtct ggtcaaagac tacttcccag agcccgtcac cgtgtcatgg   360
aacagcggag cactgactag cggagtccac acctttccag ccgtgctgca gagctccgga   420
ctgtactccc tgtctagtgt ggtcacagtg ccttcaagct ccctggggac tcagacctat   480
atctgcaacg tgaatcacaa gccctccaat actaaagtcg acaagaaagt ggaacctaag   540
tcttgtgata aaacacatac ttgcccccct tgtcctgcac cagagctgct gggaggacct   600
agcgtgttcc tgtttccacc caagccaaaa gacaccctga tgattagtcg aacccctgaa   660
gtcacatgcg tggtcgtgga cgtgagccac gaggatccag aagtcaagtt caactggtac   720
gtggatggcg tcgaggtgca taatgctaag acaaaacccc gggaggaaca gtacaacagt   780
acctatagag tcgtgtcagt cctgacagtg ctgcatcagg actggctgaa cgggaaggaa   840
tataagtgca aagtgtccaa taaggccctg ccgctcctat cgagaaaac tatttctaag    900 gctaaaggcc agccaaggga accccaggtg tacaccctgc ctccatcacg cgacgagctg   960
acaaagaacc aggtcagcct gacttgtctg gtgaaagggt tctatccatc tgatatcgca  1020
gtggagtggg aaagtaatgg acagcccgag aacaattaca agaccacacc ccctgtgctg  1080
gactccgatg gatctttctt tctgtatagc aagctgaccg tggataaatc cagatggcag  1140
cagggcaatg tctttttcttg tagtgtgatg cacgaagccc tgcataacca ctacactcag  1200
```

```
aagtcactgt ccctgtcacc tgaaaaatga gtgccacggc cggcaagcc                1249
```

<210> SEQ ID NO 96
<211> LENGTH: 613
<212> TYPE: DNA
<213> ORGANISM: Homo sapiens

<400> SEQUENCE: 96

```
atatgcggcc gccagaatgg gtcatagctg tttcctgctg caaagagctc aacaaaaca     60
atttagaact ttattaagga ataggggaa gctaggaaga aactcaaaac atcaagattt    120
taaatacgct tcttggtctc cttgctataa ttatctggga taagcatgct gttttctgtc   180
tgtccctaac atgccctgtg attatccgca aacaacacac ccaagggcag aactttgtta   240
cttaaacacc atcctgtttg cttctttcct caggaaccgt ggccgctcca tccgtcttta   300
tctttcctcc atccgacgaa cagctgaagt ccggcaccgc ctccgtggtc tgtctgctga   360
acaacttcta cccccgggag gccaaggtgc agtggaaagt cgacaacgct ctgcagtctg   420
gcaatagtca ggagtcagtg actgaacagg acagcaagga ttccaccttat tctctgagct   480
ccaccctgac actgagcaaa gcagattacg agaagcacaa agtctatgcc tgcgaagtca   540
ctcatcaggg gctgtcctca ccagtcacta aagtttcaa tcggggcgaa tgctaaagtc    600
ggccgtgcaa gcc                                                       613
```

<210> SEQ ID NO 97
<211> LENGTH: 15
<212> TYPE: DNA
<213> ORGANISM: Artificial
<220> FEATURE:
<223> OTHER INFORMATION: Base sequence coding amino acid sequence of
      heavy chain CDR1 of c hicken-mouse chimera antibody clone No. 165

<400> SEQUENCE: 97

```
agttatgaga tgcag                                                     15
```

<210> SEQ ID NO 98
<211> LENGTH: 45
<212> TYPE: DNA
<213> ORGANISM: Artificial
<220> FEATURE:
<223> OTHER INFORMATION: Base sequence coding amino acid sequence of
      heavy chain CDR2 of c hicken-mouse chimera antibody clone No. 165

<400> SEQUENCE: 98

```
ggtatttaca ctggtagcac atggtacggg gcggcggtga agggc                    45
```

<210> SEQ ID NO 99
<211> LENGTH: 39
<212> TYPE: DNA
<213> ORGANISM: Artificial
<220> FEATURE:
<223> OTHER INFORMATION: Base sequence coding amino acid sequence of
      heavy chain CDR3 of c hicken-mouse chimera antibody clone No. 165

<400> SEQUENCE: 99

```
agtggtattg gtgttaatag tgctgctttt atcgacgca                           39
```

<210> SEQ ID NO 100
<211> LENGTH: 39
<212> TYPE: DNA
<213> ORGANISM: Artificial
<220> FEATURE:
<223> OTHER INFORMATION: Base sequence coding amino acid sequence of
      light chain CDR1 of c hicken-mouse chimera antibody clone No. 165

<400> SEQUENCE: 100
tccgggggtg gcagctatgg tggaagttac tattatggc     39

<210> SEQ ID NO 101
<211> LENGTH: 21
<212> TYPE: DNA
<213> ORGANISM: Artificial
<220> FEATURE:
<223> OTHER INFORMATION: Base sequence coding amino acid sequence of
      light chain CDR2 of c hicken-mouse chimera antibody clone No. 165

<400> SEQUENCE: 101
aacaacaaca agagaccctc g     21

<210> SEQ ID NO 102
<211> LENGTH: 27
<212> TYPE: DNA
<213> ORGANISM: Artificial
<220> FEATURE:
<223> OTHER INFORMATION: Base sequence coding amino acid sequence of
      light chain CDR3 of c hicken-mouse chimera antibody clone No. 165

<400> SEQUENCE: 102
gggagtgcag acaacagtgg tactgca     27

<210> SEQ ID NO 103
<211> LENGTH: 360
<212> TYPE: DNA
<213> ORGANISM: Artificial
<220> FEATURE:
<223> OTHER INFORMATION: Base sequence coding amino acid sequence of
      heavy chain of chicke n-mouse chimera antibody clone No. 165

<400> SEQUENCE: 103
gccgtgacgt tggacgagtc cgggggcggc ctccagacgc ccggaggagg gctcagcctc     60
gtctgcaagg cctccgggtt caccttcagc agttatgaga tgcagtgggt gcgacaggcg    120
cccggcaagg ggctggagtg ggtcgctggt atttacactg gtagcacatg gtacggggcg    180
gcggtgaagg gccgtgccac catctcgagg acaacgggc agagcacagt gaggctgcag    240
ctgaacaacc tcagggctga ggacaccgcc atctactact gcgccaaaag tggtattggt    300
gttaatagtg ctgcttttat cgacgcatgg ggccacggga ccgaagtcat cgtctcctcc    360

<210> SEQ ID NO 104
<211> LENGTH: 321
<212> TYPE: DNA
<213> ORGANISM: Artificial
<220> FEATURE:
<223> OTHER INFORMATION: Base sequence coding amino acid sequence of
      light chain of chicke n-mouse chimera antibody clone No. 165

<400> SEQUENCE: 104
gcgctgactc agccggcctc ggtgtcagcg aacccaggag aaaccgtcaa gatcacctgc     60
tccgggggtg gcagctatgg tggaagttac tattatggct ggtaccagca gaaggcacct    120
ggcagtgccc ctgtcactgt gatctataac aacaacaaga gaccctcgaa catcccttca    180
cgattctccg gttccctatc cggctccaca aacacattaa ccatcactgg ggtccgagcc    240
gatgacgagg ctgtctattt ctgtgggagt gcagacaaca gtggtactgc atttggggcc    300
gggacaaccc tgaccgtcct a                                                321

<210> SEQ ID NO 105

<211> LENGTH: 15
<212> TYPE: DNA
<213> ORGANISM: Artificial
<220> FEATURE:
<223> OTHER INFORMATION: Base sequence coding amino acid sequence of
      heavy chain CDR1 of c hicken-mouse chimera antibody clone No. 582

<400> SEQUENCE: 105
agttatgaga tgcag                                                15

<210> SEQ ID NO 106
<211> LENGTH: 45
<212> TYPE: DNA
<213> ORGANISM: Artificial
<220> FEATURE:
<223> OTHER INFORMATION: Base sequence coding amino acid sequence of
      heavy chain CDR2 of c hicken-mouse chimera antibody clone No. 582

<400> SEQUENCE: 106
gctatttaca ctcgtagcac atggtacggg gcggcggtga agggc                45

<210> SEQ ID NO 107
<211> LENGTH: 39
<212> TYPE: DNA
<213> ORGANISM: Artificial
<220> FEATURE:
<223> OTHER INFORMATION: Base sequence coding amino acid sequence of
      heavy chain CDR3 of c hicken-mouse chimera antibody clone No. 582

<400> SEQUENCE: 107
agtggtattg gtcttaatag tgctgctttt atcgacgca                       39

<210> SEQ ID NO 108
<211> LENGTH: 39
<212> TYPE: DNA
<213> ORGANISM: Artificial
<220> FEATURE:
<223> OTHER INFORMATION: Base sequence coding amino acid sequence of
      light chain CDR1 of c hicken-mouse chimera antibody clone No. 582

<400> SEQUENCE: 108
tccggggdtg gcagctatgg tggaagttac tattatggc                       39

<210> SEQ ID NO 109
<211> LENGTH: 21
<212> TYPE: DNA
<213> ORGANISM: Artificial
<220> FEATURE:
<223> OTHER INFORMATION: Base sequence coding amino acid sequence of
      light chain CDR2 of c hicken-mouse chimera antibody clone No. 582

<400> SEQUENCE: 109
accaacaaca agagaccctc g                                          21

<210> SEQ ID NO 110
<211> LENGTH: 27
<212> TYPE: DNA
<213> ORGANISM: Artificial
<220> FEATURE:
<223> OTHER INFORMATION: Base sequence coding amino acid sequence of
      light chain CDR3 of c hicken-mouse chimera antibody clone No. 582

<400> SEQUENCE: 110
gggagtgcag acaacagtgg tactgca                                    27

<210> SEQ ID NO 111
<211> LENGTH: 360

```
<212> TYPE: DNA
<213> ORGANISM: Artificial
<220> FEATURE:
<223> OTHER INFORMATION: Base sequence coding amino acid sequence of
      heavy chain of chicke n-mouse chimera antibody clone No. 582

<400> SEQUENCE: 111
gccgtgacgt tggacgagtc cggggggcggc tccagacgc ccggaggagc gctcagcctc    60
gtctgcaagg cctccgggtt caccatgagc agttatgaga tgcagtgggt gcgacaggcg   120
cccggcaagg ggctggagtg ggtcgctgct atttacactc gtagcacatg gtacggggcg   180
gcggtgaagg gccgtgccac catctcgagg gacaacgggc agagcacagt gaggctgcag   240
ctgaacaacc tcagggctga ggacaccggc acctactact gcgccaaaag tggtattggt   300
cttaatagtg ctgcttttat cgacgcatgg ggccacggga ccgaagtcat cgtctcctcc   360

<210> SEQ ID NO 112
<211> LENGTH: 321
<212> TYPE: DNA
<213> ORGANISM: Artificial
<220> FEATURE:
<223> OTHER INFORMATION: Base sequence coding amino acid sequence of
      light chain of chicke n-mouse chimera antibody clone No. 582

<400> SEQUENCE: 112
gcgctgactc agccggcctc ggtgtcagca aacccaggag aaaccgtcaa gatcacctgc    60
tccgggggtg gcagctatgg tggaagttac tattatggct ggtaccagca gaaggcacct   120
ggcagtgccc ctgtcactgt gatctatacc aacaacaaga cccctcgaa catcccttca    180 cgattctccg gttccctatc cggctccaca aacacattaa ccatcactgg ggtccgagcc   240
gatgacgagg ctgtctattt ctgtgggagt gcagacaaca gtggtactgc atttggggcc   300
gggacaaccc tgaccgtcct a                                              321

<210> SEQ ID NO 113
<211> LENGTH: 15
<212> TYPE: DNA
<213> ORGANISM: Gallus gallus

<400> SEQUENCE: 113
agttacgaca tgaac                                                     15

<210> SEQ ID NO 114
<211> LENGTH: 48
<212> TYPE: DNA
<213> ORGANISM: Gallus gallus

<400> SEQUENCE: 114
ggtatttaca gtggtagtag cacatactac ggggcggcgg tgaagggc                 48

<210> SEQ ID NO 115
<211> LENGTH: 39
<212> TYPE: DNA
<213> ORGANISM: Gallus gallus

<400> SEQUENCE: 115
agtgctattc ctgttaatag tgctggtagc atcgacgca                           39

<210> SEQ ID NO 116
<211> LENGTH: 39
<212> TYPE: DNA
<213> ORGANISM: Gallus gallus
```

```
<400> SEQUENCE: 116 tccggggtg gcagttatgg tggaagttat tactatagc                              39

<210> SEQ ID NO 117
<211> LENGTH: 21
<212> TYPE: DNA
<213> ORGANISM: Gallus gallus

<400> SEQUENCE: 117
tacaacaaca agagaccctc g                                                21

<210> SEQ ID NO 118
<211> LENGTH: 27
<212> TYPE: DNA
<213> ORGANISM: Gallus gallus

<400> SEQUENCE: 118
gggagtgcag acaccagtgg tactgca                                          27

<210> SEQ ID NO 119
<211> LENGTH: 363
<212> TYPE: DNA
<213> ORGANISM: Gallus gallus

<400> SEQUENCE: 119
gccgtgacgt tggacgagtc cggggcggc ctccagacgc ccggggagc gctcagcctc         60 gtctgcaagg cctccgggtt caccttcagc agttacgaca tgaactgggt gcgacaggcg      120
cccggcaagg ggctggaatg ggtcgctggt atttacagtg gtagtagcac atactacggg      180
gcggcggtga agggccgtgc caccatctcg agggacaacg ggcagagcac actgaggctg      240
cagctgaaca acctcagggc tgaggacacc ggcatctact actgcgccaa aagtgctatt      300
cctgttaata gtgctggtag catcgacgca tggggccacg ggaccgaagt catcgtctcc      360
tcc                                                                   363

<210> SEQ ID NO 120
<211> LENGTH: 321
<212> TYPE: DNA
<213> ORGANISM: Gallus gallus

<400> SEQUENCE: 120
gcgctgactc agccggcctc ggtgtcagcg aacccaggag aaaccgtcaa gatcacctgc       60 tccggggtg gcagttatgg tggaagttat tactatagct ggcaccagca gaagtctcct      120
ggcagtgccc ttgtcactgt gatctattac aacaacaaga ccctcggaca tcccttca       180 cgattctccg gttccctatc cggctccaca aacacattaa ccatcactgg ggtccgagcc      240
gatgacgagg ctgtctattt ctgtgggagt gcagacacca gtggtactgc atttggggcc      300
gggacaaccc tgaccgtcct a                                               321

<210> SEQ ID NO 121
<211> LENGTH: 15
<212> TYPE: DNA
<213> ORGANISM: Gallus gallus

<400> SEQUENCE: 121
agttatgaga tgcag                                                       15

<210> SEQ ID NO 122
<211> LENGTH: 45
```

<212> TYPE: DNA
<213> ORGANISM: Gallus gallus

<400> SEQUENCE: 122
ggtatttaca gtggtagcac atggtacggg gcggcggtga agggc          45

<210> SEQ ID NO 123
<211> LENGTH: 39
<212> TYPE: DNA
<213> ORGANISM: Gallus gallus

<400> SEQUENCE: 123
agtggtattg gttttaatag tgctggtagc atcgacgca          39

<210> SEQ ID NO 124
<211> LENGTH: 39
<212> TYPE: DNA
<213> ORGANISM: Gallus gallus

<400> SEQUENCE: 124
tccgggggtg gcagttatgg tggaagttat tactatagc          39

<210> SEQ ID NO 125
<211> LENGTH: 21
<212> TYPE: DNA
<213> ORGANISM: Gallus gallus

<400> SEQUENCE: 125
tacaacaaca agagaccctc g          21

<210> SEQ ID NO 126
<211> LENGTH: 27
<212> TYPE: DNA
<213> ORGANISM: Gallus gallus

<400> SEQUENCE: 126
gggagtgcag acaacagtgg tagtgca          27

<210> SEQ ID NO 127
<211> LENGTH: 360
<212> TYPE: DNA
<213> ORGANISM: Gallus gallus

<400> SEQUENCE: 127
gccgtgacgt tggacgagtc cgggggcggc ctccagacgc ccggggggagc gctcagcctc          60
gtctgcaagg cctccgggtt caccttcagc agttatgaga tgcagtgggt gcgacaggcg         120
cccggcaagg ggctggaatg ggtcgctggt atttacagtg gtagcacatg gtacggggcg         180
gcggtgaagg gccgtgccac catctcgagg gacaacgggc agagcacagt aaggctgcag         240
ctgaacaacc tcagggctga ggacaccggc acctactact gcgccaaaag tggtattggt         300
tttaatagtg ctggtagcat cgacgcatgg ggccacggga ccgaagtcat cgtctcctcc         360

<210> SEQ ID NO 128
<211> LENGTH: 321
<212> TYPE: DNA
<213> ORGANISM: Gallus gallus

<400> SEQUENCE: 128
gcgctgactc agccggcctc ggtgtcagcg aacccaggag aaaccgtcaa gatcacctgc          60
tccgggggtg gcagttatgg tggaagttat tactatagct ggcaccagca gaagtctcct         120

```
ggcagtgccc ttgtcactgt gatctattac aacaacaaga gaccctcgga catcccttca      180
cgattctccg gttccctatc cggctccaca aacacattaa ccatcactgg ggtccgagcc      240
gatgacgagg ctgtctattt ctgtgggagt gcagacaaca gtggtagtgc atttggggcc      300
gggacaaccc tgaccgtcct a                                                321
```

ANTI-SEMAPHORIN 3A ANTIBODY AND TREATMENT OF ALZHEIMER'S DISEASE AND INFLAMMATORY IMMUNE DISEASES USING SAME

CROSS REFERENCE TO RELATED APPLICATIONS

This application is a divisional of U.S. patent application Ser. No. 14/766,062, filed Aug. 5, 2015, which is a U.S. National Phase Application of PCT International Application Number PCT/JP2014/052758, filed on Feb. 6, 2014, designating the United States of America and published in the Japanese language, which is an International Application of and claims the benefit of priority to Japanese Patent Application No. 2013-021309, filed on Feb. 6, 2013. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is SeqList-LEX010-001APC.txt, the date of creation of the ASCII text file is Jul. 23, 2015, and the size of the ASCII text file is 71 KB.

TECHNICAL FIELD

The present invention relates to anti-semaphorin 3A antibody or its antibody fragment effective for prophylaxis and/or treatment of diseases involving semaphoring 3A protein. The present invention also relates to a pharmaceutical composition containing the anti-semaphorin 3A antibody or antibody fragment thereof. Furthermore, the present invention relates to a method for measuring semaphorin 3A protein using anti-semaphorin 3A antibody or its antibody fragment.

BACKGROUND ART

Alzheimer's disease (AD) is the most common form of dementia (loss of memory) in the elderly. Currently used therapeutic agents for Alzheimer's disease have any action mechanism which allows to improve cholinergic neurotransmission in the central nerve system with a cholinesterase inhibitor or suppress excitotoxicity with a N-methyl-D-aspartate (NMDA) type glutamate receptor inhibitor, however, all of the agents only provide mild improvement of the related symptoms. A radical treatment method has been expected to develop which suppresses or ameliorates progression of neurodegeneration responsible for Alzheimer's disease.

Principal pathological damage of AD, which is found in brain, is caused by extracellular deposits of β amyloid protein in the forms of plaques and vascular clogs, and intracellular neurofibrillary tangle of τ protein which is clumped and hyper-phosphorylated. Recent evidences demonstrate that an increased level of β amyloid in brain appears in advance of pathological changes of τ protein and correlates with cognitive decline. Recent studies also suggest that β amyloid is ascribed as the etiology of AD and reveal that clumped β amyloid has toxicity to neurons in cell culture.

β amyloid protein is mainly composed of peptides in the length of 39 to 42 amino acids and is produced from a large protein precursor called as amyloid precursor protein (APP) through consecutive action of protease and β- and γ-secretases. Rare but early onset AD cases are attributed to genetic mutation of APP which causes overproduction of any one of total β amyloid protein and isoforms thereof. Individuals with Down's syndrome have an extra chromosome containing an APP-encoding gene and they have an increased level of β amyloid and inevitably develop AD with age.

Semaphorins are endogenous proteins identified as factors which allow to degenerate nerve growth cone and suppress axon elongation. Semaphorin genes are categorized into eight gene subfamilies and classes based on their structures and are previously known to have approximately 20 molecular species (Non-patent document 1). However, little is known about main functions of most semaphorin families. More frequently studied one is a subfamily gene cluster called as Class III and among them, most frequently studied one is semaphorin 3A (Sema 3A) (Non-patent documents 2 and 3). Sema 3A protein is known to induce degeneration of growth cones in cultured nerve cells and inhibit regeneration and elongation of nerves at a low level of 10 Pm within a short time.

In recent years, one research has been reported that dendritic cells detect Sema 3A protein, subsequently enter a lymph channel and transfer into a lymph node, suggesting that Sema 3A protein is involved in autoimmune disease (See e.g. Non-patent document 4), and other research has revealed that signals mediated by Sema 3A protein and its receptor, plexin-A4, have an important role in the onset of sepsis (See e.g. Non-patent document 6), and from these findings, Sema 3A protein is also known to be deeply involved in formations of pathological conditions of immune and infectious diseases, etc. Additionally, another researches have been reported that Sema 3A protein is secreted by cancer cells and tissues and blocks a signal pathway of mitogen-activated protein kinase (MAP) to suppress activation of T cells, and that pancreatic cancer patients with high expression level of Sema 3A in the cancer tissue have poor outcome, revealing that Sema 3A protein is also involved in malignant alteration of cancer (See, e.g. Non-patent documents 5 and 7).

Disseminated intravascular coagulation (DIC) is a serious pathological condition in which coagulation significantly activates in a systemic and persistent manner along with deteriorated underlying disease. DIC is known that its main symptoms are episodes of bleeding and organ disordering and the occurrence of these clinical symptoms leads to extremely poor outcome. Examples of underlying diseases inductive of DIC include sepsis, acute leukemia, solid cancer, premature separation of normally implanted placenta, amniotic fluid embolism, trauma, burn injury, connective tissue disease, shock, aortic aneurysm, fulminant hepatitis, liver cirrhosis, acute pancreatitis, rhabdomyolysis, thrombosis, severe infectious disease, etc., however, a relationship of the diseases and Sema 3A is not clear.

Previously an antibody to Sema 3A protein has been also reported. For example, researches have been reported that Sema 3A protein activity inhibitor such as anti-Sema 3A antibody is effective for treatment of Alzheimer's disease and Parkinson's disease (See Patent document 1), and also effective for treatment of immune disease and inflammatory disease (See Patent document 2). However, when a disease involving Sema 3A protein is prevented and/or treated with anti-Sema 3A antibody, it is not known a structure of anti-Sema 3A antibody used in order to effectively achieve the high drug efficacy.

As described above, Sema 3A protein is known to be involved in various pathological conditions and a technique for measuring Sema 3A protein in a high accurate manner is essential to elucidate the pathological conditions and develop a therapeutic agent for the conditions.

PRIOR ART DOCUMENTS

Non-Patent Document

Non-Patent Document 1: Cell, 97, 551, 1999
Non-Patent Document 2: Cell, 75, 217, 1993
Non-Patent Document 3: Cell, 75, 1389, 1993
Non-Patent Document 4: Nature Immunology 11, 594-600, 2010
Non-Patent Document 5: Blood 107, 3321-3329, 2006
Non-Patent Document 6: Journal of Experimental Medicine 207, 2943, 2010
Non-Patent Document 7: International Journal of Cancer 121, 2421-2433, 2007

PATENT DOCUMENTS

Patent Document 1: WO 03/007803
Patent Document 2: WO 2011/066284

SUMMARY OF THE INVENTION

Problems to be Solved by the Invention

An object of the present invention is to provide an antibody to Sema 3A protein wherein the antibody can effectively prevent and/or treat diseases involving Sema 3A protein such as neurodegenerative disease, autoimmune disease, inflammatory disease, cancer, infectious disease, etc. and disseminated intravascular coagulation syndrome. Another object of the present invention is to provide a pharmaceutical composition capable of prophylaxis and/or treatment of diseases involving Sema 3A protein as well as amelioration of symptoms associated with such diseases. Still another object of the present invention is to provide an antibody to Sema 3A effective for measuring Sema 3A protein and a method for measuring Sema 3A protein using said antibody.

Means for Solving the Problem

The present inventors have intensively studied to solve the above mentioned problems, and have consequently found that anti-Sema 3A antibody containing a complementary determining region (CDR) having a specific amino sequence can effectively prevent and/or treat neurodegenerative disease such as Alzheimer's disease and significantly ameliorate symptoms associated with the neurodegenerative disease. The anti-Sema 3A antibody also led to drastic improvement of the survival rate and extension of the survival period in a fatal sepsis pathological model. Furthermore, the present inventors have found that the anti-Sema 3A antibody allows to decrease blood level of plasminogen activator inhibitor-1 (PAI-1), an aggravating factor of disseminated intravascular coagulation. Sema 3A induces migration/invasion and drug tolerance of cancer cells. The present inventors have also found that anti-Sema 3A antibody can suppress migration/invasion and drug tolerance of cancer cells and therefore the antibody can minimize malignant alteration of cancer.

Additionally, the present inventors have also found that Sema 3A protein can be measured by ELISA using anti-Sema 3A antibody containing a CDR having a specific amino acid sequence.

The present inventors have further studied based on such findings and completed the present invention. That is, the present invention provides the invention of the following aspects:

Item 1. Anti-semaphorin 3A antibody containing a heavy chain variable region and a light chain variable region shown in any one of the following (A) to (E) or antibody fragment thereof containing an antigen binding region thereof:

(A) a heavy chain variable region containing CDR1 having the amino acid sequence shown in SEQ ID NO:1 or an amino acid sequence in which one or a few amino acids are substituted, deleted, added or inserted in the amino acid sequence shown in SEQ ID NO:1; CDR2 having the amino acid sequence shown in SEQ ID NO:2 or an amino acid sequence in which one or a few amino acids are substituted, deleted, added or inserted in the amino acid sequence shown in SEQ ID NO:2; and CDR3 having the amino acid sequence shown in SEQ ID NO:3 or an amino acid sequence in which one or a few amino acids are substituted, deleted, added or inserted in the amino acid sequence shown in SEQ ID NO:3, and a light chain variable region containing CDR1 having the amino acid sequence shown in SEQ ID NO:4 or an amino acid sequence in which one or a few amino acids are substituted, deleted, added or inserted in the amino acid sequence shown in SEQ ID NO:4; CDR2 having the amino acid sequence shown in SEQ ID NO:5 or an amino acid sequence in which one or a few amino acids are substituted, deleted, added or inserted in the amino acid sequence shown in SEQ ID NO:5; and CDR3 having the amino acid sequence shown in SEQ ID NO:6 or an amino acid sequence in which one or a few amino acids are substituted, deleted, added or inserted in the amino acid sequence shown in SEQ ID NO:6;

(B) a heavy chain variable region containing CDR1 having the amino acid sequence shown in SEQ ID NO:60 or an amino acid sequence in which one or a few amino acids are substituted, deleted, added or inserted in the amino acid sequence shown in SEQ ID NO:60; CDR2 having the amino acid sequence shown in SEQ ID NO:61 or an amino acid sequence in which one or a few amino acids are substituted, deleted, added or inserted in the amino acid sequence shown in SEQ ID NO:61; and CDR3 having the amino acid sequence shown in SEQ ID NO:62 or an amino acid sequence in which one or a few amino acids are substituted, deleted, added or inserted in the amino acid sequence shown in SEQ ID NO:62, and a light chain variable region containing CDR1 having the amino acid sequence shown in SEQ ID NO:64 or an amino acid sequence in which one or a few amino acids are substituted, deleted, added or inserted in the amino acid sequence shown in SEQ ID NO:64; CDR2 having the amino acid sequence shown in SEQ ID NO:65 or an amino acid sequence in which one or a few amino acids are substituted, deleted, added or inserted in the amino acid sequence shown in SEQ ID NO:65; and CDR3 having the amino acid sequence shown in SEQ ID NO:66 or an amino acid sequence in which one or a few amino acids are substituted, deleted, added or inserted in the amino acid sequence shown in SEQ ID NO:66;

(C) a heavy chain variable region containing CDR1 having the amino acid sequence shown in SEQ ID NO:68 or an amino acid sequence in which one or a few amino acids are substituted, deleted, added or inserted in the amino acid sequence shown in SEQ ID NO:68; CDR2 having the amino acid sequence shown in SEQ ID NO:69 or an amino acid sequence in which one or a few amino acids are substituted, deleted, added or inserted in the amino acid sequence shown in SEQ ID NO:69; and CDR3 having the amino acid sequence shown in SEQ ID NO:70 or an amino acid sequence in which one or a few amino acids are substituted, deleted, added or inserted in the amino acid sequence shown in SEQ ID NO:70, and a light chain variable region containing CDR1 having the amino acid sequence shown in SEQ ID NO:72 or an amino acid sequence in which one or a few amino acids are substituted, deleted, added or inserted in the amino acid sequence shown in SEQ ID NO:72; CDR2 having the amino acid sequence shown in SEQ ID NO:73 or an amino acid sequence in which one or a few amino acids are substituted, deleted, added or inserted in the amino acid sequence shown in SEQ ID NO:73; and CDR3 having the amino acid sequence shown in SEQ ID NO:74 or an amino acid sequence in which one or a few amino acids are substituted, deleted, added or inserted in the amino acid sequence shown in SEQ ID NO:74;

(D) a heavy chain variable region containing CDR1 having the amino acid sequence shown in SEQ ID NO:76 or an amino acid sequence in which one or a few amino acids are substituted, deleted, added or inserted in the amino acid sequence shown in SEQ ID NO:76; CDR2 having the amino acid sequence shown in SEQ ID NO:77 or an amino acid sequence in which one or a few amino acids are substituted, deleted, added or inserted in the amino acid sequence shown in SEQ ID NO:77; and CDR3 having the amino acid sequence shown in SEQ ID NO:78 or an amino acid sequence in which one or a few amino acids are substituted, deleted, added or inserted in the amino acid sequence shown in SEQ ID NO:78, and a light chain variable region containing CDR1 having the amino acid sequence shown in SEQ ID NO:80 or an amino acid sequence in which one or a few amino acids are substituted, deleted, added or inserted in the amino acid sequence shown in SEQ ID NO:80; CDR2 having the amino acid sequence shown in SEQ ID NO:81 or an amino acid sequence in which one or a few amino acids are substituted, deleted, added or inserted in the amino acid sequence shown in SEQ ID NO:81; and CDR3 having the amino acid sequence shown in SEQ ID NO:82 or an amino acid sequence in which one or a few amino acids are substituted, deleted, added or inserted in the amino acid sequence shown in SEQ ID NO:82;

(E) a heavy chain variable region containing CDR1 having the amino acid sequence shown in SEQ ID NO:84 or an amino acid sequence in which one or a few amino acids are substituted, deleted, added or inserted in the amino acid sequence shown in SEQ ID NO:84; CDR2 having the amino acid sequence shown in SEQ ID NO:85 or an amino acid sequence in which one or a few amino acids are substituted, deleted, added or inserted in the amino acid sequence shown in SEQ ID NO:85; and CDR3 having the amino acid sequence shown in SEQ ID NO:86 or an amino acid sequence in which one or a few amino acids are substituted, deleted, added or inserted in the amino acid sequence shown in SEQ ID NO:86, and a light chain variable region containing CDR1 having the amino acid sequence shown in SEQ ID NO:88 or an amino acid sequence in which one or a few amino acids are substituted, deleted, added or inserted in the amino acid sequence shown in SEQ ID NO:88; CDR2 having the amino acid sequence shown in SEQ ID NO:89 or an amino acid sequence in which one or a few amino acids are substituted, deleted, added or inserted in the amino acid sequence shown in SEQ ID NO:89; and CDR3 having the amino acid sequence shown in SEQ ID NO:90 or an amino acid sequence in which one or a few amino acids are substituted, deleted, added or inserted in the amino acid sequence shown in SEQ ID NO:90.

Item 2. The anti-semaphorin 3A antibody or antibody fragment thereof according to item 1, wherein the antibody or antibody fragment thereof is a chimeric antibody, a humanized antibody or an antibody fragment thereof.

Item 3. The anti-semaphorin 3A antibody or antibody fragment thereof according to item 1 or 2, wherein the antibody or antibody fragment thereof is used for acceleration of neuronal regeneration.

Item 4. The anti-semaphorin 3A antibody or antibody fragment thereof according to item 1 or 2, wherein the antibody or antibody fragment thereof is used for prophylaxis and/or treatment of Alzheimer's disease.

Item 5. The anti-semaphorin 3A antibody or antibody fragment thereof according to item 1 or 2, wherein the antibody or antibody fragment thereof is used for prophylaxis and/or treatment of sepsis.

Item 6. The anti-semaphorin 3A antibody or antibody fragment thereof according to item 1 or 2, wherein the antibody or antibody fragment thereof is used for prophylaxis and/or treatment of cancer.

Item 7. Use of the anti-semaphorin 3A antibody or antibody fragment thereof according to item 1 or 2 for the manufacture of a prophylactic and/or therapeutic agent of disseminated intravascular coagulation.

Item 8. The anti-semaphorin 3A antibody or antibody fragment thereof according to item 1 or 2, wherein the antibody or antibody fragment thereof is used for prophylaxis and/or treatment of at least one disease selected from the group consisting of central or peripheral nervous system disease, autoimmune disease, inflammatory disease, infectious disease and allergic disease.

Item 9. A pharmaceutical composition comprising the anti-semaphorin 3A antibody or antibody fragment thereof according to any one of items 1 to 8.

Item 10. The pharmaceutical composition according to item 9, wherein the composition is for acceleration of neuronal regeneration.

Item 11. The pharmaceutical composition according to item 9, wherein the composition is for prophylaxis and/or treatment of Alzheimer's disease.

Item 12. The pharmaceutical composition according to item 9, wherein the composition is for prophylaxis and/or treatment of sepsis.

Item 13. The pharmaceutical composition according to item 9, wherein the composition is for prophylaxis and/or treatment of cancer.

Item 14. The pharmaceutical composition according to item 13, wherein cancer is bowel cancer, colorectal cancer, lung cancer, breast cancer, brain cancer, melanoma, renal cell cancer, leukemia, lymphoma, T-cell lymphoma, stomach cancer, pancreatic cancer, cervical cancer, endometrial cancer, ovarian cancer, esophagus cancer, liver cancer, head and neck squamous cell carcinoma, skin cancer, urinary tract cancer, prostate cancer, choriocarcinoma, pharyngeal cancer or larynx cancer.

Item 15. The pharmaceutical composition according to item 9, wherein the composition is for prophylaxis and/or treatment of disseminated intravascularcoagulation.

Item 16. The pharmaceutical composition according to item 15, wherein disseminated intravascular coagulation accompanies at least one selected from the group consisting of sepsis, acute leukemia, solid cancer, premature separation of normally implanted placenta, amniotic fluid embolism, trauma, burn injury, connective tissue disease, shock, aortic aneurysm, acute hepatitis, liver cirrhosis, acute pancreatitis, rhabdomyolysis, thrombosis and severe infectious disease.

Item 17. The pharmaceutical composition according to item 9, wherein the composition is for prophylaxis and/or treatment of at least one disease selected from the group consisting of central or peripheral nervous system disease, autoimmune disease, inflammatory disease, infectious disease and allergic disease.

Item 18. The pharmaceutical composition according to item 17, wherein central or peripheral nervous system disease is neuropathic pain, spinal cord injury or neurodegenerative disease.

Item 19. The pharmaceutical composition according to item 18, wherein neurodegenerative disease is Alzheimer's disease, Parkinson's disease, Huntington's disease, amyotrophic lateral sclerosis, progressive supranuclear palsy, striatonigral degeneration, Shy-Drager syndrome, olivopontocerebellar atrophy or spinocerebellar degeneration.

Item 20. The pharmaceutical composition according to item 17, wherein autoimmune disease is rheumatoid arthritis, type I diabetes mellitus, inflammatory bowel disease, Crohn's disease, systemic lupus erythematosus or multiple sclerosis.

Item 21. The pharmaceutical composition according to item 17, wherein inflammatory disease is sepsis, chronic obstructive pulmonary disease, asthma, arthritis, hepatitis, spondyloarthritis or Sjogren's disease.

Item 22. The pharmaceutical composition according to item 17, wherein infectious disease is bacterial infectious disease, encephalitis, meningitis, endocarditis, hepatitis C, influenza, severe acute respiratory syndrome, pneumonia, sepsis, burn injury- or trauma-induced infectious disease.

Item 23. The pharmaceutical composition according to item 17, wherein allergic disease is allergic rhinitis, allergic conjunctivitis, atopic dermatitis, bronchial asthma or food allergy.

Item 24. A method for neuronal regeneration, comprising administrating the anti-semaphorin 3A antibody or antibody fragment thereof according to item 1 or 2 to a patient in need of neuronal regeneration.

Item 25. A method for treating Alzheimer's disease, comprising administrating the anti-semaphorin 3A antibody or antibody fragment thereof according to item 1 or 2 to a patient with Alzheimer's disease.

Item 26. A method for treating sepsis, comprising administrating the anti-semaphorin 3A antibody or antibody fragment thereof according to item 1 or 2 to a patient with sepsis.

Item 27. A method for treating cancer, comprising administrating the anti-semaphorin 3A antibody or antibody fragment thereof according to item 1 or 2 to a patient with cancer.

Item 28. The treatment method according to item 27, wherein cancer is bowel cancer, colorectal cancer, lung cancer, breast cancer, brain cancer, melanoma, renal cell cancer, leukemia, lymphoma, T-cell lymphoma, stomach cancer, pancreatic cancer, cervical cancer, endometrial cancer, ovarian cancer, esophagus cancer, liver cancer, head and neck squamous cell carcinoma, skin cancer, urinary tract cancer, prostate cancer, choriocarcinoma, pharyngeal cancer or larynx cancer.

Item 29. A method for treating disseminated intravascular coagulation, comprising administrating the anti-semaphorin 3A antibody or antibody fragment thereof according to item 1 or 2 to a patient with disseminated intravascular coagulation.

Item 30. The method for treating disseminated intravascular coagulation according to item 29, wherein the disseminated intravascular coagulation accompanies at least one selected from the group consisting of sepsis, acute leukemia, solid cancer, premature separation of normally implanted placenta, amniotic fluid embolism, trauma, burn injury, connective tissue disease, shock, aortic aneurysm, acute hepatitis, liver cirrhosis, acute pancreatitis, rhabdomyolysis, thrombosis and severe infectious disease.

Item 30. A treatment method comprising administrating the anti-semaphorin 3A antibody or antibody fragment thereof according to item 1 or 2 to a patient with at least one disease selected from the group consisting of central or peripheral nervous system disease, autoimmune disease, inflammatory disease, infectious disease and allergic disease.

Item 31. Use of the anti-semaphorin 3A antibody or antibody fragment thereof according to item 1 or 2 for the manufacture of a medicine for neuronal regeneration.

Item 32. Use of the anti-semaphorin 3A antibody or antibody fragment thereof according to item 1 or 2 for the manufacture of a prophylactic and/or therapeutic agent of Alzheimer's disease.

Item 33. Use of the anti-semaphorin 3A antibody or antibody fragment thereof according to item 1 or 2 for the manufacture of a prophylactic and/or therapeutic agent of sepsis.

Item 34. Use of the anti-semaphorin 3A antibody or antibody fragment thereof according to item 1 or 2 for the manufacture of a prophylactic and/or therapeutic agent of cancer.

Item 35. Use of the anti-semaphorin 3A antibody or antibody fragment thereof according to item 1 or 2 for the manufacture of a prophylactic and/or therapeutic agent of disseminated intravascular coagulation.

Item 36. Use of the anti-semaphorin 3A antibody or antibody fragment thereof according to item 1 or 2 for the manufacture of a prophylactic and/or therapeutic agent of at least one disease selected from the group consisting of central or peripheral nervous system disease, autoimmune disease, inflammatory disease, infectious disease and allergic disease.

Item 37. A method for measuring Sema 3A protein, comprising measuring Sema 3A protein in a sample using immunoassay with the anti-Sema 3A antibody or antibody fragment thereof according to item 1 or 2.

Item 38. A kit for measuring Sema 3A protein containing the anti-Sema 3A antibody or antibody fragment thereof according to item 1 or 2.

Advantages of the Invention

The anti-Sema 3A antibody of the present invention can effectively prevent and/or treat neurodegenerative diseases such as Alzheimer's disease, etc. and significantly ameliorate symptoms associated with the neurodegenerative disease. Without wishing to be bound by limited interpretation for any action mechanism of the anti-Sema 3A antibody of the present invention, there is believed that the anti-Sema 3A antibody of the present invention effectively inhibits a function of Sema 3A protein, thereby to block signaling of Sema 3A, resulting in reduction of accumulation of phosphorylated collapsin response mediator protein (CRMP) in neurofibrillary tangle. The anti-Sema 3A antibody of the present invention is also effective for prophylaxis and/or treatment of central or peripheral nervous system disease other than neurodegenerative disease, autoimmune disease, inflammatory disease, infectious disease and allergic disease, etc. and in particular, can exhibit prominent effects of prophylaxis and/or treatment of inflammatory disease such as sepsis, which is caused by collapsing immunity mechanism due to infection or potent inflammation-inducing stimulus. The anti-Sema 3A antibody of the present invention can effectively suppress migration/invasion activities of cancer cells induced by Sema 3A and remove anticancer drug-unresponsiveness induced by Sema 3A to recover drug sensitivity, and therefore is also effective for prophylaxis and/or treatment of cancer. Furthermore, the anti-Sema 3A antibody of the present invention has the action of suppressing increase of blood level of PAI-1 and therefore, is also effective for prophylaxis and/or treatment of disseminated intravascular coagulation.

The anti-Sema 3A antibody of the present invention can be used in measurement of Sema 3A protein. In particular, the use of the anti-Sema 3A antibody of the present invention allows to measure Sema 3A protein even in the presence of serum in a high accurate manner and therefore measure Sema 3A protein in a biological sample.

BRIEF DESCRIPTION OF THE DRAWINGS

FIG. 9 shows results of collapse assay with chicken-derived Sema 3A protein and anti-Sema 3A avian-mouse chimeric antibody.

FIG. 10 shows results of collapse assay with chicken-derived Sema 3A protein and anti-Sema 3A avian antibody.

FIG. 11 shows results of collapse assay with chicken-derived Sema 3A protein and anti-Sema 3A avian-mouse chimeric antibody.

FIG. 15A shows a graph illustrating results of access rate to Object B in acquisition trials of novel object recognition task. FIG. 15B shows a graph illustrating results of access rate to Object C in test trials of novel object recognition task.

EMBODIMENTS OF THE INVENTION

Figure 1:
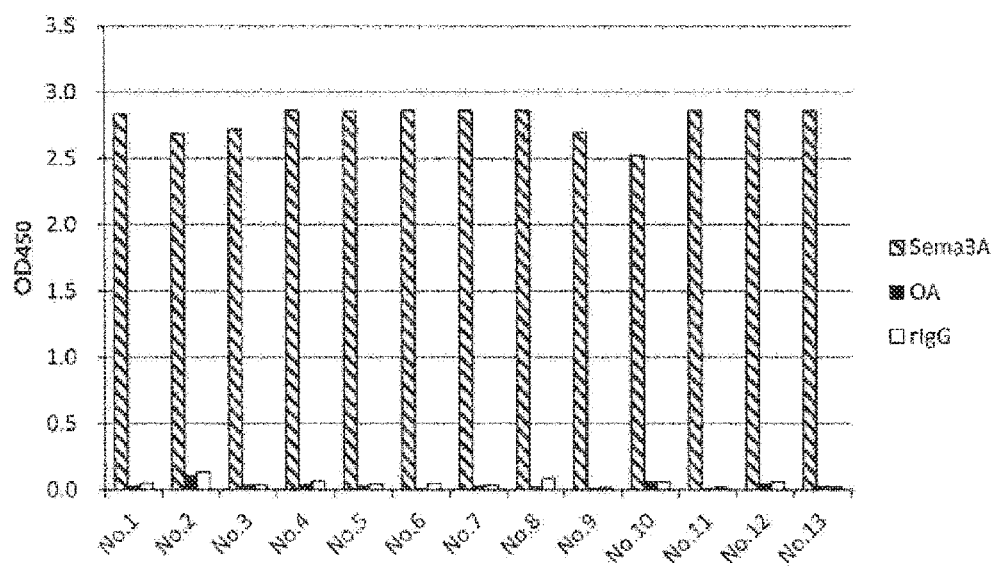
FIG. 1 shows a graph illustrating 13 anti-Sema 3A antibody-producing clones prepared in Example 1.

1. Anti-Sema 3A Antibody and Antibody Fragment Thereof

The anti-Sema 3A antibody of the present invention is characterized by inclusion of a heavy chain variable region containing CDR1 to CDR3 having specific amino acid sequences and a light chain variable region containing CDR1 to CDR3 having specific amino acid sequences.

The anti-Sema 3A antibody of the present invention can specifically bind to Sema 3A protein and effectively inhibit a function of the protein. Sema 3A protein is an endogenous protein which is encoded by a gene belonging to class III semaphorin subfamily and identified as a factor that collapses nerve growth cone thereby to suppress axon elongation. The amino acid sequence of Sema 3A protein is known (GenBank accession number; NP_006071.1 for human-derived, NP_033178.2 for mouse-derived).

Preferred examples of an aspect of the anti-Sema 3A antibody of the present invention include a heavy chain variable region and a light chain variable region shown in the following items (A) to (E);

(A) a heavy chain variable region containing CDR1 having the amino acid sequence shown in SEQ ID NO:1, CDR2 having the amino acid sequence shown in SEQ ID NO:2 and CDR3 having the amino acid sequence shown in SEQ ID NO:3 and a light chain variable region containing CDR1 having the amino acid sequence shown in SEQ ID NO:4, CDR2 having the amino acid sequence shown in SEQ ID NO:5 and CDR3 having the amino acid sequence shown in SEQ ID NO:6.

(B) a heavy chain variable region containing CDR1 having the amino acid sequence shown in SEQ ID NO:60, CDR2 having the amino acid sequence shown in SEQ ID NO:61 and CDR3 having the amino acid sequence shown in SEQ ID NO:62 and a light chain variable region containing CDR1 having the amino acid sequence shown in SEQ ID NO:64, CDR2 having the amino acid sequence shown in SEQ ID NO:65 and CDR3 having the amino acid sequence shown in SEQ ID NO:66, (C) a heavy chain variable region containing CDR1 having the amino acid sequence shown in SEQ ID NO:68, CDR2 having the amino acid sequence shown in SEQ ID NO:69 and CDR3 having the amino acid sequence shown in SEQ ID NO:70 and a light chain variable region containing CDR1 having the amino acid sequence shown in SEQ ID NO:72, CDR2 having the amino acid sequence shown in SEQ ID NO:73 and CDR3 having the amino acid sequence shown in SEQ ID NO:74, (D) a heavy chain variable region containing CDR1 having the amino acid sequence shown in SEQ ID NO:76, CDR2 having the amino acid sequence shown in SEQ ID NO:77 and CDR3 having the amino acid sequence shown in SEQ ID NO:78 and a light chain variable region containing CDR1 having the amino acid sequence shown in SEQ ID NO:80, CDR2 having the amino acid sequence shown in SEQ ID NO:81 and CDR3 having the amino acid sequence shown in SEQ ID NO:82, (E) a heavy chain variable region containing CDR1 having the amino acid sequence shown in SEQ ID NO:84, CDR2 having the amino acid sequence shown in SEQ ID NO:85 and CDR3 having the amino acid sequence shown in SEQ ID NO:86 and a light chain variable region containing CDR1 having the amino acid sequence shown in SEQ ID NO:88, CDR2 having the amino acid sequence shown in SEQ ID NO:89 and CDR3 having the amino acid sequence shown in SEQ ID NO:90.

In the anti-Sema 3A antibody of the present invention, amino acid sequences of CDRs 1 to 3 in a heavy chain and a light chain (SEQ ID NOs: 1-6, 60-62, 64-66, 68-70, 72-74, 76-78, 80-82, 84-86 and 88-90) may be those in which one or a few amino acids are substituted, deleted, added and/or inserted. Anti-Sema 3A antibody containing CDR sequences in which one or a few amino acids are substituted, deleted, added and/or inserted has desirably a binding activity to Sema 3A protein equal to or more than that of anti-Sema 3A antibody containing unmodified CDR sequences. The number of amino acids substituted, deleted, added and/or inserted preferably includes but are not particularly limited to 1 to 3, more preferably 1 to 2, particularly preferably 1 per CDR. In amino acid sequences of CDRs 1 to 3 in a heavy chain and a light chain of the anti-Sema 3A antibody of the present invention, amino acids may be substituted, deleted, added and/or inserted in one amino acid sequence and may be substituted, deleted, added and/or inserted in two or more amino acid sequences.

In substitution of an amino acid in the amino acid sequence of CDR, a substitution by the corresponding amino acid (i.e. conservative amino acid substitution) is preferred since the binding activity of antibody is expected not to change through the substitution. In particular, the following category is established based on properties of amino acid side chains:

Basic amino acid: lysine, arginine and histidine,
Acidic amino acid: glutamic acid and aspartic acid,
Neutral amino acid: glycine, alanine, serine, threonine, methionine, cysteine, phenylalanine, tryptophan, tyrosine, leucine, isoleucine, valine, glutamine, asparagine and proline.

Furthermore, the neutral amino acid described above can be categorized into one having a polar side chain (asparagine, glutamine, serine, threonine, tyrosine and cysteine), one having a non-polar side chain (glycine, alanine, valine, leucine, isoleucine, proline, phenylalanine, methionine and tryptophan), one having an amide-containing side chain (asparagine and glutamine), one having a sulfur-containing side chain (methionine and cysteine), one having an aromatic side chain (phenylalanine, tryptophan and tyrosine), one having a hydroxyl-containing side chain (serine, threonine and tyrosine) and one having an aliphatic side chain (alanine, leucine, isoleucine and valine), etc.

A method of substitution of one or several amino acid residues to other target desired amino acids include, for example, site-directed mutagenesis (Hashimoto-Gotoh T. et al., Gene, Vol. 152, p. 271-275 (1995); Zoller M J. et al., Methods Enzymol. Vol. 100, p. 468-500 (1983), Kramer W. et al., Nucleic Acids Res. Vol. 12, p. 9441-9456 (1984); Kramer W. et al., Methods. Enzymol. Vol. 154, p. 350-367 (1987); Kunkel T A., Proc Natl Acad Sci USA., Vol. 82, p. 488-492 (1985) and others), and the use of such site-directed mutagenesis allows to perform amino acid substitution in the amino acid sequence of CDR. Other method of substitution to other amino acid include a library technique described in WO2005/080432.

In the anti-Sema 3A antibody of the present invention, amino acid sequences in the framework region of variable region and in the constant region are not particularly limited unless the amino acid sequences substantially affect the binding activity to Sema 3A protein.

Amino acid sequences of CDRs 1 to 3 (SEQ ID NOs: 1-6, 60-62, 64-66, 68-70, 72-74, 76-78, 80-82, 84-86 and 88-90) are derived from an avian antibody, and the anti-Sema 3A antibody of the present invention may be an avian antibody, preferably a chimeric antibody and a humanized antibody.

A chimeric antibody is an antibody in which regions having different origins are conjugated with each other. In the case where a chimeric antibody is used as the anti-Sema 3A antibody of the present invention, as pharmaceutical compositions and therapeutic agents of various diseases, used is desirably an avian-human chimeric antibody which is composed of an avian antibody-derived variable region and a human antibody-derived constant region or an avian-mouse chimeric antibody which is composed of an avian antibody-derived variable region and a mouse antibody-derived constant region, more preferably an avian-human chimeric antibody. In the case where a chimeric antibody is used in immunoassay of and a kit for measurement of Sema 3A protein, an avian-human chimeric antibody and an avian-mouse chimeric antibody can be used and added to which is also an avian-rabbit chimeric antibody which is composed of an avian antibody-derived variable region and a rabbit antibody-derived constant region and an avian-goat chimeric antibody which is composed of an avian antibody-derived variable region and a goat antibody-derived constant region. Amino acid sequences shown in SEQ ID NOs: 7, 8, 59, 67, 75 and 83 are exemplified as examples of an amino acid sequence of the heavy chain variable region used for an avian-human chimeric antibody, an avian-mouse chimeric antibody, an avian-rabbit chimeric antibody or an avian-rabbit chimeric antibody. Amino acid sequences shown in SEQ ID NOs: 9, 10, 63, 71, 79 and 87 are also exemplified as examples of an amino acid sequence of the light chain variable region used for an avian-human chimeric antibody, an avian-mouse chimeric antibody, an avian-rabbit chimeric antibody or an avian-rabbit chimeric antibody. When these amino acid sequences of variable regions (SEQ ID NOs: 7 to 10, 59, 63, 67, 71, 75, 79, 83 and 87) each have a binding activity to Sema 3A protein equal to or greater than that of an unmodified amino acid sequence, one or several amino acids may be substituted, deleted, added and/or inserted. The number of amino acids substituted, deleted, added and/or inserted is not particularly limited, and for example, 1 to 21, preferably 1 to 14, more preferably 1 to 3 in the heavy chain variable region (SEQ ID NOs: 7, 8, 59, 67, 75, 83) and/or the light chain variable region (SEQ ID NOs: 9, 10, 63, 71, 79, 87). Note that in the heavy chain variable region (SEQ ID NOs: 7, 8, 59, 67, 75, 83) and/or the light chain variable region (SEQ ID NOs: 9, 10, 63, 71, 79, 87), amino acids are desirably substituted, deleted, added and/or inserted in other region except amino acid sequences of CDRs 1 to 3. In amino acid sequences of the heavy chain and light chain variable regions, the substitution of amino acids is desirably conservative amino acid substitution as described above.

A humanized antibody is one in which a non-human derived CDR sequence is grafted on a framework region of a human antibody and one which contains a non-human antibody-derived CDR sequence, a human antibody-derived framework region and a human antibody-derived constant region. A humanized antibody has a decreased antigenicity in the human body and therefore, is suitable for pharmaceutical applications of the anti-Sema 3A antibody of the present invention. The amino acid sequence shown in SEQ ID NO: 11 is exemplified as an example of amino acid sequences of the heavy chain variable region used for a humanized antibody. Also, the amino acid sequences shown in SEQ ID NOs: 12 and 13 is exemplified as examples of amino acid sequences of the light chain variable region used for a humanized antibody. When these amino acid sequences of variable regions (SEQ ID NOs: 11 to 13) each has a binding activity to Sema 3A protein equal to that of unmodified amino acid sequences, one or several amino acids may be substituted, deleted, added and/or inserted. The number of amino acids substituted, deleted, added and/or inserted is not particularly limited, and is, for example, 1 to 21, preferably 1 to 14, more preferably 1 to 3 in the heavy chain variable region (SEQ ID NO: 11) and/or the light chain variable region (SEQ ID NOs: 12 and 13). Note that in the heavy chain variable region (SEQ ID NO: 11) and/or the light chain variable region (SEQ ID NOs: 12 and 13), amino acids are desirably substituted, deleted, added and/or inserted in other region except amino acid sequences of CDRs 1 to 3. In amino acid sequences in a heavy chain and light chain variable regions, the substitution of amino acids is desirably a conservative amino acid substitution as described above.

A chimeric antibody can be produced, for example, by substituting an avian antibody-constant region containing the heavy chain variable region and light chain variable region having each of amino acid sequences of CDRs 1 to 3 with a human antibody-constant region (e.g. Morrison et al., Proc. Natl. Acad. Sci., Vol. 81, p. 6851-6855 (1984); Neuberger et al., Nature, Vol. 312, p. 604-608 (1984); Takeda et al., Nature, Vol. 314, p. 452-454 (1985) and others). Nucleotide sequences of DNA encoding SEQ ID NOs: 7, 8, 59, 67, 75 and 83, amino acid sequences in the heavy chain variable region used for an avian-human chimeric antibody are shown in SEQ ID NOs: 14, 15, 103, 111, 119 and 127, respectively. Nucleotide sequences of DNA encoding SEQ ID NOs: 9, 10, 63, 71, 79 and 87, amino acid sequences in the light chain variable region used for an avian-human chimeric antibody are shown in SEQ ID NOs: 16, 17, 104, 112, 120 and 128, respectively. Known amino acid sequences can be used in the human antibody-constant region. In particular, an avian-human chimeric antibody can be produced by the following process.

Firstly, DNA encoding an avian heavy chain variable region containing a CDR having a given amino acid sequence is produced through chemical synthesis, biochemical cleavage, reconjugation and the like. The obtained heavy chain variable region-encoding DNA is ligated with human heavy chain constant region-encoding DNA, which then is incorporated to a vector for expression to produce a heavy chain expression vector. A light chain expression vector is produced in the same manner as described above. The obtained heavy chain expression vector and light chain expression vector are used to cotransform a host cell such as HEK293 cell line, CHO cells, SP2/0 cells, etc. The transformant is cultivated, followed by separation of target chimeric antibody from the transformant culture solution. Alternatively, amino acids of a framework region in the antibody variable region may be substituted so that a CDR of an avian-human chimeric antibody forms a suitable antigen-biding site (Sato, K. et al., Cancer Research, Vol. 53, p. 851-856 (1993)).

A humanized antibody can be produced, for example, by grafting CDRs 1 to 3 containing the amino acid sequences on a framework region of a human antibody (e.g. Jones et al., Nature, Vol. 321, p. 522-525 (1986); Riechmann et al., Nature, Vol. 332, p. 323-327 (1988); Verhoeyen et al., Science, Vol. 239, p. 1534-1536 (1988)). Nucleotide sequences of DNA encoding heavy chain CDR 1 (SEQ ID NOs: 1, 60, 68, 76 and 84) are shown in SEQ ID NOs: 18, 97, 105, 113 and 121, respectively. Nucleotide sequences of DNA encoding heavy chain CDR 2 (SEQ ID NOs: 2, 61, 69, 77 and 85) are shown in SEQ ID NOs: 19, 98, 106, 114 and 122, respectively. Nucleotide sequences of DNA encoding heavy chain CDR 3 (SEQ ID NOs: 3, 62, 70, 78 and 86) are shown in SEQ ID NOs: 20, 99, 107, 115 and 123, respectively. Nucleotide sequences of DNA encoding light chain CDR 1 (SEQ ID NOs: 4, 64, 72, 80 and 88) are shown in SEQ ID NOs: 21, 100, 108, 116 and 124, respectively. Nucleotide sequences of DNA encoding light chain CDR 2 (SEQ ID NOs: 5, 65, 73, 81 and 89) are shown in SEQ ID NOs: 22, 101, 109, 117 and 125, respectively. Nucleotide sequences of DNA encoding light chain CDR 3 (SEQ ID NOs: 6, 66, 74, 82 and 90) are shown in SEQ ID NOs: 23, 102, 110, 118 and 126, respectively. In particular, a humanized antibody can be produced by the following process.

A humanized antibody can be produced by treating CDRs 1 to 3 having given amino acid sequences and heavy chain variable region-encoding DNA ligated with four framework regions derived from human antibodies in a given order through chemical synthesis, biochemical cleavage, reconjugation, etc. Here, amino acids of the framework regions may be mutated by substitution, deletion and/or addition, etc. so that the CDRs of humanized antibody form suitable antigen-biding sites (Sato, K. et al., Cancer Research, Vol. 53, p. 851-856 (1993)). The obtained heavy chain variable region-encoding DNA is ligated with a human heavy chain constant region-encoding DNA, which then is incorporated to a vector for expression to produce a heavy chain expression vector. A light chain expression vector is produced in the same manner as described above. The obtained heavy chain expression vector and light chain expression vector are used to cotransform host cells such as FreeStyle 293 cell line (Life Technologies), CHO cells, SP2/0 cells, etc. The transformant is cultivated, followed by separation of target humanized antibody from the transformant culture solution. A nucleotide sequence of DNA encoding the amino acid sequence, SEQ ID NO: 11 in the heavy chain variable region used for a humanized antibody is shown in SEQ ID NO: 24. Nucleotide sequences of DNA encoding the amino acid sequences, SEQ ID NOs: 12 and 13 in the light chain variable region used for a humanized antibody is shown in SEQ ID NOs: 25 and 26. Known amino acid sequences can be used in a human antibody-constant region.

Isotypes of the anti-Sema 3A antibody of the present invention are not particularly limited and examples thereof include IgG (IgG1, $IgG_2$, $IgG_3$ and $IgG_4$), IgA ($IgA_1$ and $IgA_2$), IgM, IgD and IgE, for example. Among them, IgG is preferred.

In the present invention, an antibody fragment can be also used as far as the antigen binding region of anti-Sema 3A antibody is contained therein. Examples of antibody fragments include Fab, Fab', $F(ab')_2$, scFv, dsFv, etc. These antibody fragments can be produced according to the conventional methods.

The anti-Sema 3A antibody or antibody fragment thereof of the present invention may be an antibody or its antibody fragment conjugated with various compounds such as polyethylene glycol, a radioactive substance, toxin, etc. The anti-Sema 3A antibody or antibody fragment thereof of the present invention may be treated by modifying a bound sugar chain or fusing with other proteins, as necessary.

2. Pharmaceutical Composition

The present invention provides a pharmaceutical composition containing anti-Sema 3A antibody or its antibody fragment. The pharmaceutical composition of the present invention can effectively inhibit a function of Sema 3A protein and achieve various drug efficacy by containing anti-Sema 3A antibody or its antibody fragment.

In the pharmaceutical composition of the present invention, anti-Sema 3A antibody or its antibody fragment, which is contained as an active component, may be in any form of the aspects (A) to (E), and preferred is the anti-Sema 3A antibody or antibody fragment thereof of the aspect (A) in order to effectively inhibit a function of Sema 3A protein and achieve prominent drug efficacy.

The pharmaceutical composition of the present invention may simply contain an effective amount of the anti-Sema 3A antibody or its antibody fragment and otherwise may contain a pharmaceutically acceptable carrier or additive. Examples of such a carrier or an addictive include a surfactant, an excipient, a colorant, a flavorincagent, a preservative, a stabilizer, a buffer, a pH buffer, a disintegrant, a solubilizer, a solubilizing aid, a tonicity agent, a binder, a disintegrant, a lubricant, a diluent, a corrigent, etc, for example. The carrier or addictive is not limited to them and other carriers or additives commonly used in pharmaceutical compositions can be also used, as applicable.

An administration form of the pharmaceutical composition of the present invention may be in either oral or parenteral form, and particular examples thereof include oral administration; and parenteral administration such as intravenous, intramuscular, intraperitoneal, subcutaneous, transnasal, pulmonary, dermal, transmucosal, intraocular administrations, etc.

A formulation of the pharmaceutical composition of the present invention can be appropriately set depending on the administration form to be adopted. For example, in the case of oral administration, the composition may be prepared in the formulation of a powder, a granule, a capsule, a syrup, a suspension, etc., and in the case of parenteral administration, the composition may be prepared in the formulation of a liquid, a suspension, an emulsion, a spray, a suppository, an eye drop, etc.

The pharmaceutical composition of the present invention can effectively inhibit a function of Sema 3A protein by the action of anti-Sema 3A antibody or its antibody fragment and therefore is useful for prophylaxis and/or treatment of diseases involving Sema 3A protein. Examples of diseases involving Sema 3A protein include, for example, central or peripheral nervous system disease, autoimmune disease, inflammatory disease, infectious disease, allergic disease and cancer, etc. Particular examples of central or peripheral nervous system disease include neuropathic pain, spinal cord injury, and neurodegenerative disease (e.g. Alzheimer's disease, Parkinson's disease, Huntington's disease, amyotrophic lateral sclerosis, progressive supranuclearpalsy, striatonigral degeneration, Shy-Drager syndrome, olivopontocerebellar atrophy and spinocerebellar degeneration, etc.). Particular examples of autoimmune disease include rheumatoid arthritis, type I diabetes mellitus, inflammatory bowel disease, Crohn's disease, systemic lupus erythematosus, multiple sclerosis, etc. Particular examples of inflammatory disease include sepsis, chronic obstructive pulmonary disease, asthma, arthritis, hepatitis, spondyloarthritis, Sjogren's syndrome, etc. Particular examples of infectious disease include bacterial infectious disease, encephalitis/meningitis, endocarditis, hepatitis C, influenza/severe acute respiratory syndrome (SARS), pneumonia, sepsis, burn injury, trauma infectious disease, etc. Particular examples of allergic disease include allergic rhinitis, allergic conjunctivitis, atopic dermatitis, bronchial asthma, food allergy, etc. Particular examples of cancer include bowel cancer, colorectal cancer, lung cancer, breast cancer, brain cancer, melanoma, renal cell cancer, leukemia, lymphoma, T-cell lymphoma, stomach cancer, pancreatic cancer, cervical cancer, endometrial cancer, ovarian cancer, esophagus cancer, liver cancer, head and neck squamous cell carcinoma, skin cancer, urinary tract cancer, prostate cancer, choriocarcinoma, pharyngeal cancer, larynx cancer, etc.

Anti-Sema 3A antibody or its antibody fragment can effectively suppress neuronal regeneration-inhibitory ability of Sema 3A protein to accelerate regeneration and elongation of nerves and therefore the pharmaceutical composition of the present invention is useful as a pharmaceutical composition for regenerating and elongating nerves (i.e. pharmaceutical composition for neuronal regeneration and elongation). The pharmaceutical composition of the present invention also allows to regenerate and elongate nerves themselves by anti-Sema 3A antibody or its antibody fragment and therefore, is specifically useful as a pharmaceutical composition for prophylaxis and/or treatment of neurodegenerative disease.

Furthermore, anti-Sema 3A antibody or its antibody fragment exhibits prominent effects of prophylaxis and/or treatment of inflammatory disease containing sepsis, other disease associated with cytokine storm, such as graft versus host disease (GVHD), acute respiratory distress syndrome (ARDS), avian influenza, smallpox, systemic inflammatory response syndrome (SIRS), drug-induced cytokine storm, etc. which are caused by collapsing immunity mechanism due to infection or potent inflammation-inducing stimulus and therefore the antibody or its antibody fragment is highly useful as a pharmaceutical composition for prophylaxis and/or treatment of these diseases.

Anti-Sema 3A antibody or its antibody fragment can effectively suppress migration/invasion activities of cancer cells induced by Sema 3A and exhibits prominent effects of prophylaxis and/or treatment of diseases associated with exacerbation/progression of cancer and therefore, is highly useful as a pharmaceutical composition for prophylaxis and/or treatment of cancerous diseases. When the pharmaceutical composition of the present invention is used for applications of prophylaxis and/or treatment of cancer, other anticancer drug may be used in combination. Anti-Sema 3A antibody or its antibody fragment can specifically remove anticancer drug-unresponsiveness of cancer cells induced by Sema 3A to recover drug sensitivity, and therefore exhibit prominent effects of prophylaxis and/or treatment of cancer in combination with other anticancer drugs. In the case of combined use of anti-Sema 3A antibody or its antibody fragment with other anticancer drug, anti-Sema 3A antibody or its antibody fragment and other anticancer drug may be prepared in single pharmaceutical composition for formulation and anti-Sema 3A antibody or its antibody fragment and other anticancer drug may be prepared in different pharmaceutical compositions for formulation.

The pharmaceutical composition of the present invention can suppress increase of blood level of PAI-1 by the action of anti-Sema 3A antibody or its antibody fragment and therefore, is also effective for prophylaxis and/or treatment of disseminated intravascular coagulation. Examples of underlying diseases associated with disseminated intravascular coagulation include sepsis, acute leukemia, solid cancer, premature separation of normally implanted placenta, amniotic fluid embolism, trauma, burn injury, connective tissue disease, shock, aortic aneurysm, acute hepatitis, liver cirrhosis, acute pancreatitis, thrombosis, severe infectious disease, etc.

Dosage and frequency of the pharmaceutical composition of the present invention varies depending on administration method, age and body weight of the patient, types of disease and degrees of symptom severity, etc. and therefore, cannot be uniformly defined. However, neuronal regeneration commonly requires from a few days to a few months or more and therefore, the composition is preferably administered at the necessary frequency to suppress semaphorin activity during neuronal regeneration process. For example, the composition can be administered at the corresponding amount to 0.1 mg to 1000 mg, preferably 1 mg to 500 mg by weight of anti-Sema 3A antibody or its antibody fragment per a dose at once per about 1 to 30 days. Note that the composition can be also administered in the form of a sustained release agent or portionwise over a long period through an osmotic pump in order to reduce frequency of administration. In all of these administration methods, preferably used is an administration route and an administration method where the composition has a concentration which allows to sufficiently inhibit Sema 3A protein activity at the action site.

3. Measurement Method and Measurement Kit of Sema 3A Protein

The present invention provides a measurement method of Sema 3A protein using anti-Sema 3A antibody or its antibody fragment. The measurement method of the present invention immunologically measures Sema 3A in a sample through antigen-antibody reaction of anti-Sema 3A antibody or its antibody fragment with Sema 3A in the sample.

In the measurement method of the present invention, anti-Sema 3A antibody or its antibody fragment reactive with Sema 3A in a sample may be any of the aspects (A) to (E) and the anti-Sema 3A antibody or antibody fragment thereof of the aspect (A) is preferably mentioned in order to measure Sema 3A protein in a higher accurate manner.

A sample is not particularly limited as far as the measurement of Sema 3A is required, and examples thereof include, for example, biological samples such as blood, serum, plasma, urine, spinal fluid, joint fluid, lymph fluid, amnion fluid, breast fluid, various tissue fluids, hippocampus extract and various tissue extracts, etc.

For the measurement method of the present invention, any immunoassay containing sandwich method, competitive method, coagulation method, etc., may be adopted. In the case where sandwich method, which uses a capture antibody trapping an antigen and a primary antibody binding to the antigen conjugated with the capture antibody, is adopted as the measurement method of the present invention, the capture antibody can be any one selected from the anti-Sema 3A antibody or antibody fragment thereof in the aspects (A) to (E), and the different one in the aspects (A) to (E) from the selected capture antibody can be used as the primary antibody. In the case where Sandwich method is adopted, there are particularly preferred that the anti-Sema 3A antibody or antibody fragment thereof in the aspect (A) is used as the capture antibody and the anti-Sema 3A antibody or antibody fragment thereof in the aspect (B) or (C) is used as a primary antibody since Sema 3A protein can be measured particularly in the presence of serum in a higher accurate manner.

Immunoassay includes enzyme-linked immunosorbent assay (ELISA), fluorescent immunoassay, radioimmunoassay depending on marker types, and any of these methods can be used for the measurement method of the present invention. Enzyme-linked immunosorbent assay is preferably mentioned in the light of simpleness and promptness of measurement.

Immunoassay using antigen-antibody reaction is known per se and the measurement method of the present invention can be carried out by any known approach depending on measuring mechanisms and marker types of immunoassay.

The present invention also provides a measurement kit used in the measurement method. The measurement kit of the present invention includes anti-Sema 3A antibody or its antibody fragment.

The measurement kit of the present invention may contain other reagents and instruments together with anti-Sema 3A antibody or its antibody fragment depending on measuring mechanisms and marker types for immunoassay. For example, in the case where enzyme-linked immunosorbent assay is selected, the kit may contain a measuring plate, a chromogenic substrate solution, a quenching solution, a washing solution, a standard sample, etc. together with anti-Sema 3A antibody or its antibody fragment. In the case where sandwich method is adopted, anti-Sema 3A antibody or its antibody fragment used as a capture antibody can be provided in the state immobilized in a solid phase.

EXAMPLES

The present invention is described with reference to Examples in detail below, however, it should be construed that the present invention is not limited to these examples.

Example 1: Preparation of Anti-Sema 3A Antibody (Avian Antibody and Avian-Mouse Chimeric Antibody)

1) Cell Culture

Cell culture of DT40 cells derived from chicken B cells was carried out according to the following process. A $CO_2$ thermostat is used as an incubator, in which culturing was carried out in the presence of 5% $CO_2$ at 39.5° C. IMDM medium (Life Technologies) is used, to which were added 10 vol % FBS, 1 vol % chicken serum, 100 units/mL of penicillin, 100 µg/mL of streptomycin and 55 µM 2-mercaptoethanol for use herein. Trichostatin A (Wako Pure Chemical Industries, Ltd.) was dissolved in DMSO to 5 mg/mL to prepare a stock solution and the stock solution was appropriately diluted in the medium to the final concentration of 1.25 ng/mL or 2.5 ng/mL before use.

2) Isolation of Anti-Sema 3A Antibody-Producing Cells

Mouse Sema 3A protein was produced from mouse Sema 3A protein expressing cell possessed by Molecular Pharmacology and Neurobiology, Yokohama City University Graduate School of Medicine, which protein was used as an antigen to isolate antibody-producing cells using Autonomously Diversifying Library (ADLib) system (Chiome Bioscience, Inc.). In particular, the following experimental process was carried out.

2-1) Preparation of Magnetic Beads with Immobilized Antigen

Immobilization of mouse Sema 3A protein to magnetic beads for His-tag was carried out according to the following process. Dynabeads TALON (Life Technologies) was used as magnetic beads and Dynal MPC (Life Technologies) was used as a magnetic stand.

Beads (22.5 µL) was washed with 45 µL of PBS buffer three times, which then reacted with 6.1 µg of mouse Sema 3A protein in PBS buffer at 4° C. for 10 minutes while stirring in rotating manner. Subsequently, the beads conjugated with mouse Sema 3A protein was washed four times with 45 µL of buffer C (PBS buffer containing 0.1% BSA) and then suspended in 45 µL of buffer C.

2-2) Selection of Antibody-Producing Clone Through Magnetic Beads with Immobilized Antigen Wild-type DT40 cells were cultivated for 5 weeks or more in IMDM medium containing 1.25 ng/mL or 2.5 ng/mL of trichostatin A and $8 \times 10^8$ of the cultivated cells were divided into 8 portions by $1 \times 10^8$ cells each, each of which was washed one time with 10 mL of washing solution (PBS buffer containing 1 wt % BSA), followed by washing one time in 1 mL of the same washing solution and then mixed with $5 \times 10^6$ of the magnetic beads with immobilized antigen prepared in 2-1) in 1 mL of washing solution. Then the mixture was incubated at 4° C. for 30 minutes while gently rotating and subsequently washed three times with 1.7 mL of washing solution for 3 minutes using Kingfisher mL (Thermo Fisher Scientific K.K.). Finally, the cells associated with magnetic beads with immobilized antigen were suspended in 500 µL of medium, which was added to 20 mL of medium and then dispensed into a 96 well plate by 200 µL each and incubated at 39.5° C. In the following process, IMDM medium (Life Technologies) containing 10 vol % FBS, 100 units/mL of penicillin, 100 µg/mL of streptomycin and 55 µM 2-mercaptoethanol was used as a cultivation medium.

2-3) Screening of Anti-Sema 3A Antibody-Producing Clone

A direct solid phase ELISA was carried out according to the following process. In Day 6 after the step 2-2), 2.5 µg/mL of mouse Sema 3A protein was dispensed into a 384 well Maxisorp (Nunc) by 20 µL each and left to stand overnight. Ovalbumin (OA) and rabbit IgG (rIgG) were immobilized in the plate as negative controls in similar manner in order to examine the specificity of antibodies. On the next day, the content in the plate was removed and 45 µL of blocking solution (PBS buffer containing 1% BSA) was added thereto, followed by incubation at room temperature for one hour. The plate was washed five times with 120 µL/well of ELISA washing buffer (PBS containing 0.05 wt % Tween 20), to which were added culture supernatants derived from the colony obtained by selection in the step 2-2) by 25 µL/well and then incubated at room temperature for one hour. The plate was washed five times with 120 µL/well of ELISA washing solution and then to which was added 25 µL of diluent in which a secondary antibody was diluted 2000 times with a blocking buffer and incubated at room temperature for 45 minutes. Anti-chicken IgM-HRP (Bethyl Laboratories, Inc.) was used as a secondary antibody. The each well was washed five times with 120 µL of ELISA washing buffer, to which was added 25 µL of TMB+ (Dako) and incubated for 30 minutes. Subsequently, the reaction was quenched with 25 µL of 1N sulfuric acid to determine the absorbance at 450 nm.

Consequently, thirteen cell strains exhibiting positive for anti-Sema 3A antibody production through direct solid phase ELISA were obtained through the selection by direct association with magnetic beads with immobilized antigen, as shown in FIG. 1.

Among the positive strains obtained, cloning of cell strains No. 4 and No. 6 for antibody producing cells was carried out by limiting dilution, according to the following process.

Each of both strains was prepared to $1 \times 10^3$ cells/mL, 150 µL of which was added to 60 mL of medium and the suspension was seeded in three 96 well plates (Thermo Fisher Scientific K.K.) in an amount of 200 µL/well, followed by stationary culturing for 7 days. Twenty clones from the strains, which was observed to form cell colonies, were subjected to screening of mouse Sema 3A antibody producing clones according to the method described in the step 2-3). Clones exhibiting positive for mouse Sema 3A antibody production were selected by 2 clones each from the strains and then subjected to high-density cell culture.

In high-density cell culture, clones were subjected to extended culture and amplified to $4 \times 10^7$ cells. Clones were observed to be amplified to enough cell counts and the clones were cultivated with CELLine CL-1000 (BD biosciences) in AIM-V medium containing 20 vol % chicken serum component (Life Technologies). A chicken serum component is a chicken serum in which antibodies were removed. The preparation process comprised removing immunoglobulin as a precipitate with 50% saturated ammonium sulfate from chicken serum (Life Technologies), dialyzing the supernatant with PBS buffer, and concentrating the supernatant using a Centri Prep (Amicon) to adjust the increased volume caused by dialyzing. After culturing for about 96 hours, culturing was continued until a survival rate of cells was 50% or less while measuring the survival rate. As the survival rate decreased to 50% or less, the culture supernatant was harvested.

3) Preparation of Culture Supernatant for ELISA

Culture supernatant for analyzing a titer by ELISA was prepared as the following process. in order to remove serum-derived IgM, etc. A chicken serum component was added to AIM-V serum-free medium (Life Technologies) at a concentration of 3%. Cells were added to the prepared medium at a concentration of $1\times10^6$ cells/mL and cultivated for 2 days to obtain culture supernatant.

4) Selection of Anti-Sema 3A Antibody-Producing Clones

The culture supernatant for ELISA obtained in the step 3) was subjected to ELISA to measure a concentration of anti-Sema 3A antibody and thereby to obtain clone No. 4-2 strain having high anti-Sema 3A antibody production ability.

5) Preparation of Culture Supernatant Containing Anti-Sema 3A Avian Antibody (IgM)

Anti-Sema 3A avian antibody-producing clone No. 4-2 strain obtained in the step 4) was cultivated with IMDM medium in a $CO_2$ incubator in the presence of 5% $CO_2$ at 39.5° C. and the culture supernatant was harvested.

6) Preparation of Anti-Sema 3A Avian-Mouse Chimeric Antibody (IgG)

cDNA was synthesized from total RNA extracted from the anti-Sema 3A antibody producing clone No. 4-2 strain obtained in the step 4) by reverse transcription with a reverse transcriptase (SuperScript III, Life Technologies) and an oligo (dT) primer. The obtained cDNA was used as a template and light chain variable region genes were amplified by PCR using a sense primer containing the avian antibody λ light chain variable region sequence (primer 1: GAAGATCTAAGCTTGCCATGGCCTGGGCTCCTCTCCTCCT (SEQ ID NO: 27)) and an antisense primer containing the avian antibody λ light chain variable region sequence and the mouse antibody light chain constant region sequence (primer 2: TGGCGAAGACTTCGGCTGGCCTAGGAC (SEQ ID NO: 28)). At the same time, heavy chain variable region genes were amplified by PCR using a sense primer containing the avian antibody heavy chain variable region sequence (primer 3: GAAGATCTAAGCTTACCATGAGCCCACTCG (SEQ ID NO: 29)) and an antisense primer containing the avian antibody heavy chain variable region and mouse IgG2a antibody constant region (primer 4: CGATGGGGCTGTTGTTTTGGCGGAGGAGACGATGACTTC (SEQ ID NO: 30)). On the other hand, the DNA sequence of mouse antibody λ light chain constant region was used as a template and mouse light chain constant region genes were amplified by PCR using a sense primer containing a sense primer sequence of the avian antibody λ light chain variable region and the mouse antibody λ light chain constant region sequence (primer 5: AAGTCTTCGCCATCAGTCACCCTGTTTCCA (SEQ ID NO: 31)) and an antisense primer (primer 6: TATGCGGCCGCTTACTAGGAACAGTCA (SEQ ID NO: 32)). Additionally, the cDNA sequence of mouse IgG2a antibody heavy chain constant region was used as a template and mouse heavy chain constant region genes were amplified by PCR using a sense primer containing a sense primer sequence of the avian antibody heavy chain variable region and the mouse IgG2a antibody heavy chain constant region sequence (primer 7: GCCAAAACAACAGCCCCATCGGTCTATCCACTGGCCCCT (SEQ ID NO: 33)) and an antisense primer (primer 8: AGATAGCGGCCGCTTATCATTTACCCGG (SEQ ID NO: 34)).

The amplified light chain variable region fragment and light chain constant region fragment were used as a template and avian-mouse chimeric antibody light chain genes were amplified by PCR using primer 1 and primer 6. Furthermore, the amplified heavy chain variable region fragment and heavy chain constant region fragment were used as a template and avian-mouse chimeric antibody heavy chain genes were amplified by PCR using primer 3 and primer 8.

The avian-mouse chimeric antibody light chain genes and avian-mouse chimeric antibody heavy chain genes were digested with restriction enzymes Hind III and Not I, respectively, each of which then was cloned into Hind III-Not I site of a plasmid pCEP4 for expressing mammal cells (Life Technologies). The sequence of the cloned antibody gene was analyzed by sequencing using a DNA sequencer. Amino acid sequences of the avian-mouse chimeric antibody light chain and the avian-mouse chimeric antibody heavy chain were translated based on the analyzed nucleotide sequences. The final translated amino acid sequence of the avian-mouse chimeric antibody heavy chain is shown in SEQ ID NO: 35 and the final translated amino acid sequence of the avian-mouse chimeric antibody light chain is shown in SEQ ID NO: 36.

The constructed plasmid in the above step was transfected into FreeStyle 293 cell line (Life Technologies) using polyethyleneimine method and subjected to shaking culture at 37° C., 8% $CO_2$, and 135 rpm for 7 days to collect culture supernatant.

The concentration of anti-Sema 3A avian-mouse chimeric antibody (IgG) contained in the culture supernatant was quantified by ELISA. Anti-Sema 3A avian-mouse chimeric antibody was purified from the culture supernatant using a column prepared by loading Protein G Sepharose 4 Fast Flow (GE Healthcare) to Poly-Prep Chromatography Columns (Bio-Rad Laboratories, Inc.). A solvent of the eluted antibody was exchanged with PBS buffer using a PD-10 column (GE Healthcare).

Figure 2:
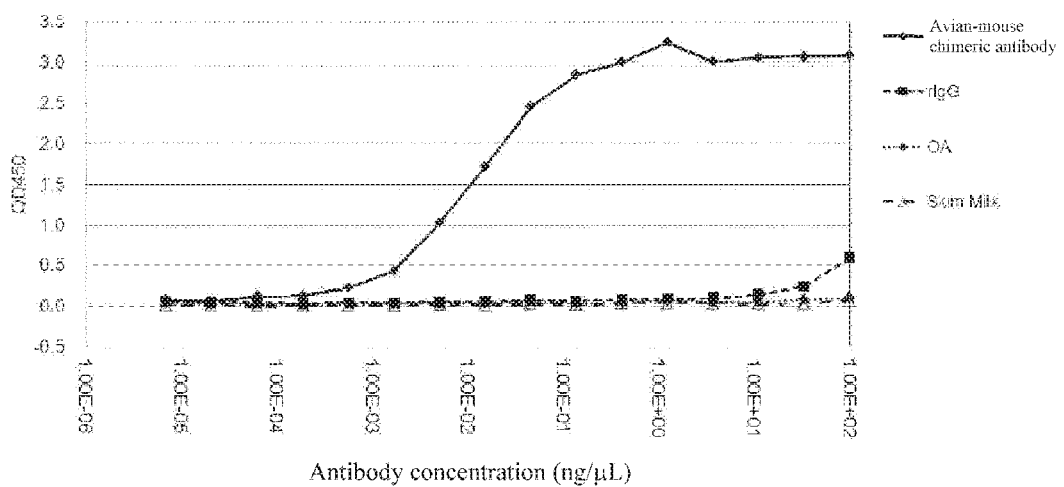
FIG. 2 shows a graph illustrating results of assessment of binding specificity of anti-Sema 3A avian-mouse chimeric antibody produced in Example 1 to Sema 3A protein.

The antigen specificity of the purified antibody was measured by ELISA with PBS buffer. 2.5 µg/mL of antigen was dispensed to a 96 well Maxi Sorp Plate (Nunc) and reacted overnight at 4° C. to coat the plate with an antigen (mouse Sema 3A protein). Ovalbumin, rabbit IgG and skim milk were immobilized in the plate as negative controls in similar manner in order to examine specificity of antibodies. The next day, the plate was washed three times with 200 µL/well of washing solution (PBS containing 0.05% Tween 20), to which was added 200 µL/well of blocking solution (PBS containing 0.5% skim milk) and the mixture was reacted for 30 minutes. The plate was washed three times with 200 µL/well of washing solution, to which was added 100 µL of culture supernatant containing antibody and the mixture was reacted for one hour. The plate was washed five times with 200 µL/well of washing solution, to which was added 100 µL/well of diluent in which anti-mouse $IgG_2A$ goat antibody labeled with horseradish peroxidase (HRP) (Bethyl Laboratories, Inc.) was diluted 2000 times with PBS buffer and the mixture was reacted for one hour. The plate was washed five times with 200 µL/well of washing solution, to which was added 100 µL/well of TMB+ (Dako) and the mixture was chromogenically reacted for five minutes. Subsequently, to the plate was added 100 µL of 1M sulfuric acid to quench the reaction. The absorbance was measured at 450 nm using μQuantBiomolecular Spectrometer (Bio Tek Instruments, Inc.) Results are shown in FIG. 2.

7) Determination of CDR Sequences in Variable Region of Anti-Sema 3A Avian-Mouse Chimeric Antibody CDR sequence of the anti-Sema 3A avian-mouse chimeric antibody obtained in the above step was determined. The CDR sequence was determined according to the method of Kabat et al. (Sequences of Proteins of Immunological Interest, NIH publication, 91-3242). Consequently, the following sequences were specified as the amino acid sequences of CDRs 1 to 3 of a heavy chain and a light chain.

TABLE 1

Anti-Sema 3A avian-mouse chimeric antibody (clone No. 4-2-derived)

| | |
|---|---|
| Heavy chain CDR 1 | SYPMG (SEQ ID NO: 1) (corresponding to positions 31 to 35 of SEQ ID NO: 35) |
| Heavy chain CDR 2 | GIDDDGDSDTRYAPAVKG (SEQ ID NO: 2) (corresponding to positions 50 to 67 of SEQ ID NO: 35) |
| Heavy chain CDR 3 | HTGIGANSAGSIDA (SEQ ID NO: 3) (corresponding to positions 100 to 113 of SEQ ID NO: 35) |
| Light chain CDR 1 | SGGGSYTGSYYYG (SEQ ID NO: 4) (corresponding to positions 21 to 33 of SEQ ID NO: 36) |
| Light chain CDR 2 | YNNKRPS (SEQ ID NO: 5) (corresponding to positions 50 to 56 of SEQ ID NO: 36) |
| Light chain CDR 3 | GSADNSGDA (SEQ ID NO: 6) (corresponding to positions 89 to 97 of SEQ ID NO: 36) |

Example 2: Preparation of Anti-Sema 3A Antibody (Humanized Antibody and Avian-Human Chimeric Antibody)

1) Construction of Humanized Antibody (Humanized-1 and Humanized-2) Genes

Two humanized antibodies (Humanized-1 and Humanized-2) were designed by altering to amino acids in the framework region of a human antibody from ones in the framework region of the variable region of anti-Sema 3A antibody produced by the clone No: 4-2 strain obtained in the step 4) of Example 1.

The designed heavy chain (the sequences of Humanized-1 and 2 are same) and Humanized-1 light chain amino acid sequence-encoding genes were separately synthesized with consideration of codon optimization to express in human cells. Alternatively, Humanized-1 light chain gene sequence was used as a template and the amplified product by PCR using a sense primer (primer Aγ: GAAGATCTAAGCTTCCACCATGGCAT (SEQ ID NO: 37)) and an antisense primer (primer Bγ: TTGTAATAGATCACTGTCACGGGA (SEQ ID NO: 38)) and the amplified product by PCR using a sense primer (primer Cγ: TCCCGTGACAGTGATCTATTACAA (SEQ ID NO: 39)) and an antisense primer (primer Dγ: AGATAGCGGCCGCTTAGGAACATTC (SEQ ID NO: 40)) were subjected to assembly PCR using a sense primer Aγ and an antisense primer Dγ in order to synthesize Humanized-2 light chain.

2) Construction of Avian-Human Chimeric Antibody Genes

Avian-human chimeric antibody genes were constructed as follows. cDNA of the obtained clone No. 4-2 strain in the step 4) of Example 1 was used as a template and light chain variable region genes were amplified by PCR using a sense primer containing the avian antibody λ light chain variable region sequence (primer Eγ: GAAGATCTAAGCTTCCACCATGGCCTGGGCTCCTCT (SEQ ID NO: 41)) and an antisense primer containing the avian antibody λ light chain variable region sequence and human antibody λ light chain constant region sequence (primer Fγ: CTTTGGGCTGGCCTAGGACGGTCAGGGTTGT (SEQ ID NO: 42)). Alternatively, heavy chain variable region genes were amplified by PCR using a sense primer containing the avian antibody heavy chain variable region sequence (primer Gγ: GAAGATCTAAGCTTCCACCATGAGCCCACTCG (SEQ ID NO: 43)) and an antisense primer containing the avian antibody heavy chain variable region and human antibody IgG 1 constant region (primer Hγ: GCCCCTTTGTACTAGCGGAGGAGACGATGACTTC (SEQ ID NO: 44)). On the other hand, the DNA sequence of synthesized Humanized-1 human antibody λ light chain constant region was used as a template and human λ light chain constant region genes were amplified by PCR using a sense primer containing the human antibody λ light chain constant region sequence (primer Iγ: GGCCAGCCCAAAGCCAACCCTACCGTG (SEQ ID NO: 45)) and an antisense primer (primer Jγ: AGATAGCGGCCGCTTATTAGGAACATTCGGTT (SEQ ID NO: 46)). Furthermore, the synthesized DNA sequence of Humanized-1 human IgG1 antibody heavy chain constant region was used as a template and human IgG1 heavy chain constant region genes were amplified by PCR using a sense primer containing the human IgG1 antibody heavy chain constant region sequence (primer Kγ: GCTAGTACAAAGGGGCCCTCAGTGTTCCCACTG (SEQ ID NO: 47)) and an antisense primer (primer Lγ: AGATAGCGGCCGCTTATTATTTTCCAGGTGACAG (SEQ ID NO: 48)).

The amplified light chain variable region fragment and light chain constant region fragment were used as a template and avian-human chimeric antibody light chain genes were amplified by PCR using the primer Eγ and primer Jγ. Furthermore, the amplified heavy chain variable region fragment and heavy chain constant region fragment were used as a template and avian-human chimeric antibody heavy chain genes were amplified by PCR using the primer Gγ and primer Lγ.

3) Construction of Expression Vector and Expression, Purification and Concentration Measurement of Protein The synthesized Humanized-1 light chain gene and heavy chain gene, Humanized-2 light chain gene and heavy chain gene, and avian-human chimeric antibody light chain gene and heavy chain gene were digested with restriction enzymes Hind III and Not I, each of which was cloned into Hind III-Not I site of a plasmid pCEP4 for expressing mammal cells (Life Technologies). The presence of the cloned antibody gene sequences was analyzed by sequencing using a DNA sequencer. Amino acid sequences of a humanized antibody (Humanized-1 and Humanized-2) and an avian-human chimeric antibody heavy chain and light chain were translated based on the sequenced nucleotide sequences.

The final determined amino acid sequence of humanized antibodies (Humanized-1 and Humanized-2) heavy chain is shown in SEQ ID NO: 49 and the amino acid sequence-encoding nucleotide sequence is shown in SEQ ID NO: 50. The amino acid sequence of the heavy chain (SEQ ID NO: 49) contains the amino acid sequence of the variable region shown in SEQ ID NO: 11. Furthermore, the final determined amino acid sequence of humanized antibody (Humanized-1) light chain is shown in SEQ ID NO: 51 and the amino acid sequence-encoding nucleotide sequence is shown in SEQ ID NO: 52. The amino acid sequence of the light chain (SEQ ID NO: 51) contains the amino acid sequence of the variable region shown in SEQ ID NO: 12. Additionally, the final determined amino acid sequence of humanized antibody (Humanized-2) light chain is shown in SEQ ID NO: 53 and the amino acid sequence-encoding nucleotide sequence is shown in SEQ ID NO: 54. The amino acid sequence of the light chain (SEQ ID NO: 53) contains the amino acid sequence of the variable region shown in SEQ ID NO: 13.

The final determined amino acid sequence of avian-human chimeric antibody (clone No. 4-2-derived) heavy chain is shown in SEQ ID NO: 55 and the amino acid sequence-encoding nucleotide sequence is shown in SEQ ID NO: 56. The amino acid sequence of the heavy chain (SEQ ID NO: 55) contains the amino acid sequence of the variable region shown in SEQ ID NO: 8. Furthermore, the final determined amino acid sequence of avian-human chimeric antibody (clone No. 4-2-derived) light chain is shown in SEQ ID NO: 57 and the amino acid sequence-encoding nucleotide sequence is shown in SEQ ID NO: 58. The amino acid sequence of the light chain (SEQ ID NO: 57) contains the amino acid sequence of the variable region shown in SEQ ID NO: 10.

The constructed expression plasmid in the above step was transfected into FreeStyle 293 cell line (Life Technologies) by polyethyleneimine and subjected to shaking culture at 37° C., 8% $CO_2$, and 135 rpm for 7 days to collect culture supernatant.

Anti-Sema 3A humanized antibodies (Humanized-1 and Humanized-2) and avian-human chimeric antibody were purified from the culture supernatant using a column prepared by loading Protein A Sepharose 4 Fast Flow (GE Healthcare) to Poly-Prep Chromatography Columns (Bio-Rad Laboratories, Inc). A solvent of the eluted antibody was exchanged with PBS buffer using a PD-10 column (GE Healthcare).

Figure 3:
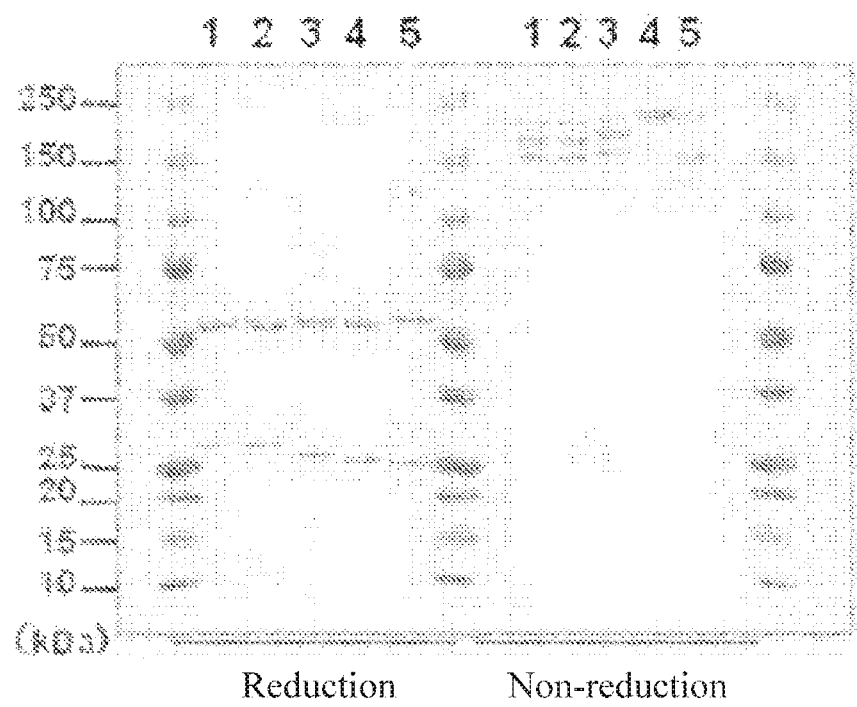
FIG. 3 shows the results that anti-Sema 3A avian-mouse chimeric antibody, anti-Sema 3A humanized antibody and anti-Sema 3A avian human chimeric antibody is applied to electrophoresis followed by CBB staining.
Figures 4C, 4D:
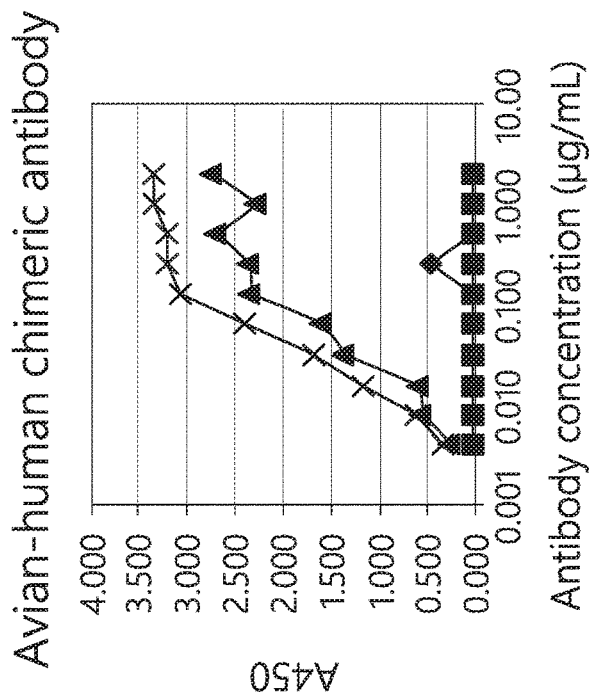
FIG. 4 shows test results of reactivity of anti-Sema 3A avian-mouse chimeric antibody, anti-Sema 3A humanized antibody and anti-Sema 3A avian-human chimeric antibody to human Sema 3A and mouse Sema 3A antigens.
Figures 4E, 4F:
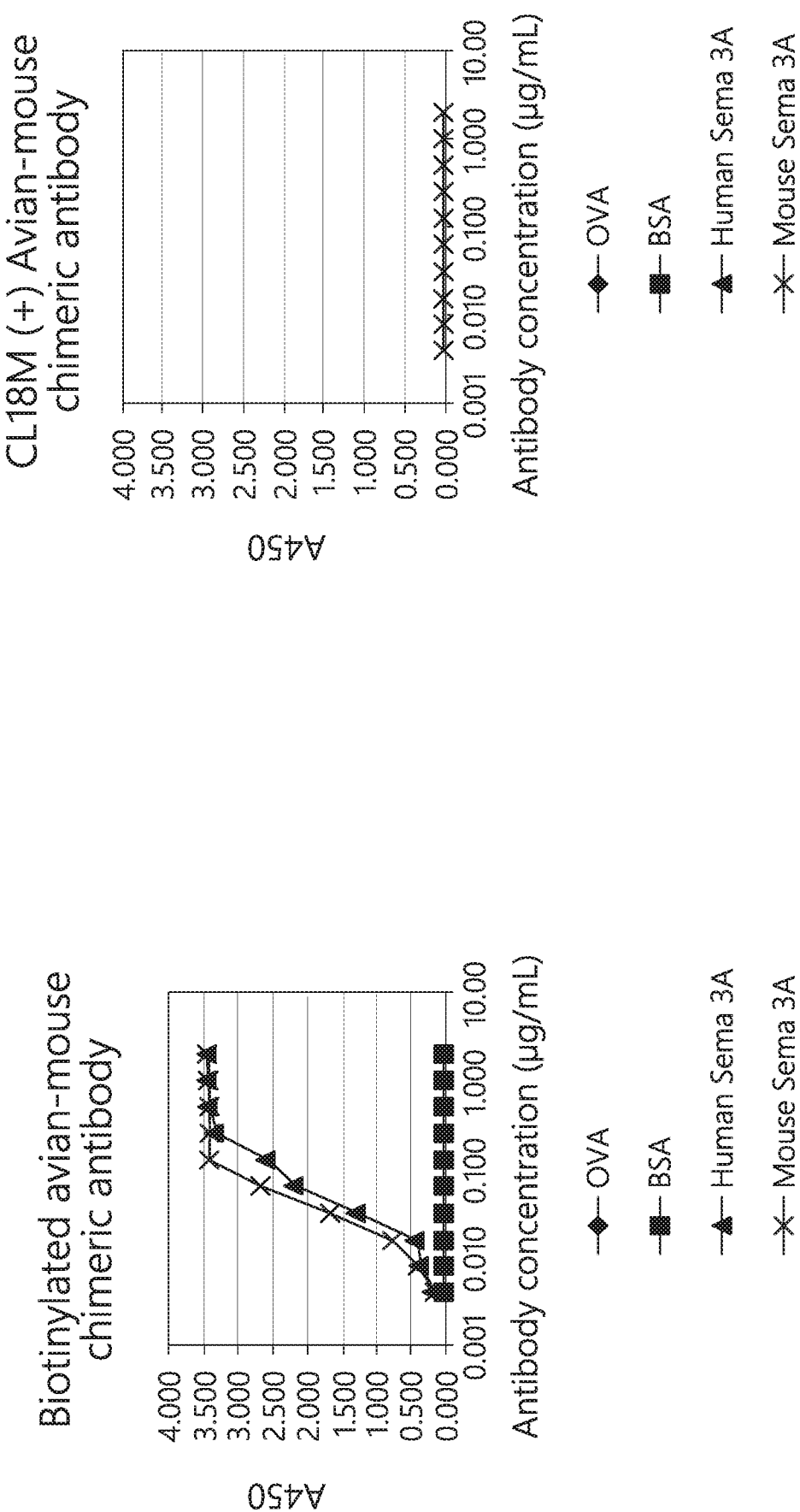

The molecular absorbance coefficient was calculated from amino acid composition of the purified antibody and the concentration was determined by ultraviolet absorbance method. 500 ng of the purified antibody in reduced or non-reduced state was subjected to electrophoresis and the gel was stained with Coomassie Brilliant Blue (CBB). Results are shown in FIG. 3. FIG. 3 also shows results of electrophoresis with CBB stain of the obtained avian-mouse antibody in Example 1 and CL18M (+) avian-mouse chimeric antibody (control).

Example 3: Preparation of Anti-Sema 3A Antibody (Avian-Mouse Chimeric Antibody)

Eight cell strains exhibiting positive for anti-Sema 3A antibody production were obtained in the same antibody screening process as the steps 1) and 2) of Example 1 except that human Sema 3A protein was used as an antigen and DT40 cells were used in which the constant region of chicken IgM was replaced with that of mouse IgG. Used were No. 165 and No. 582 strains among clones exhibiting positive for anti-Sema 3A antibody production for preparation and purification of anti-Sema 3A antibody to obtain anti-Sema 3A avian-mouse chimeric antibody (IgG) (clone No. 165 strain and clone No. 582 strain-derived). The variable regions of the heavy chain and light chain of anti-Sema 3A avian-mouse chimeric antibody and CDR sequencings were carried out, respectively. The CDR sequence was determined according to the method of Kabat et al. (Sequences of Proteins of Immunological Interest, NIH publication, 91-3242).

Results are shown in Tables 2 and 3.

TABLE 2

Anti-Sema 3A avian-mouse chimeric antibody (clone No. 165 strain-derived)

| | |
|---|---|
| Heavy chain variable region | AVTLDESGGGLQTPGGGLSLVCKASGFTFS SYEMQWVRQAPGKGLEWVAGIYTGSTWYGA AVKGRATISRDNGQSTVRLQLNNLRAEDTA IYYCAKSGIGVNSAAFIDAWGHGTEVIVSS (SEQ ID NO: 59) |
| Heavy chain CDR 1 | SYEMQ (SEQ ID NO: 60) (corresponding to positions 31 to 35 of SEQ ID NO: 59) |
| Heavy chain CDR 2 | GIYTGSTWYGAAVKG (SEQ ID NO: 61) (corresponding to positions 50 to 64 of SEQ ID NO: 59) |
| Heavy chain CDR 3 | SGIGVNSAAFIDA (SEQ ID NO: 62) (corresponding to positions 97 to 109 of SEQ ID NO: 59) |
| Light chain variable region | ALTQPASVSANPGETVKITCSGGGSYGGSY YYGWYQQKAPGSAPVTVIYNNNKRPSNIPS RFSGSLSGSTNTLTITGVRADDEAVYFCGS ADNSGTAFGAGTTLTVL (SEQ ID NO: 63) |
| Light chain CDR 1 | SGGGSYGGSYYYG (SEQ ID NO: 64) (corresponding to positions 21 to 33 of SEQ ID NO: 63) |
| Light chain CDR 2 | NNNKRPS (SEQ ID NO: 65) (corresponding to positions 50 to 56 of SEQ ID NO: 63) |
| Light chain CDR 3 | GSADNSGTA (SEQ ID NO: 66) (corresponding to positions 89 to 97 of SEQ ID NO: 63) |

TABLE 3

Anti-Sema 3A avian-mouse chimeric antibody (clone No. 582 strain-derived)

| | |
|---|---|
| Heavy chain variable region | AVTLDESGGGLQTPGGALSLVCKASGFTMS SYEMQWVRQAPGKGLEWVAAIYTRSTWYGA AVKGRATISRDNGQSTVRLQLNNLRAEDTG TYYCAKSGIGLNSAAFIDAWGHGTEVIVSS (SEQ ID NO: 67) |
| Heavy chain CDR 1 | SYEMQ (SEQ ID NO: 68) (corresponding to positions 31 to 35 of SEQ ID NO: 67) |
| Heavy chain CDR 2 | AIYTRSTWYGAAVKG (SEQ ID NO: 69) (corresponding to positions 50 to 64 of SEQ ID NO: 67) |
| Heavy chain CDR 3 | SGIGLNSAAFIDA (SEQ ID NO: 70) (corresponding to positions 97 to 109 of SEQ ID NO: 67) |
| Light chain variable region | ALTQPASVSANPGETVKITCSGGGSYGGSY YYGWYQQKAPGSAPVTVIYTNNKRPSNIPS RFSGSLSGSTNTLTITGVRADDEAVYFCGS ADNSGTAFGAGTTLTVL (SEQ ID NO: 71) |
| Light chain CDR 1 | SGGGSYGGSYYYG (SEQ ID NO: 72) (corresponding to positions 21 to 33 of SEQ ID NO: 71) |

TABLE 3-continued

Anti-Sema 3A avian-mouse chimeric
antibody (clone No. 582 strain-derived)

| | |
|---|---|
| Light chain CDR 2 | TNNKRPS (SEQ ID NO: 73)<br>(corresponding to positions<br>50 to 56 of SEQ ID NO: 71) |
| Light chain CDR 3 | GSADNSGTA (SEQ ID NO: 74)<br>(corresponding to positions<br>89 to 97 of SEQ ID NO: 71) |

Example 4: Preparation of Anti-Sema 3A Antibody (Avian Antibody and Avian-Human Chimeric Antibody)

1) Preparation of Avian Antibody (IgM)

Mouse Sema 3A protein was used as an antigen and antibody screening was carried out in the same process as the steps 1) and 2) in Example 1 to obtain clones exhibiting positive for anti-Sema 3A antibody production. Among the clones, 240-40 strain and 255-72 strain were used for preparation and purification of anti Sema 3A antibody to obtain anti-Sema 3A avian antibody (clone No. 240-40 strain and clone No. 255-72 strain-derived). The variable regions of the heavy chain and light chain of anti-Sema 3A avian antibody and CDR sequencings were carried out, respectively. The CDR sequence was determined according to the method of Kabat et al. (Sequences of Proteins of Immunological Interest, NIH publication, 91-3242). Results are shown in Tables 4 and 5.

TABLE 4

Anti-Sema 3A avian antibody
(clone No. 240-40 strain-derived)

| | |
|---|---|
| Heavy chain<br>variable region | AVTLDESGGGLQTPGGALSLVCKASGFTFSS<br>YDMNWVRQAPGKGLEWVAGIYSGSSTYYGAA<br>VKGRATISRDNGQSTLRLQLNNLRAEDTGIY<br>YCAKSAIPVNSAGSIDAWGHGTEVIVSS<br>(SEQ ID NO: 75) |
| Heavy chain CDR 1 | SYDMN (SEQ ID NO: 76)<br>(corresponding to positions<br>31 to 35 of SEQ ID NO: 75) |
| Heavy chain CDR 2 | GIYSGSSTYYGAAVKG (SEQ ID NO: 77)<br>(corresponding to positions<br>50 to 65 of SEQ ID NO: 75) |
| Heavy chain CDR 3 | SAIPVNSAGSIDA (SEQ ID NO: 78)<br>(corresponding to positions<br>98 to 110 of SEQ ID NO: 75) |
| Light chain<br>variable region | ALTQPASVSANPGETVKITCSGGGSYGGSYY<br>YSWHQQKSPGSALVTVIYYNNKRPSDIPSRF<br>SGSLSGSTNTLTITGVRADDEAVYFCGSADT<br>SGTAFGAGTTLTVL (SEQ ID NO: 79) |
| Light chain CDR 1 | SGGGSYGGSYYYS (SEQ ID NO: 80)<br>(corresponding to positions<br>21 to 33 of SEQ ID NO: 79) |
| Light chain CDR 2 | YNNKRPS (SEQ ID NO: 81)<br>(corresponding to positions<br>50 to 56 of SEQ ID NO: 79) |
| Light chain CDR 3 | GSADTSGTA (SEQ ID NO: 82)<br>(corresponding to positions<br>89 to 97 of SEQ ID NO: 79) |

TABLE 5

Anti-Sema 3A avian antibody
(clone No. 255-72 strain-derived)

| | |
|---|---|
| Heavy chain<br>variable region | AVTLDESGGGLQTPGGALSLVCKASGFTFSS<br>YEMQWVRQAPGKGLEWVAGIYSGSTWYGAAV<br>KGRATISRDNGQSTVRLQLNNLRAEDTGTYY<br>CAKSGIGFNSAGSIDAWGHGTEVIVSS<br>(SEQ ID NO: 83) |
| Heavy chain CDR 1 | SYEMQ (SEQ ID NO: 84)<br>(corresponding to positions<br>31 to 35 of SEQ ID NO: 83) |
| Heavy chain CDR 2 | GIYSGSTWYGAAVKG (SEQ ID NO: 85)<br>(corresponding to positions<br>50 to 64 of SEQ ID NO: 83) |
| Heavy chain CDR 3 | SGIGFNSAGSIDA (SEQ ID NO: 86)<br>(corresponding to positions<br>97 to 109 of SEQ ID NO: 83) |
| Light chain<br>variable region | ALTQPASVSANPGETVKITCSGGGSYGGSYY<br>YSWHQQKSPGSALVTVIYYNNKRPSDIPSRF<br>SGSLSGSTNTLTITGVRADDEAVYFCGSADN<br>SGSAFGAGTTLTVL (SEQ ID NO: 87) |
| Light chain CDR 1 | SGGGSYGGSYYYS (SEQ ID NO: 88)<br>(corresponding to positions<br>21 to 33 of SEQ ID NO: 87) |
| Light chain CDR 2 | YNNKRPS (SEQ ID NO: 89)<br>(corresponding to positions<br>50 to 56 of SEQ ID NO: 87) |
| Light chain CDR 3 | GSADNSGSA (SEQ ID NO: 90)<br>(corresponding to positions<br>89 to 97 of SEQ ID NO: 87) |

2) Preparation of Avian-Human Chimeric Antibody (IgG 1)

cDNA was synthesized from total RNA extracted from anti-Sema 3A antibody-producing clone No. 240-40 strain and 255-72 strain by reverse transcription with a reverse transcriptase (SuperScript III, Life Technologies). The obtained cDNA was used as a template and light chain variable region genes were amplified by PCR using a sense primer containing an avian antibody "A light chain variable region sequence (primer Mγ: AGCTTGCTAGCGGCCAC-CATGGCCTGGGCTCCTCTC (SEQ ID NO: 91)) and an antisense primer (primer Nγ: TCTGGCGGCCGCTAGACT-CACCTAGGACGGTCAGGGTTGTC (SEQ ID NO: 92)). Alternatively, heavy chain variable region genes were amplified by PCR using a sense primer containing an avian antibody heavy chain variable region sequence (primer Oγ: AGCTTGCTAGCGGCCACCATGAGC-CCACTCGTCTCC (SEQ ID NO: 93)) and an antisense primer (primer Pγ: TCTGGCGGCCGCTAGACTCACCG-GAGGAGACGATGACTTC (SEQ ID NO: 94)).

DNA sequences shown in SEQ ID NO: 95 in the heavy chain constant region and SEQ ID NO:96 in the light chain constant region were produced by total synthesis of their genes and both sequences were digested with Not I and Eag I, which then were linked to Not I site of a vector pCEP4 (Life Technologies).

The amplified variable region sequence was cloned to the vector containing the constant region constructed in the above manner. In particular, both of a heavy chain constant region vector and a light chain constant region vector were digested with Not I and heavy chain variable region cDNA and light chain variable region cDNA were linked with each vector using In-fusion HD Cloning Kit (TAKARA BIO INC.)

The constructed plasmid in the above step was transfected into FreeStyle 293 cell line (Life Technologies) by polyethyleneimine and subjected to shaking culture at 37° C., 8% $CO_2$, 135 rpm to recover culture supernatant, which was purified by Protein A to obtain anti-Sema 3A avian-human chimeric antibody (IgG1) (clone No. 240-40 strain and clone No. 255-72 strain-derived).

Example 5: Measurement of Antigenic Specificity

The obtained avian-mouse chimeric antibody in Example 1 and the obtained humanized antibodies (Humanized-1 and Humanized-2) and avian-human chimeric antibody in Example 2 were measured for antigenic specificity by antigen solid phase ELISA with PBS buffer. The obtained avian-mouse chimeric antibody in Example 1, which was labeled with biotin, was also measured for antigenic specificity. CL18M (+) avian-mouse chimeric antibody, which served as a negative control, was also measured for antigenic specificity. Particular measurement conditions were as follows.

Firstly, 2.5 µg/mL of antigen (mouse and human Sema 3A protein) was dispensed into a 384 Well MaxiSorp Plate (Nunc) and reacted overnight at 4° C. in order to coat the plate with the antigen. Otherwise, ovalbumin (OVA) and bovine serum albumin (BSA) were immobilized in the plate as negative controls in similar manner in order to examine specificity of antibodies. After reaction, the plate was washed three times with 50 µL/well of washing solution (PBS containing 0.05% Tween 20), to which was added 25 µL/well of blocking solution (PBS buffer containing 1% bovine serum albumin), and the mixture was reacted for 30 minutes. The resultant product was washed three times with 50 µL/well of washing solution, to which were added 20 µL/well of respective antibodies and the mixture was reacted for one hour. The resultant product was washed five times with 50 µL/well of washing solution, to which was added 20 µL of diluent in which anti-human λ light chain goat antibody labeled with horseradish peroxidase (HRP) (SouthernBiotech) was diluted 4000 times with PBS buffer, in which anti-mouse IgG2A goat antibody labeled with horseradish peroxidase (HRP) (Bethyl Laboratories, Inc.) was diluted 2000 times with PBS buffer or in which streptavidin labeled with horseradish peroxidase (HRP) (Thermo Fisher Scientific K.K.) was diluted 10000 times with PBS buffer and the mixture was reacted for one hour. The plate was washed five times with 50 µL/well of washing solution, to which was added 20 µL/well of TMB+ (Dako) and the mixture was chromogenically reacted for 20 minutes. Subsequently, to the each well was added 20 µL of 1 M sulfuric acid to quench the reaction. The absorbance was measured at 450 nm using Infinite M1000 (Tecan Trading AG).

Results are shown in FIGS. 4A to 4F. As apparently shown in FIGS. 4A to 4F, the antibodies obtained in Examples 1 and 2 are observed to exhibit reactivity with human Sema 3A and mouse Sema 3A antigen, but not to exhibit reactivity with ovalbumin and BSA used as negative antigens. Results show that antibodies obtained in Examples 1 and 2 exhibit cross reactivity specific to Sema 3A.

Example 6: Measurement of Affinity to Antigen-1

The obtained clone No. 4-2-derived avian-mouse chimeric antibody in Example 1, the obtained humanized antibodies in Example 2 (Humanized-1 and Humanized-2) and avian-human chimeric antibody were subjected to competitive ELISA to evaluate affinity to the antigen. CL18M (+) avian-mouse chimeric antibody, which served as a negative control, was also measured for affinity to the antigen. Particular measurement conditions were as follows.

Firstly, 2.5 µg/mL of antigen (mouse and human Sema 3A protein) was dispensed into a 384 Well MaxiSorp Plate (Nunc) and reacted overnight at 4° C. in order to coat the plate with the antigen. The next day, the plate was washed three times with 50 µL/well of washing solution (PBS containing 0.05% Tween 20), to which was added 25 µL/well of blocking solution (PBS containing 1% bovine serum albumin) and the mixture was reacted for 30 minutes. Each of humanized antibodies (Humanized-1 and Humanized-2), avian-human chimeric antibody and avian-mouse chimeric antibody was subjected to serial doubling dilution, to which was mixed anti-Sema 3A avian-mouse chimeric antibody labeled with biotin to the final concentration of 60 ng/mL, and the mixture was reacted with the antigen solid phase plate which was washed three times with 50 µL/well of washing solution for one hour. The plate was washed five times with 50 µL/well of washing solution, to which was added 20 µL/well of diluent in which streptavidin labeled with horseradish peroxidase (HRP) (Thermo Fisher Scientific K.K.) was diluted 10000 times with PBS buffer and the mixture was reacted for 30 minutes. The plate was washed five times with 50 µL/well of washing solution, to which was added 20 µL/well of TMB+ (Dako) and the mixture was chromogenically reacted for 20 minutes. Subsequently, to the each well was added 20 µL of 1M sulfuric acid to quench the reaction. The absorbance was measured at 450 nm using Infinite M1000 (Tecan Trading AG).

Figure 5:
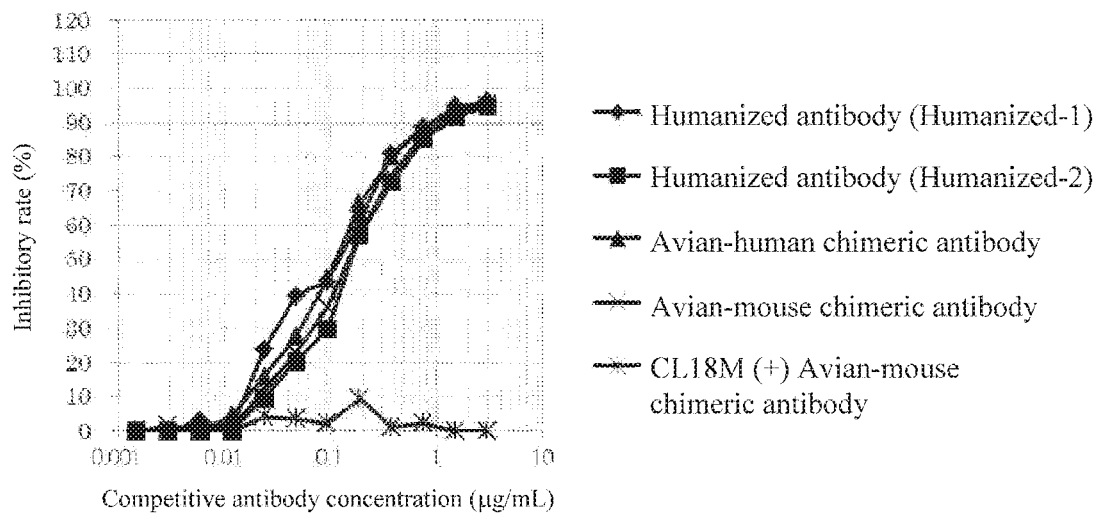
FIG. 5 shows measured results of affinity of anti-Sema 3A avian-mouse chimeric antibody, anti-Sema 3A humanized antibody and anti-Sema 3A avian-human chimeric antibody to Sema 3A protein by competitive ELISA.
Figure 5:
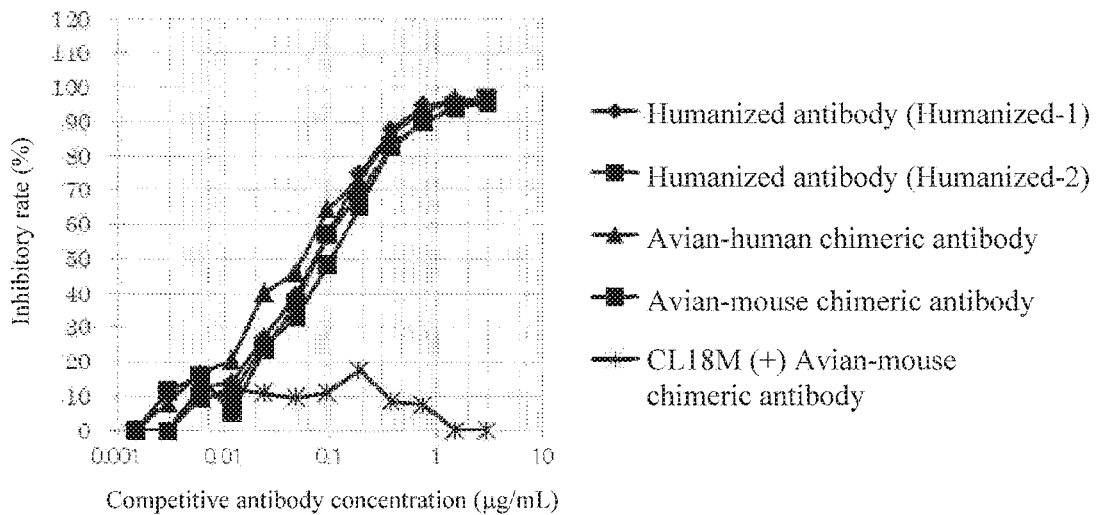
Figure 6B:
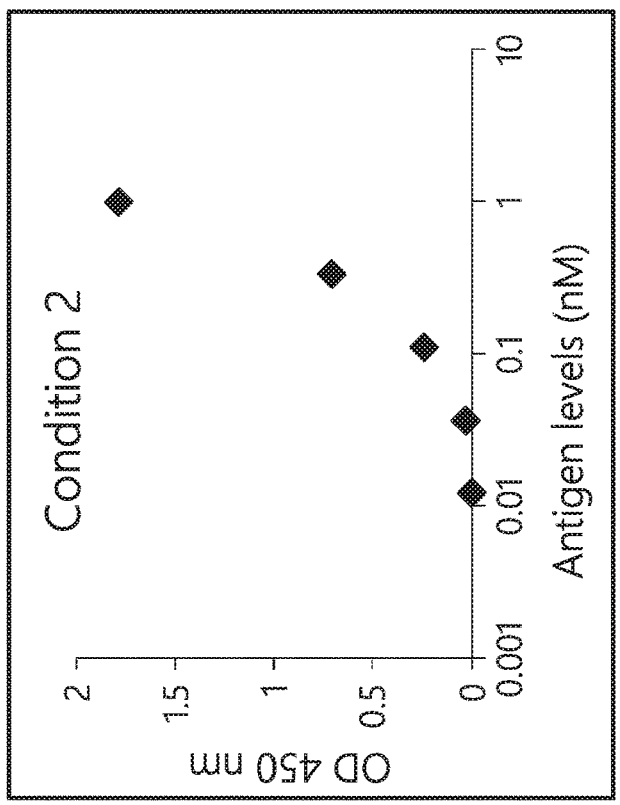
FIG. 6 shows measured results of Sema 3A in serum-free samples by sandwich ELISA with the anti-Sema 3A antibody produced in Examples 2 to 4.
Figure 6A:
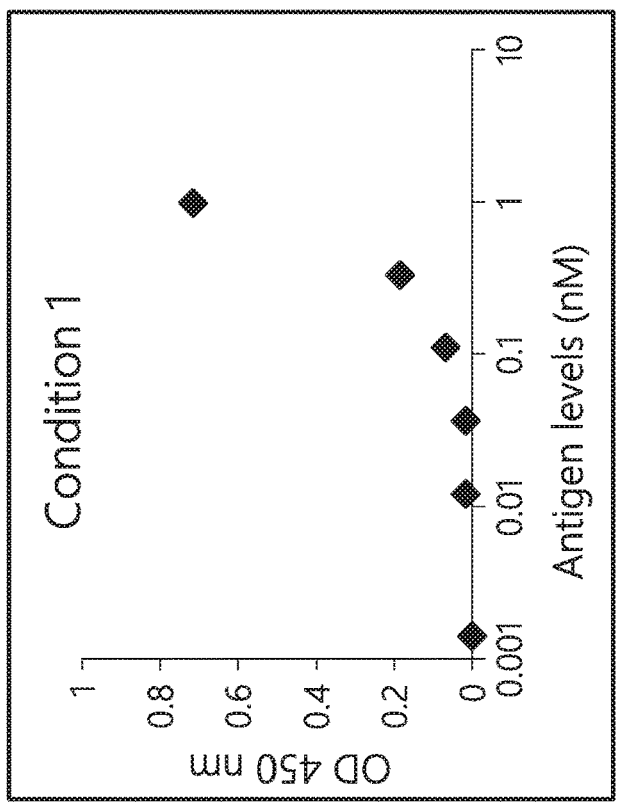
Figure 6D:
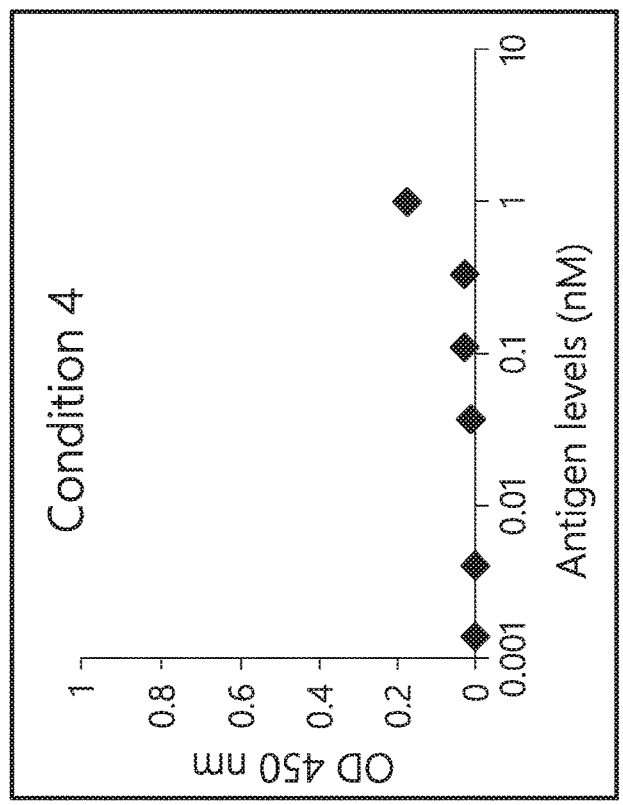
Figure 6C:
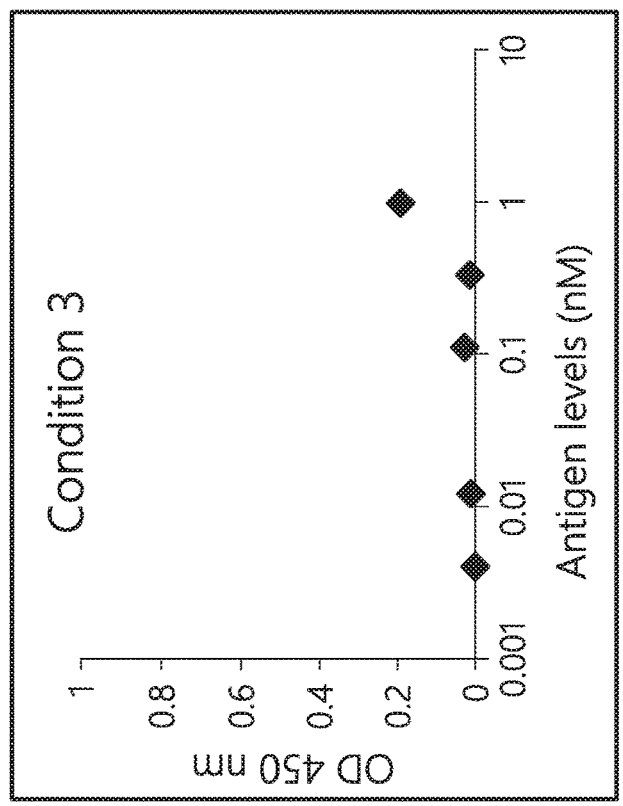
Figure 6E:
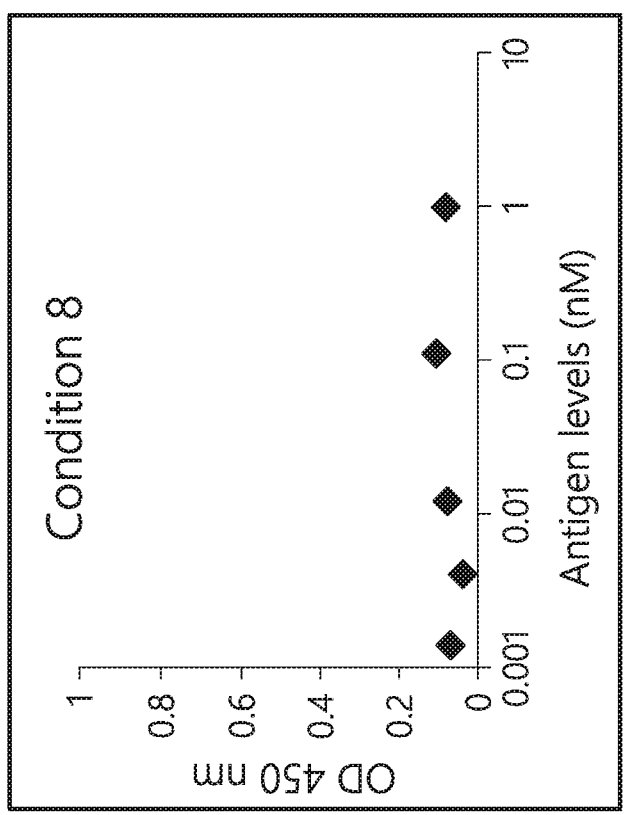

Results are shown in FIG. 5. Table 6 also shows results of calculated 50% inhibitory concentration $IC_{50}$ (µg/mL) of anti-Sema 3A avian-mouse chimeric antibody on antigen-antibody reaction for antibodies. Consequently, humanized antibodies (Humanized-1 and Humanized-2), avian-human chimeric antibody and avian-mouse chimeric antibody were almost comparable for affinity and therefore, humanized antibodies are not observed to have significant changes for affinity.

TABLE 6

| | $IC_{50}$ (µg/mL) | |
| --- | --- | --- |
| Clone No. 4-2-derived antibodies | Human Sema 3A antigen | Mouse Sema 3A antigen |
| Humanized antibody (Humanized-1) | 0.071 | 0.120 |
| Humanized antibody (Humanized-2) | 0.101 | 0.157 |
| Avian-human chimeric antibody | 0.54 | 0.112 |
| Avian-mouse chimeric antibody | 0.74 | 0.147 |
| CL18M (+) avian-mouse antibody (negative control) | N.D. | N.D. |

Example 7: Measurement of Affinity to Antigen-2

The obtained clone No. 4-2-derived avian-mouse chimeric antibody in Example 1, the obtained humanized antibodies (Humanized-1 and Humanized-2) in Example 2 and avian-human chimeric antibody were evaluated for affinity to the antigen using BIACORE (GE Healthcare). Particular conditions were as follows.

A sensor chip CM5 (GE Healthcare) was activated with 1-ethyl-3-(3-dimethylaminopropyl)carbodiimide (EDC) and N-hydroxysuccinimide (NHS) and then reacted with Protein A (NACALAI TESQUE, INC.) diluted to 50 µg/mL with Acetate 5.0 (GE Healthcare), that is, subjected to amine coupling reaction. Antibodies were reacted at concentrations of capture amount of about 200 RU, with which were reacted antigens (mouse and human Sema 3A protein) at a concentration of 100 nM, 50 nM, 25 nM, 12.5 nM, 6.25 nM or 3.125 nM. The association time was 3 minutes and the dissociation time was 4 minutes, from which reaction, the obtained sensorgram was analyzed by Langmuir binding model (BIAevaluation Version 4.1) (GE Healthcare) to calculate KD (dissociation constant).

Consequently, KD values for human Sema 3A were 3-4 nM for humanized antibodies (Humanized-1 and Humanized-2), I 4-I 5 nM for avian-human chimeric antibody and avian-mouse chimeric antibody. KD values for mouse Sema 3A were also 4-5 nM for humanized antibodies (Humanized-1 and Humanized-2), 17-18 nM for avian-human chimeric antibody and avian-mouse chimeric antibody. Both humanized antibodies of Humanized-1 and Humanized-2 had low KD values for Sema 3A compared to ones of the chimeric antibodies, suggesting affinity improvement by humanization.

Example 8: Measurement of Human Sema 3A by Sandwich ELISA

With use of the obtained anti-Sema 3A antibodies in Examples 2-4, human Sema 3A was measured by sandwich ELISA. Particular conditions were as follows.

Firstly, capture antibodies shown in Table 7 were diluted 1:2000, which was dispensed to a 384 Well Maxi Sorp Plate (Nunc) to react overnight at 4° C. in order to coat the plate with the capture antibodies. After reaction, each well was washed three times with a washing solution (PBS containing 0.05% Tween 20, pH 7.2), to which was added 45 µL of blocking solution (PBS containing 1% bovine serum albumin, pH 7.2) and the mixture was reacted for two hours at room temperature. Subsequently, the plate was washed three times with a washing solution (PBS containing 0.05% Tween 20, pH 7.2), to which was added 20 µL of antibodies and the mixture was reacted for one hour. Then, test samples were added in an amount of 25 µL to each well and the mixture was reacted at room temperature for one hour. Note that for the test sample, used was a diluent in which recombinant human Sema 3A-Fc chimeric protein (R&D systems, #1250-53-02J) was serially diluted with PBS or a diluent in which recombinant human Sema 3A-Fc chimeric protein (R&D systems, #1250-53-02J) was serially diluted with human serum type AB (Sigma-Aldrich Japan, # H4522) diluted five times with PBS. Subsequently, the wells were washed three times with a washing solution (PBS containing 0.05% Tween 20, pH 7.2), to each of which was added 25 µL of a primary antibody shown in Table 7 (diluted with PBS containing 1% bovine serum albumin (pH 7.2), at a concentration of 0.1 µg/mL) and the mixture was reacted at room temperature for one hour. The resultant product was washed five times with a washing solution (PBS containing 0.05% Tween 20, pH 7.2) and then reaction and detection of a secondary antibody were carried out by the following methods.

(Cases of Conditions 1, 2 and 5-8)

Anti-mouse IgG antibody labeled with horseradish peroxidase (HRP) (GE # NA931; diluted 1:1000 with PBS containing 1% bovine serum albumin (pH 7.2)) was added in an amount of 25 µL to each well and the mixture was reacted at room temperature for one hour, followed by washing five times with a washing solution (PBS containing 0.05% Tween 20, pH 7.2). Subsequently, to the each well was added 20 µL of TMB (Dako, # S1599) and the mixture was chromogenically reacted for 20 minutes, to which was added 20 µL of 1N sulfuric acid to quench the reaction. The absorbance was measured at 450 nm using Infinite M1000 (Tecan Trading AG).

(Cases of Conditions 3 and 4)

Mouse anti-avian IgM antibody labeled with biotin (BeckmanCoulter Inc. #733087; diluted 1:20000 with PBS containing 1% bovine serum albumin (pH 7.2)) was added in an amount of 25 µL to each well and the mixture was reacted at room temperature for one hour, followed by washing five times with a washing solution (PBS containing 0.05% Tween 20, pH 7.2). Subsequently, streptavidin labeled with horseradish peroxidase (HRP) (Thermo Fisher Scientific K.K. 21130; diluted 10000 times with PBS containing 1% bovine serum albumin (pH 7.2)) was added in an amount of 25 µL to each well and the mixture was reacted at room temperature for one hour, followed by washing five times with a washing solution (PBS containing 0.05% Tween 20, pH 7.2). Subsequently, 20 µL of TMB (Dako, # S1599) was added to the each well and the mixture was chromogenically reacted for 20 minutes, to which 20 µL of 1N sulfuric acid was added to quench the reaction. The absorbance was measured at 450 nm using Infinite M1000 (Tecan Trading AG).

(Case of Condition 9)

Anti-goat IgG antibody labeled with horseradish peroxidase (HRP) (Bethyl Laboratories, Inc. # A50; diluted 1:10000 with PBS containing 1% bovine serum albumin (pH 7.2)) was added in an amount of 25 µL to each well and the mixture was reacted at room temperature for one hour, followed by washing five times with a washing solution (PBS containing 0.05% Tween 20, pH 7.2). Subsequently, to the 20 µL of TMB (Dako, # S1599) was added to the each well and the mixture was chromogenically reacted for 20 minutes, to which 20 µL of 1N sulfuric acid was added to quench the reaction. The absorbance was measured at 450 nm using Infinite M1000 (Tecan Trading AG).

Figure 7B:
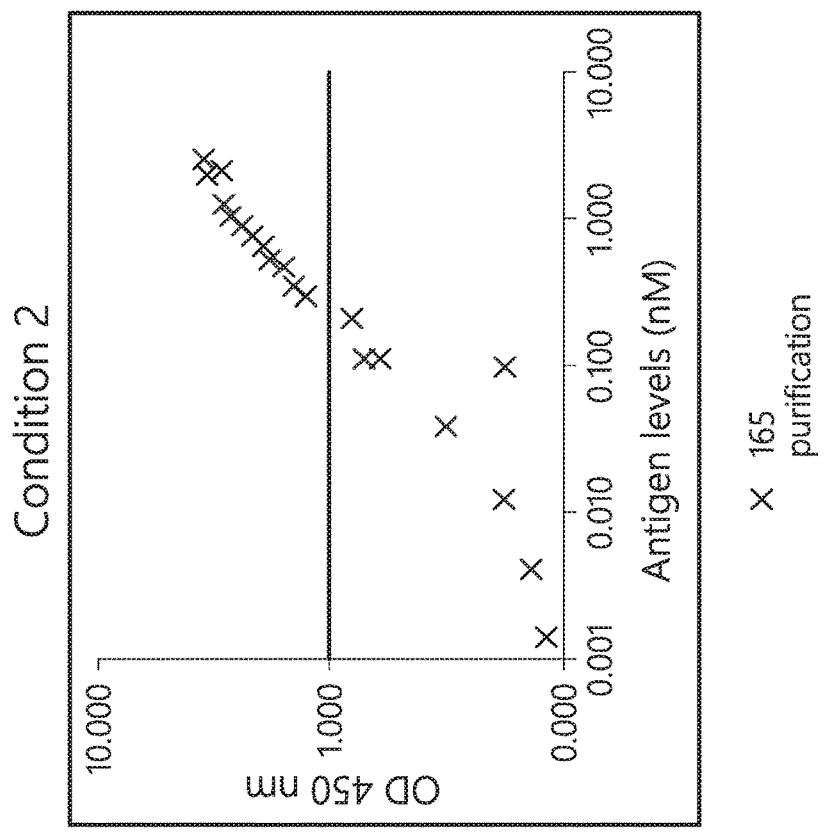
FIG. 7 shows measured results of Sema 3A in serum-containing samples by sandwich ELISA with the anti-Sema 3A antibody produced in Examples 2.
Figure 7A:
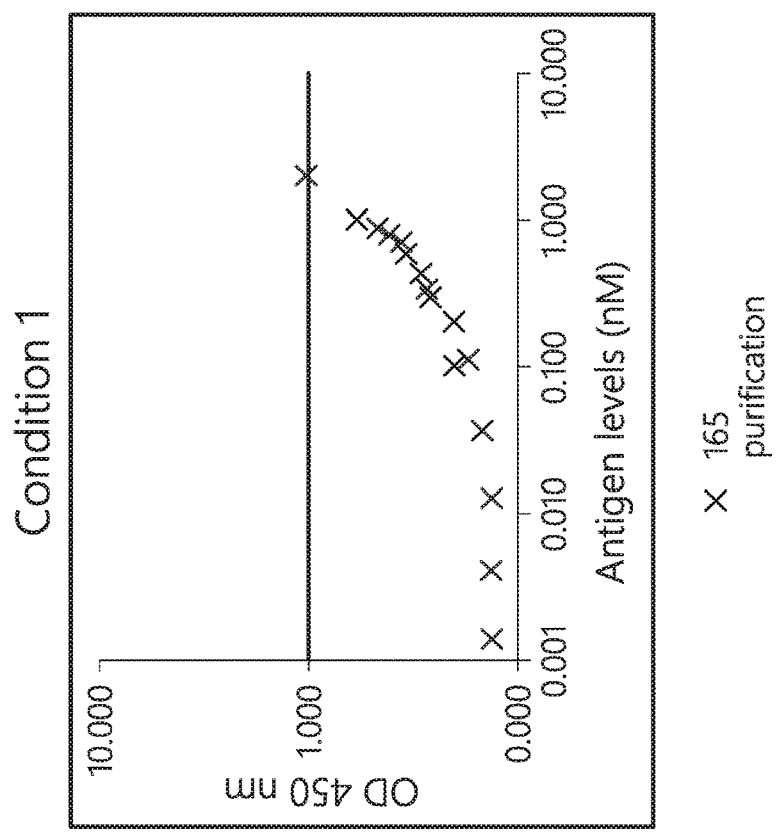

The obtained results are shown in Table 7, and FIGS. 6 and 7. Note that FIGS. 6A to 6E shows a relationship of antigen (Sema 3A) and OD 450 (absorbance at 450 nm) obtained by measuring test samples not containing serum in Conditions 1 to 4 and 8. FIGS. 7A to 7B also shows a relationship of antigen (Sema 3A) and OD 450 (absorbance at 450 nm) obtained by measuring test samples containing serum in Conditions 1 and 2. These results apparently shows that use of anti-Sema 3A antibodies obtained in Examples 1 to 4 allows to measure Sema 3A by ELISA. In the case where the obtained humanized antibody (Humanized-2) in Example 2 was used as a capture antibody and the obtained avian-mouse chimeric antibodies (clone No. 165 strain and clone No. 582 strain-derived) in Example 3 were used as the primary antibodies (Conditions 1 and 2), Sema 3A in serum also can be measured in a high accurate manner, which was found that Sema 3A in an analyte derived from biological entity can be measured. On the other hand, in the case where anti-Sema 3A antibody available commercially was used (Condition 9), Sema 3A could not be detected.

TABLE 7

| | Test conditions | | Test results | | | |
|---|---|---|---|---|---|---|
| | | | Test Samples (cases of serum-free) | | Test samples (cases of serum-containing) | |
| | Capture antibodies | Primary antibodies | Results | Absorbance at 450 nm of Sema 3A of 1 μm | Results | Absorbance at 450 nm of Sema 3A of 1 μm |
| Condition 1 | Humanized antibody obtained in Example 2 (Humanized-2) | Avian-mouse chimeric antibody obtained in Example 3 (clone No. 166 strain-derived) | Detectable | 0.706 | Detectable | 0.807 |
| Condition 2 | Humanized antibody obtained in Example 2 (Humanized-2) | Avian-mouse chimeric antibody obtained in Example 3 (clone No. 582 strain-derived) | Detectable | 1.799 | Detectable | 0.811 |
| Condition 3 | Humanized antibody obtained in Example 2 (Humanized-2) | Avian antibody obtained in Example 4 (clone No. 240-40 strain-derived) | Detectable | 0.191 | Not performed | |
| Condition 4 | Humanized antibody obtained in Example 2 (Humanized-2) | Avian antibody obtained in Example 4 (clone No. 255-72 strain-derived) | Detectable | 0.174 | Not performed | |
| Condition 5 | Avian antibody obtained in Example 4 (clone No. 240-40 strain-derived) | Avian-mouse chimeric antibody obtained in Example 1 (clone No. 4-2 strain-derived) | Detectable | 3.403 | Not performed | |
| Condition 6 | Avian antibody obtained in Example 4 (clone No. 255-72 strain-derived) | Avian-mouse chimeric antibody obtained in Example 1 (clone No. 4-2 strain-derived) | Detectable | 2.916 | Not performed | |
| Condition 7 | Avian-human chimeric antibody obtained in Example 4 (clone No. 240-40 strain-derived) | Avian-mouse chimeric antibody obtained in Example 1 (clone No. 4-2 strain-derived) | Detectable | 3.288 | Not performed | |
| Condition 8 | Avian-human chimeric antibody obtained in Example 4 (clone No. 255-72 strain-derived) | Avian-mouse chimeric antibody obtained in Example 1 (clone No. 4-2 strain-derived) | Detectable | 1.889 | Not performed | |
| Condition 9 | Humanized antibody obtained in Example 2 (Humanized-2) | Goat anti-Sema 3A polyclonal IgG (marketed product) | Undetectable | — | Not performed | |

Example 9: Collapse Assay-1

1) Test Method

Dorsal root ganglion (DRG) of Day 7 chicken embryo was isolated from a chicken. The isolated DRG was subjected to stationary culture in a 24 well dish coated with PLL and laminin containing 250 μL of NGF-containing medium at 37° C. for 16 to 20 hours, from which was observed elongation of NGF-sensitive DRG neurons. Aside from this, a mixed solution of chicken-derived Sema 3A protein (3 nM) and the obtained anti-Sema 3A avian antibody in Example 1 (culture supernatant) (at an antibody concentration of 10 μg/mL) or anti-Sema 3A avian-mouse chimeric antibody (10 μg/mL) was pre-incubated on ice for 30 minutes. The mixed solution was added to the 24 well dish so as to provide 0, 0.1 or 0.3 nM of the final concentration of the chicken-derived Sema 3A protein and the mixed solution was subjected to stationary culture at 37° C. for 30 minutes. Subsequently, the neurons were immobilized with a 3.7% formalin solution, and the growth cone, which was formed at the end of axons of the culture neurons, was visualized with Alexa488-conjugated Phalloidin. The rate (%) of neurons with collapsed growth cones to total NGF-sensitive DRG neurons was fluorescence-microscopically determined. Anti-rabbit IgG antibody or mouse IgG was also used as a control instead of anti-Sema 3A avian antibody or anti-Sema 3A avian-mouse chimeric antibody and collapse assay was carried out in the same manner as described above.

2) Results

Figure 8:
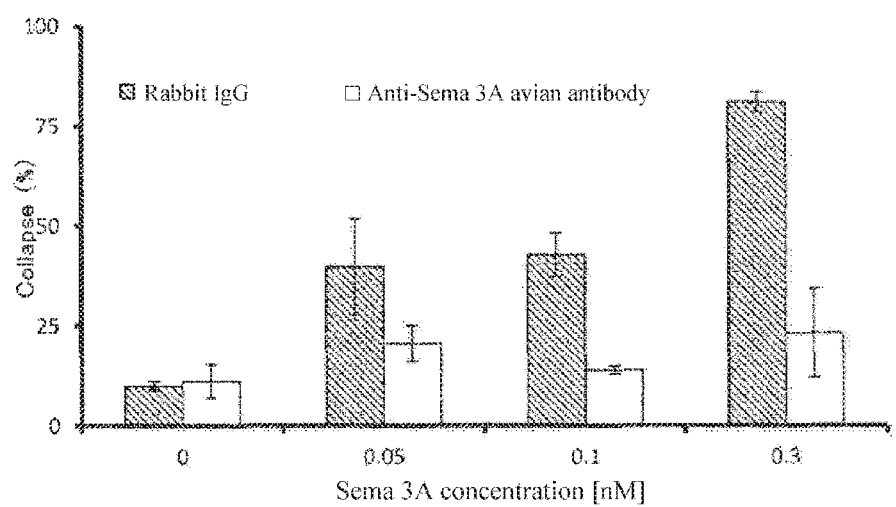
FIG. 8 shows results of collapse assay with chicken-derived Sema 3A protein and anti-Sema 3A avian antibody.
Figures 9, 10, 11:
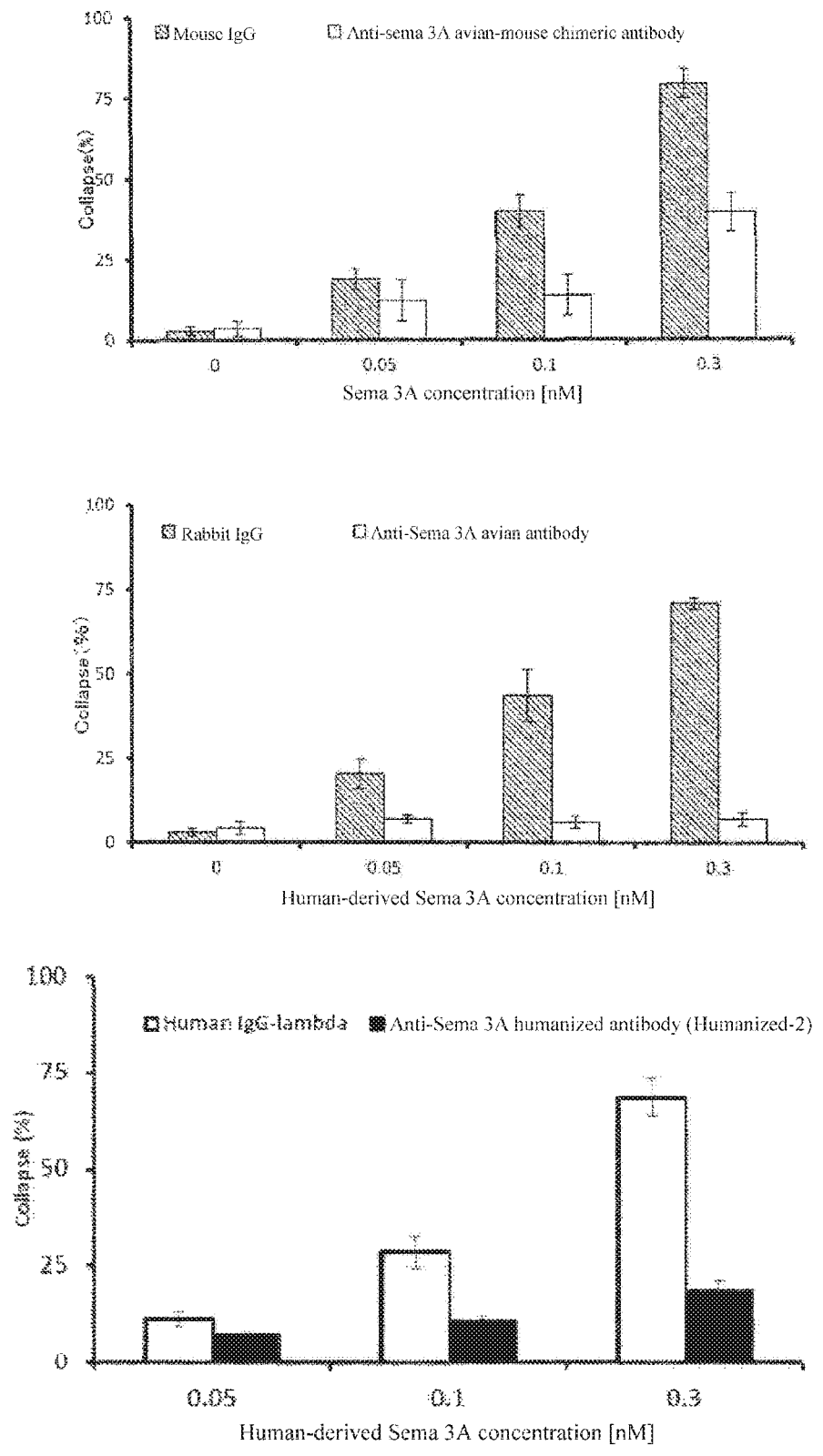

FIG. 8 shows results of collapse assay with anti-Sema 3A avian antibody and FIG. 9 shows results of collapse assay with anti-Sema 3A avian-mouse chimeric antibody. As apparently shown in FIGS. 8 and 9, anti-Sema 3A avian antibody and anti-Sema 3A avian-mouse chimeric antibody are observed to have the action of suppressing growth cone collapse by Sema 3A protein. That is, there is revealed that anti-Sema 3A antibody containing CDRs 1 to 3 having specific amino acid sequences can effectively suppress the ability of collapse induction of growth cone by Sema 3A protein.

Example 10: Collapse Assay-2

1) Test Method

Collapse assay was carried out in the same process as Example 9 except that human-derived Sema 3A protein was used instead of chicken-derived Sema 3A protein.

2) Results

FIG. 10 shows results of collapse assay with anti-Sema 3A avian antibody. As shown in FIG. 10, anti-Sema 3A avian antibody could effectively suppress a function of human-derived Sema 3A protein thereby to suppress growth cone collapse. That is, there is revealed that anti-Sema 3A antibody containing CDRs 1 to 3 having specific amino acid sequences can also effectively suppress the ability of collapse induction of growth cone by Sema 3A protein in human.

Example 11: Collapse Assay-3

1) Test Method

Dorsal root ganglion (DRG) of Day 7 chicken embryo was isolated from a chicken. The isolated DRG was subjected to stationary culture in a 24 well dish coated with PLL and laminin containing 250 μL of NGF-containing medium at 37° C. for 16 to 20 hours, from which was observed elongation of NGF-sensitive DRG neurons. Aside from this, a mixed solution of human-derived Sema 3A protein (3 nM) and the obtained anti-Sema 3A humanized antibody in Example 2 (Humanized-2) (culture supernatant) (at an antibody concentration of 100 µg/mL) was pre-incubated on ice for 30 minutes. The mixed solution was added to the 24 well dish so as to provide 0, 0.05, 0.1 or 0.3 nM of the final concentration of the human-derived Sema 3A protein and the mixed solution was subjected to stationary culture at 37° C. for 30 minutes. Subsequently, the neurons were immobilized with a 3.7% formalin solution, and the growth cone, which was formed at the end of axons of the culture neurons, was visualized with Alexa488-conjugated Phalloidin. The rate (%) of neurons with collapsed growth cones to total NGF-sensitive DRG neurons was fluorescence-microscopically determined. Human IgG-lambda was used as a control instead of anti-Sema 3A humanized antibody and collapse assay was carried out in the same manner as described above.

2) Results

FIG. 11 shows results of collapse assay with anti-Sema 3A humanized antibody. As apparently shown in FIG. 11, anti-Sema 3A humanized antibody is observed to have the action of suppressing growth cone collapse by Sema 3A protein. That is, there is revealed that anti-Sema 3A antibody containing CDRs 1 to 3 having specific amino acid sequences can effectively suppress the ability of collapse induction of growth cone by Sema 3A protein also in the case of being humanized.

Example 12: Binding Assay to Human Sema 3A

1) Test Method

Prepared was wild type COS-7 cells or COS-7 cells transformed so as to express EGFP (Enhanced Green Fluorescent Protein)-fused NRP1 (Neuropilin-1). Aside from this, DMEM medium containing alkaline phosphatase-conjugated human-derived Sema 3A protein (0.1 nM) and the obtained avian anti-Sema 3A antibody in Example 1 (culture supernatant) (at an antibody concentration of 10 µg/mL) or anti-Sema 3A avian-mouse chimeric antibody (10 µg/mL) was pre-incubated on ice for 30 minutes, 500 µL of which was added to wild-type COS-7 cells or NRP1-expressing COS-7 cells which was previously blocked with HBH buffer (Hanks' balanced salt solution containing 20 mM sodium HEPES, pH 7.00, 0.05 vol % BSA and 10 vol % FBS) and the mixture was left to stand on ice for one hour. Subsequently, the cells were washed four times with HBH buffer and then immobilized with a 4% formaldehyde. The immobilized cells was washed once with HH buffer (Hanks' balanced salt solution containing 20 mM sodium HEPES, pH 7.00), to which then was added 500 µL of alkaline phosphatase substrate (NBT/BLIP: nitro-blue tetrazolium chloride/5-bromo-4-chloro-3'-indolyphosphate p-toluidine salt) and the mixture was left to stand at room temperature overnight. Subsequently, cells were observed for a degree of chromogenic reaction using microscopy. Control assay was carried out in the same process as described above except that alkaline phosphatase binding human-derived Sema 3A protein was not added, or rabbit IgG was used instead of anti-Sema 3A avian antibody or anti-Sema 3A avian-mouse chimeric antibody. Note that NRP 1-expressing COS-7 cells used in the test is confirmed to have no variation of NRP1 expression level based on the fluorescence intensity of EGFP from the cells.

2) Results

Figure 12:
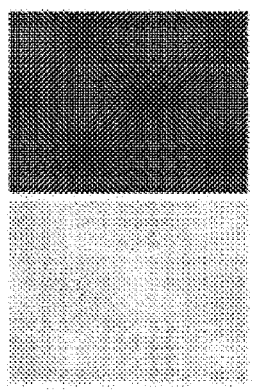
FIG. 12 shows results of binding assay of anti-Sema 3A avian antibody to human-derived Sema 3A protein.
Figure 12:
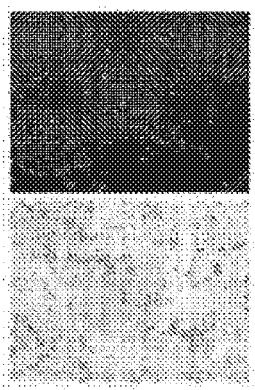
Figure 12:
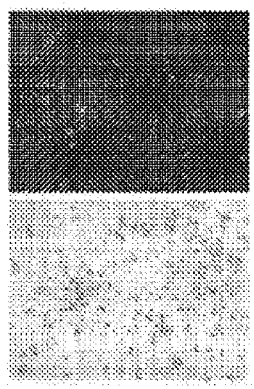
Figure 12:
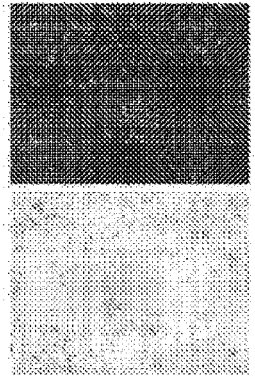
Figure 13:
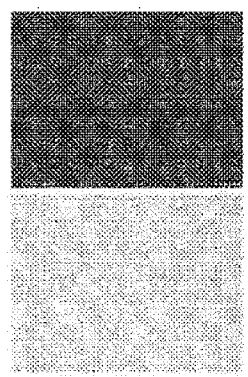
FIG. 13 shows results of binding assay of anti-Sema 3A avian-mouse chimeric antibody to human-derived Sema 3A protein.
Figure 13:
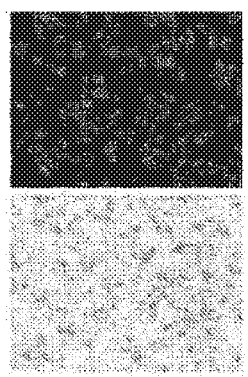
Figure 13:
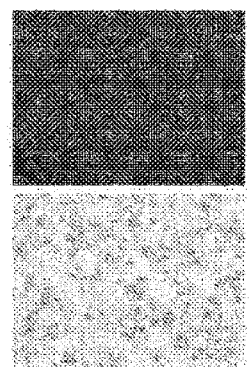
Figure 13:
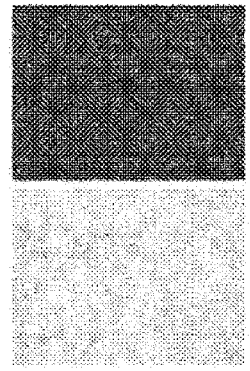

FIG. 12 shows results of binding assay with anti-Sema 3A avian antibody and FIG. 13 shows results of binding assay with anti-Sema 3A avian-mouse chimeric antibody. As apparently shown in FIGS. 12 and 13, in the case of addition of the mixture of avian anti-Sema 3A antibody or anti-Sema 3A avian-mouse chimeric antibody and human Sema 3A protein, binding of human-derived Sema 3A protein to NRP 1-expressing COS-7 cells was inhibited. That is, results reveal that anti-Sema 3A antibody containing CDRs 1 to 3 having specific amino acid sequences binds to human-derived Sema 3A protein and can inhibit binding of human-derived Sema 3A protein and NRP 1.

Example 13: Binding Assay to Human Sema 3F

1) Test Method

Binding assay was carried out in the same process as Example 12 except for use of COS-7 cells transformed so as to express EGFP-fused NRP 2 (Neuropilin-2) (NRP 2-expressing COS-7 cells) instead of NRP 1-expressing COS-7 cells and of alkaline phosphatase-conjugated human-derived Sema 3F protein instead of alkaline phosphatase-conjugated human-derived Sema 3A protein.

2) Results

Figure 14:
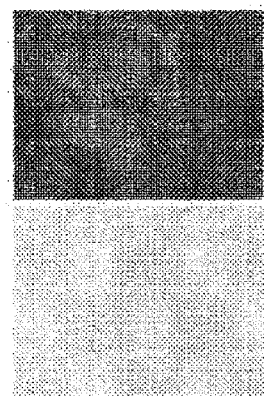
FIG. 14 shows results of binding assay of anti-Sema 3A avian antibody to human-derived Sema 3F protein.
Figure 14:
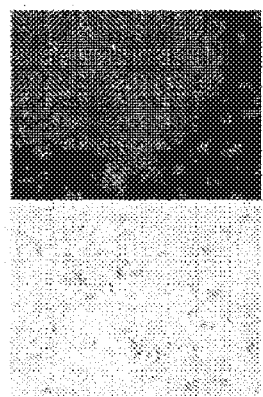
Figure 14:
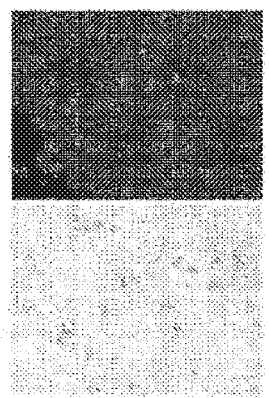
Figure 14:
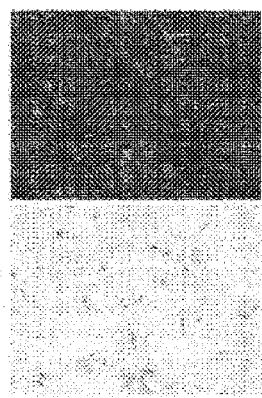

FIG. 14 shows results of binding assay with anti-Sema 3A avian antibody. As apparently shown in FIG. 14, even in the case of addition of a mixture of anti-Sema 3A avian antibody and human-derived Sema 3F protein, binding of human-derived Sema 3F protein to NRP 2-expressing COS-7 cells was not inhibited. That is, results reveal that anti-Sema 3A antibody containing CDRs 1 to 3 having specific amino acid sequences dose not bind to Sema 3F protein which is a subfamily molecule having high homology with Sema 3A protein, suggesting possibility to specifically bind to Sema 3A protein.

Example 14: Analysis of Influence of Anti-Sema 3A Antibody on Cognitive Function 1) Test Materials 1-1) Aβ (25-35) and Aβ (35-25)

Aβ (25-35) (Amyloid β-protein (25-35)) (Bachem, # H-1192) and Aβ (35-25) (Amyloid β-protein (35-25)) (Bachem, # H-2964) were prepared with distilled water to 1 mg/mL and then incubated at 37° C. for 4 days to prepare an Aβ (25-35) solution and an Aβ (35-25) solution. Through this process, Aβ (25-35) aggregates and achieves cell cytotoxicity. On the other hand, Aβ (35-25) is an inactivated Aβ which has the reversed amino acid sequence of activated Aβ 25-35 and does not exhibit cell cytotoxicity even after the process. Aβ (35-25) was used as a negative control.

1-2) Anti-Sema 3A Antibody

The produced anti-Sema 3A avian-mouse chimeric antibody in Example 1 was prepared with physiological saline to 1 mg/mL to prepare an anti-Sema 3A antibody solution.

1-4) Normal IgG

For a normal IgG solution, 1 mg/mL of normal mouse IgG (obtained from Calbiochem) was used.

1-5) Mouse

Mice (C57BL/6J) aged 3 weeks old purchased from CHARLES RIVER LABORATORIES JAPAN, INC. were used.

2) Test Method

Novel Object Recognition Task (NORT) was carried out according to the following method.

Firstly, mice aged 3 weeks old were prepared and acclimated to an experimenter by handling such that mice were put on experimenter's hand for 10 minutes a day for 2 weeks. Secondly, mice were divided into 5 groups shown in Table 8 and intracerebroventricularly administered with Aβ and an antibody under conditions shown in Table 8. These solutions were administered at 1 mm right inferior of bregma. Administration was carried out using a microsyringe equipped with a teflon tube (Eicom Corporation) connected at the needle tip of the syringe and a 27G injection needle (TERUMO CORPORATION) bent into L shape at 3.3 mm from the tip of the needle and inserted into the tip of the tube.

TABLE 8

| Group | Administration conditions |
| --- | --- |
| Intact group (N = 24) | Non-treated (no Aβ and antibody-treated) |
| Aβ (35-25)-treated group (N = 34) | ICV administration of Aβ (35-25) solution of 3 μL |
| Aβ (25-35)-treated group (N = 43) | ICV administration of Aβ (25-35) solution of 3 μL |
| Aβ (25-35) + normal IgG-treated group (N = 22) | ICV administration of Aβ (25-35) solution of 3 μL and normal IgG solution of 3 μL at the same time |
| Aβ (25-35) + anti-Sema 3A antibody-treated group (N = 22) | ICV administration of Aβ (25-35) solution of 3 μL and anti-Sema 3A antibody solution of 3 μL at the same time |

3 days after intracerebroventricular administration, mice were transferred into a test cage with 35 cm×35 cm×35 cm and acclimated in the test cage for 10 minutes. The next day (Day 4 after administration), Objects A and B were placed on given positions in the test cage and an amount of time to access to each of the Objects for 10 minutes was measured (acquisition trial). At this time, an amount of time to access within 1 cm or less of distance between the Object and nose of the mouse was measured as an access time. In the next day (Day 5 after administration), an amount of access time to each of the Object A and a new Object C instead of the Object B for 10 minutes was measured (test trial).

Note that for the Objects A, B and C, used were those with different shapes and colors. The Objects A, B and C particularly have the following shapes and color.

Object A: A shape composed of a base portion (green) stretched horizontally and an extension portion (green) stretched vertically from the center of the base portion and provided with T shaped form in the front view. The base and extension portions each are in cuboid form.

Object B: the same shape as the Object A except that a base portion color is yellow and an extension portion is in columnar form and its color is red.

Object C: the same shape as the Object A except that a base portion color is yellow and an extension portion is cut out to circular arc form in the lateral front view and is yellow.

Objects A, B and C were placed such that their base portions were in contact with the bottom of the test cage and their extension portions were stretched upwardly.

3) Statistical Analysis

In the acquisition trial, the rate of access time to the Object B to total access time to the Objects A and B (access rate to Object B) was calculated. When the acquisition trial was carried out, the Objects A and B were unknown objects and therefore, an amount of access time to each of the both was expected to be comparable levels. When an amount of access time to each of the both was disproportionally high on either one, cognition function, etc. was possibly impaired due to a drug administration and therefore, an estimation was considered to be impossible in the experiment. In the test trial, the rate of access time to the Object C to total access time to the Objects A and C (access rate to Object C) was calculated. When the test trial was carried out, the object C was only an unknown object and therefore, disproportional amount of access time to the Object C was expected when memory of the Object A was acquired. As described above, the calculated access rates to the Object B and to the Object C each was subjected to statistical analysis using one-way analysis of variance. Comparison between groups was performed by Tukey-Kramer HSD test.

4) Results

Figure 15A:
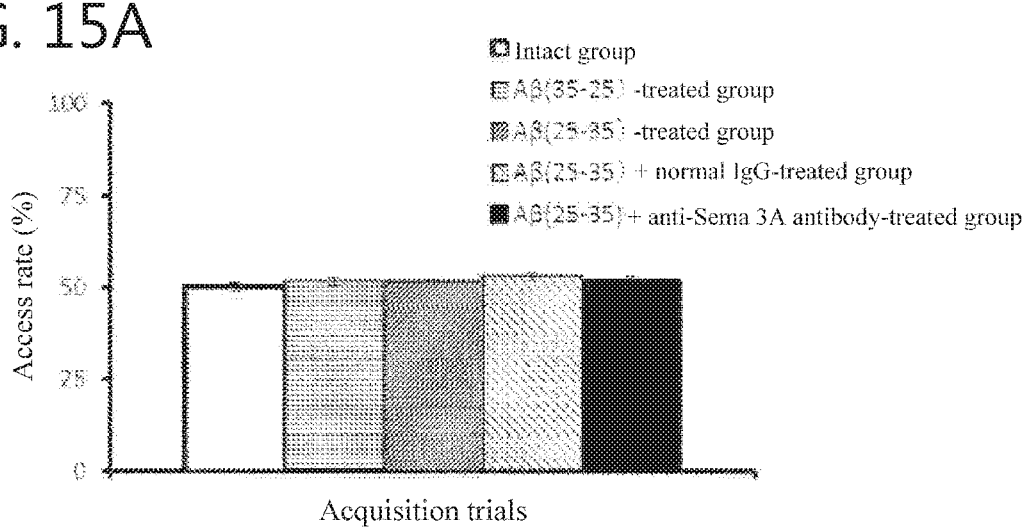
FIGS. 15A and 15B show graphs illustrating results of Example 10.

The obtained results are shown in FIGS. 15A (acquisition trial) and 15B (test trial).

Figure 15B:
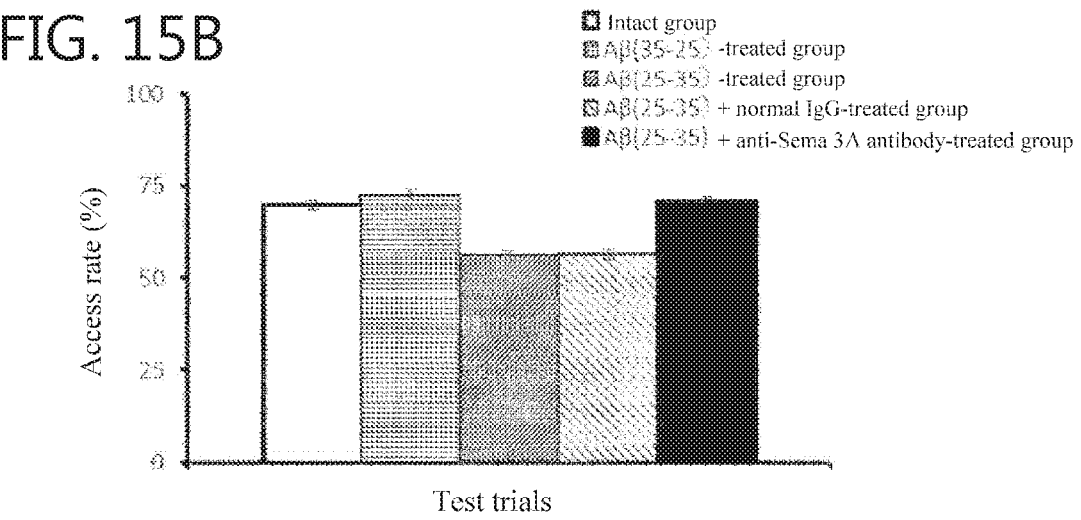

As apparently shown in FIG. 15A, the access rates to Object B in all groups was substantially about 50% in the acquisition trial and no significant differences were observed between all groups. Thus, impairment of cognitive function was not observed, suggesting that estimation of memory acquisition in the experiment was possible. On the other hand, as shown in FIG. 15B, Intact group and Aβ (35-25)-treated group (negative control) each had about 75% of access rate to the Object C in test trial. However, Aβ (25-35)-treated group had only about 50% of access rate to the Object C, resulting in significant decrease of preference to the Object C compared to Intact group ($p<0.0001$, vs. Intact group). Results reveal that memory of the Object A was not acquired due to impairment of memory caused by Aβ (25-35) administration.

Furthermore, as apparently shown in FIG. 15B, Aβ (25-35)+anti-Sema 3A antibody-treated group had about 75% of access rate to the object C, resulting in significant recovery compared to Aβ (25-35)-treated group and Aβ (25-35)+ normal IgG-treated group ($p<0.0001$, vs. Aβ (25-35)-treated group or Aβ (25-35)+normal IgG-treated group).

These results demonstrate that anti-Sema 3A antibody containing CDRs having specific amino acid sequences exhibits effects to inhibit memory impairment induction induced with Aβ. Increased expression level of Sema 3A protein has been already observed in the postmortem brain in a patient with Alzheimer's disease, and Collapsin Response Mediator Protein (CRMP), which is phosphate-modified in Sema 3A signaling pathway, is known to be highly phosphate-modified CRMP in neurofibrillary tangle, a lesion of Alzheimer's disease. Accordingly, such drug efficacy is considered to be due to blocking of Sema 3A-CRMP signal via anti-Sema 3A antibody.

Example 15: Analysis of Effects of Anti-Sema 3A Avian-Mouse Chimeric Antibody on Immune/Inflammatory Diseases Effects of the obtained avian-mouse chimeric antibody in Example 2 on lethal inflammatory condition was analyzed in lipopolysaccharide-inoculated model, a simulated septic condition model.

1) Test Materials 1-1) Lipopolysaccharide

Lipopolysaccharide (hereinafter referred to as LPS, Sigma-Aldrich Japan, Lot No: 032M4082V) was prepared with physiological saline to 6 mg/mL.

1-2) Avian-Mouse Anti-Sema 3A Antibody

The produced anti-Sema 3A avian-mouse chimeric antibody in Example 2 was diluted with physiological saline to 5 mg/mL, which was used as anti-Sema 3A antibody solution.

1-3) Chimeric Antibody for Negative Control

Non-specific avian-mouse chimeric antibody (IgG) (chimeric antibody for negative control), which was produced using an antibody library constructed by chicken B cell-derived DT40 cells, was diluted with physiological saline to 5 mg/mL, which was used as a chimeric antibody solution for negative control.

1-4) Mouse

Male mice aged 6 weeks old (C57BL/6J) purchased from CHARLES RIVER LABORATORIES JAPAN, INC. were used.

2) Test Method

After purchased, C57BL/6J mice were conditioned in a mice rearing room and divided into 5 mice a group and among them, a test group was set as shown in Table 9. Antibodies were administered via tail vein and after 30 minutes, LPS was intraperitoneally inoculated. The day in which these treatments were carried out was set as Day 0 and each mouse was observed to be alive or dead until Day 4, which was used as an indicator of efficacy determination. The same test was carried out total three times to confirm reproducibility.

After three tests were confirmed to be non-dissociative, results obtained from these tests were combined, based on which, determined were improvement effects of survival rate and its efficacy at Day 4. Kaplan-Meiyer method was used to prepare the survival curve, based on which, effects of survival period-extension were determined.

TABLE 9

| Group | Administration conditions |
| --- | --- |
| Negative control group (N = 5) | Chimeric antibody solution for negative control was administered in an amount of 0.1 mL (500 µg of dose of chimeric antibody for negative control) via tail vein and after 30 minutes, LPS was intraperitoneally inoculated to 60 mg/kg of dose. |
| Anti-Sema 3A avian-mouse chimeric antibody-treated group (N = 5) | Anti-Sema 3A antibody solution was administered in an amount of 0.1 mL (500 µg of dose of anti-Sema 3A avian-mouse chimeric antibody) via tail vein and after 30 minutes, LPS was intraperitoneally inoculated to 60 mg/kg of dose. |

3) Statistical Analysis

In the case of being dead earlier than Day 4 after administration, the survival period-extension was not confirmed (no effective) and in the case of being alive until Day 4, the survival period-extension was confirmed (effective). From these binarized values, consistency among the three tests was determined by Breslow-Day test and then, the difference of efficacy rate obtained by combining the three tests was determined by Cochran-Mantel-Haenzel test. Log-rank test was performed to determine effects of the survival period-extension.

4) Results

The obtained results are shown in Table 10. As apparently shown in Table 10, in all three tests, the survival rate of anti-Sema 3A avian-mouse chimeric antibody-treated group was superior than that of non-specific sequence chimeric antibody-treated group, a negative control. Bresslow-Day test, which was performed for confirmation of non-dissociative among these tests, does not indicate significance and therefore, the three tests are confirmed to be non-dissociative (p=0.6202). On that basis, results of the three tests were combined, based on which, Cochran-Mantel-Haenzel test was performed and in addition to P=0.0364, statistical significance difference is observed at 5% level of significance on the survival rate between the negative control group and the anti-Sema 3A avian-mouse chimeric antibody group. These results reveal that anti-Sema 3A avian-mouse chimeric antibody exhibits effects to improve the survival rate of model animals with lethal inflammatory condition and the effects indicate reproducibility.

TABLE 10

| | Group | Number of mouse | Dead | Alive | Survival rate |
| --- | --- | --- | --- | --- | --- |
| Test I | Negative control | N = 5 | 3 | 2 | 40% |
| | Anti-Sema 3A chimeric antibody | N = 5 | 2 | 3 | 60% |
| Test II | Negative control | N = 5 | 4 | 1 | 20% |
| | Anti-Sema 3A chimeric antibody | N = 5 | 1 | 4 | 80% |
| Test III | Negative control | N = 5 | 4 | 1 | 20% |
| | Anti-Sema 3A chimeric antibody | N = 5 | 2 | 3 | 60% |
| Combined three tests | Negative control | N = 15 | 11 | 4 | 26.7% |
| | Anti-Sema 3A chimeric antibody | N = 15 | 5 | 10 | 66.7% |

Figure 16:
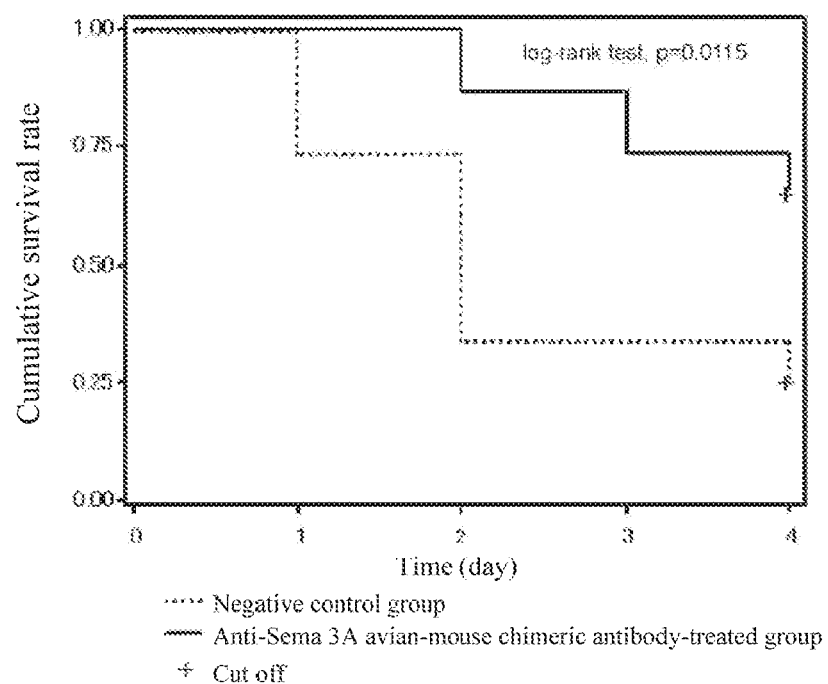
FIG. 16 shows a diagram illustrating results of Example 15. The figure is a combined plot of survival curves of three tests of the administration of anti-Sema 3A avian-mouse chimeric antibody by Kaplan-Meier method.

The survival curve of the combined three tests was prepared by Kaplan-Meier method and log-rank test was performed to determine the significance. Results are shown in FIG. 16. As shown in FIG. 16, analysis of the survival period-extension also indicates significance, i.e. p=0.0115, and reveals that anti-Sema 3A avian-mouse chimeric antibody exhibits effects of survival period-extension.

Example 16: Analysis of Effect of Anti-Sema 3A Humanized Antibody on Immune/Inflammatory Diseases Effects of the obtained anti-Sema 3A humanized antibody in Example 2 on LPS-induced inflammatory disease model was also analyzed in the same manner as Example 12.

1) Test Materials 1-1) LPS

Preparation of LPS was carried out in the same manner as Example 15.

1-2) Anti-Sema 3A Humanized Antibody

The produced anti-Sema 3A humanized antibody (Humanized-2) in Example 2 was diluted with physiological saline to obtain a solution of anti-Sema 3A humanized antibody. In anti-Sema 3A humanized antibody 500 µg-treated group, anti-Sema 3A humanized antibody (Humanized-2) was prepared to 5 mg/mL and in anti-Sema 3A humanized antibody 100 µg-treated group, anti-Sema 3A humanized antibody (Humanized-2) was prepared to 1 mg/mL, for use herein.

1-3) Human Antibody for Negative Control

Non-specific human polyclonal antibody (human IgG POLYCLONAL Isotype Control; BioXCell, # BE0092) was diluted with physiological saline to 5 mg/mL, which was used as a solution of human antibody for negative control.

1-4) Mouse

Male mice aged 6 weeks old (C57BL/6J) purchased from CHARLES RIVER LABORATORIES JAPAN, INC. were used.

2) Test Method

After purchased, C57BL/6J mice were conditioned in a mouse rearing room and divided into 10 mice a group and among them, test groups were set as shown in Table 11. Antibodies were administered via tail vein and after 30 minutes, LPS was intraperitoneally inoculated. The day in which these treatments were carried out was set as Day 0 and each mouse was observed to be alive or dead until Day 4, which was used as an indicator of efficacy determination.

TABLE 11

| Group | Administration conditions |
| --- | --- |
| Negative control group (N = 10) | A solution of human antibody for negative control was administered in an amount of 0.1 mL (500 µg of dose of human antibody for negative control) via tail vein and after 30 minutes, LPS was intraperitoneally inoculated to 60 mg/kg of dose. |
| Anti-Sema 3A humanized antibody 100 µg-treated group (N = 10) | A solution of anti-Sema 3A humanized antibody was administered in an amount of 0.1 mL (100 µg of dose of anti-Sema 3A humanized antibody) via tail vein and after 30 minutes, LPS was intraperitoneally inoculated to 60 mg/kg of dose. |
| Anti-Sema 3A humanized antibody 500 µg-treated group (N = 10) | A solution of anti-Sema 3A humanized antibody was administered in an amount of 0.1 mL (500 µg of dose of anti-Sema 3A humanized antibody) via tail vein and after 30 minutes, LPS was intraperitoneally inoculated to 60 mg/kg of dose. |

3) Statistical Analysis

The binarized survival rates of no effective and effective values in the same manner as Example 12 were subjected to one-sided Cochran-Armitage test to determine dose reactivity relative to improvement effects of the survival rate, wherein the following three dose reactivity types were supposed: linear increasing type, low dose-saturation type and high dose-rising type, and contrasts of these types were predetermined. Log-rank test was performed to determine effects of the survival period-extension.

4) Results

Survival rates of each group are shown in Table 12. In anti-Sema 3A humanized antibody 100 µg-treated group, the survival rate was twice (60%) as the negative control group (30%) and in anti-Sema 3A humanized antibody 500 µg-treated group, the survival rate was observed to be higher (80%) than that of the 100 µg-treated group. In each of both anti-Sema 3A humanized antibody-treated groups, survival rates were improved and dose-dependent trend was found.

TABLE 12

| Group | Number of mouse | Dead | Alive | Survival rate |
| --- | --- | --- | --- | --- |
| Negative control group | N = 10 | 7 | 3 | 30% |
| Anti-Sema 3A humanized antibody 100 µg-treated group | N = 10 | 4 | 6 | 60% |
| Anti-Sema 3A humanized antibody 500 µg-treated group | N = 10 | 2 | 8 | 80% |

These results apparently show that anti-Sema 3A humanized antibody also suppresses LPS-induced lethal inflammatory condition and exhibits effects to improve the survival rate similarly to anti-Sema 3A avian-mouse chimeric antibody shown in Example 15.

Example 17: Analysis of Effects of Anti-Sema 3A Humanized Antibody on Lethal Inflammatory Diseases after the Onset From the obtained results in Example 16, effects of anti-Sema 3A humanized antibody was determined in the case where LPS was inoculated before the onset and its treatment was made after the onset.

1) Test Material 1-1) LPS

Preparation of LPS was carried out in the same manner as Example 15.

1-2) Anti-Sema 3A Humanized Antibody

The produced anti-Sema 3A humanized antibody (Humanized-2) in Example 2 was diluted with physiological saline to obtain an anti-Sema 3A humanized antibody solution. In each of anti-Sema 3A humanized antibody 500 µg, 250m and 125 µg-treated groups, anti-Sema 3A humanized antibody (Humanized-2) was prepared to 5, 2.5 and 1.25 mg/mL, respectively, for use herein.

1-3) Human antibody for negative control

A solution of human antibody for negative control was prepared in the same manner as Example 16.

1-4) Mouse

Male mice aged 6 weeks old (C57BL/6J) purchased from CHARLES RIVER LABORATORIES JAPAN, INC. were used.

2) Test Method

After purchased, C57BL/6J mice were conditioned in a mouse rearing room and divided into 10 mice a group and among them, test groups were set as shown in Table 13. In the test, differently from Examples 15 and 16, actual medical care-based use was supposed and therefore, efficacy determination was made in administrating after inflammatory condition had already induced. Firstly, LPS was intraperitoneally inoculated to induce inflammatory reaction. Antibodies were administered via tail vein one hour after intraperitoneal inoculation of LPS. The day in which these treatments were made was set as Day 0 and each mouse was observed to be alive or dead until Day 4, which was used as an indicator of efficacy determination.

TABLE 13

| Group | Administration conditions |
| --- | --- |
| Negative control group (N = 10) | LPS was intraperitoneally inoculated to 60 mg/kg of dose and after one hour, a solution of human antibody for negative control was administered in an amount of 0.1 mL (500 µg of dose of a solution of human antibody for negative control) via tail vein. |
| Anti-Sema 3A humanized antibody 125 µg-treated group (N = 10) | LPS was intraperitoneally inoculated to 60 mg/kg of dose and after one hour, an anti-Sema 3A humanized antibody solution was administered in an amount of 0.1 mL (125 µg of dose of anti-Sema 3A humanized antibody) via tail vein. |
| Anti-Sema 3A humanized antibody 250 µg-treated group (N = 10) | LPS was intraperitoneally inoculated to 60 mg/kg of dose and after one hour, an anti-Sema 3A humanized antibody solution was administered in an amount of 0.1 mL (250 µg of dose of anti-Sema 3A humanized antibody) via tail vein. |
| Anti-Sema 3A humanized antibody 500 µg-treated group (N = 10) | LPS was intraperitoneally inoculated to 60 mg/kg of dose and after one hour, an anti-Sema 3A humanized antibody solution was administered in an amount of 0.1 mL (500 µg of dose of anti-Sema 3A humanized antibody) via tail vein. |

3) Statistical Analysis

In dose reactivity types which were indicated by 4 groups containing negative control group, the following 7 types were supposed: (1) observed dose-linear regression, (2) linear increasing, (3) middle dose-rising, (4) high dose-rising, (5) middle dose-saturation, (6) low dose-saturation and (7) middle dose-rising and saturation types. Cochran-Armitage test was applied to all of the 7 reaction patterns and p-values, which were multiple-adjusted by sorting and re-extraction method, were calculated and among the calculated p-values, a contrast reactivity type with the smallest p-value was adopted as an optimal dose reactivity type. Log-rank test was performed to determine effects of the survival period-extension.

4) Results

Survival rates of each group of Day 4 after administration are shown in Table 14. In the negative control group, the survival rate was 10%, however, in respective groups treated with 125, 250 and 500 µg of anti-Sema 3A humanized antibody one hour after LPS inoculation, survival rates were 30, 40 and 100%, respectively. Accordingly, trend was observed in which a survival rate increases as a dose increases. In particular, in anti-Sema 3A humanized antibody 500 µg-treated group, surprising effects were observed in which all 10 mice were alive.

TABLE 14

| Group | Number of mouse | Dead | Alive | Survival rate |
|---|---|---|---|---|
| Negative control group | N = 10 | 9 | 1 | 10% |
| Anti-Sema 3A humanized antibody 125 µg-treated group | N = 10 | 7 | 3 | 30% |
| Anti-Sema 3A humanized antibody 250 µg-treated group | N = 10 | 6 | 4 | 40% |
| Anti-Sema 3A humanized antibody 500 µg-treated group | N = 10 | 0 | 10 | 100% |

The 7 dose reactivity types, which were supposed to be indicated by the binarized survival rates, were predetermined and subjected to Cochran-Armitage test multiple-adjusted by sorting and re-extraction method. Results of the calculated p-values are shown in Table 15. Note that unnecessarily-multitudes of digit numbers are provided in order to express the rank order of p-values.

TABLE 15

| Dose-reaction patterns | Multiple-adjusted p-values |
|---|---|
| Observed dose-linear regression type | 0.00001790 |
| Linear increasing type | 0.00004540 |
| Middle dose-rising type | 0.00005730 |
| High dose-rising type | 0.00008040 |
| Middle dose-saturation type | 0.00133730 |
| Middle dose-rising and saturation type | 0.00252090 |
| Low dose-saturation type | 0.01135610 |

As analytical results, results were obtained that all of the supposed dose-reaction types indicated significance. Dose-reaction type with the smallest p-value was the observed dose-linear increasing type (p=0.00001790), one with the second smaller p-value was the linear increasing type (p=0.0000454), followed by middle dose-rising type (p=0.00005730) and high dose-rising type (p=0.00008040) in this order. These results reveal that obvious dose-dependency was scientifically indicated for effects of survival rate improvement in the test as well as anti-Sema 3A humanized antibody had efficacy to control lethal inflammatory condition and to be able to improve the survival rate.

Figure 17:
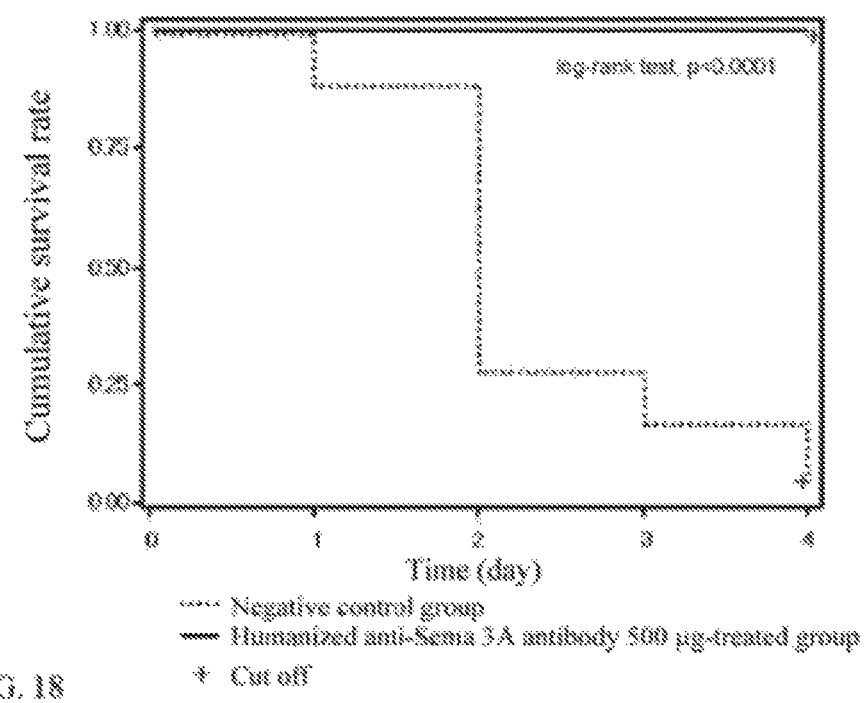
FIG. 17 shows a diagram illustrating results of Example 17. The figure is a plot of survival curves of administered group of anti-Sema 3A humanized antibody of 500 μg one hour after a lipopolysaccharide-inoculated mouse presented inflammatory condition and negative control group by Kaplan-Meier method.

FIG. 17 shows the survival curve of anti-Sema 3A humanized antibody 500 µg-treated group, all cases of which were alive and which exhibited obvious effects of survival rate improvement. In log-rank test, results were obtained that significance level with p<0.0001 was satisfied. There is obviously found that anti-Sema 3A humanized antibody controls lethal inflammatory condition even after the onset of the condition and exhibits effects on the extension of the survival period.

Example 18: Effects of Anti-Sema 3A Humanized Antibody on Disseminated Intravascular Coagulation Model Mouse Disseminated intravascular coagulation (hereinafter, referred to as DIC) associated with sepsis, solid tumor, etc. causes increase of blood level of plasminogen activator inhibitor-1 (hereinafter, referred to as PAI-1) thereby to suppress the action of fibrinolytic system, leading to development of multiple organ failure with serious conditions. There is believed that suppression of increase of blood level of PAI-1 can lead to inhibition of the progression of DIC and therefore, effects of anti-Sema 3A humanized antibody on blood level of PAI-1 were examined.

1) Test Material 1-1) LPS

LPS (Sigma-Aldrich Japan, Lot No: 102M40I 7V) was prepared with physiological saline to a concentration of 1.5 mg/mL.

1-2) Anti-Sema 3A Humanized Antibody

The produced anti-Sema 3A humanized antibody (Humanized-2) in Example 2 was prepared with physiological saline to a concentration of 5 mg/mL.

1-3) Mouse

Male mice aged 6 weeks old (C57BL/6J) purchased from CHARLES RIVER LABORATORIES JAPAN, INC. were used.

2) Test Method 2-1) Grouping

After purchased, C57BL/6J mice were conditioned in a mouse rearing room and divided into 5 mice a group and among them, test groups were set as shown in Table 16.

2-2) LPS Inoculation and Antibody Administration

LPS was intraperitoneally inoculated so as to be inoculated in an amount of 15 mg/kg. 0.1 mL of 5 mg/mL solution of the antibody solution was administered via tail vein so as to be inoculated in an amount of 500 µg/mouse. Note that Condition-1 group in which LPS was not inoculated was intraperitoneally inoculated with physiological saline.

2-3) Measurement of Mouse PAI-1

Plasma was collected at 1.5, 3 and 9 hours after LPS inoculation to measure blood levels of PAI-1 in the treated animal using mouse PAI-1 ELISA kit (Innovative Research, Inc).

TABLE 16

| | LPS (mg/kg) | Antibody-treated (500 µg) | Blood collecting time |
|---|---|---|---|
| Condition 1 | — | — | Test starting time |
| Condition 2 | 15 | — | 1.5 hr after LPS inoculation |
| Condition 3 | 15 | 30 min before LPS inoculation | 1.5 hr after LPS inoculation |
| Condition 4 | 15 | 1 hr after LPS inoculation | 1.5 hr after LPS inoculation |
| Condition 5 | 15 | — | 3 hr after LPS inoculation |
| Condition 6 | 15 | 30 min before LPS inoculation | 3 hr after LPS inoculation |
| Condition 7 | 15 | 1 hr after LPS inoculation | 3 hr after LPS inoculation |
| Condition 8 | 15 | — | 9 hr after LPS inoculation |
| Condition 9 | 15 | 30 min before LPS inoculation | 9 hr after LPS inoculation |
| Condition 10 | 15 | 1 hr after LPS inoculation | 9 hr after LPS inoculation |

3) Statistical Analysis

For antibody-untreated and antibody-treated groups, two-tailed Student's t test was performed to calculate p-value and the p-value was evaluated to indicate statistical significance in the case of the significance level of 5% or lower.

4) Results

Figure 18:
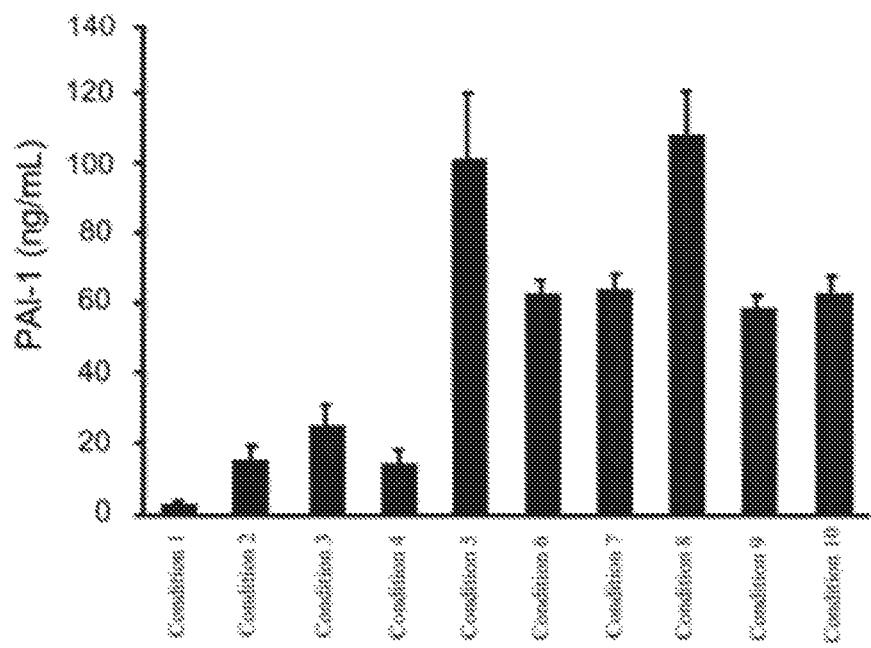
FIG. 18 shows a diagram illustrating results of Example 18. The figure is a diagram illustrating measured results of blood levels of plasminogen activator inhibitor-1 of mice for determining effects of anti-Sema 3A humanized antibody in disseminated intravascular coagulation-model mice.

FIG. 18 shows the measured results of blood levels of PAI-1. In LPS-untreated group (Condition 1), the blood level of PAI-1 was very low, but the blood level of PAI-1 after LPS inoculation indicated to gradually increase after 1.5 hours and significantly increased 3 and 9 hours after LPS inoculation compared to the LPS-untreated animal (Conditions 2, 5 and 8).

In antibody-treated after 3 hours of LPS inoculation group, both of antibody-treated before LPS inoculation group (Condition 6, p=0.0027) and antibody-treated after LPS inoculation group (Condition 7, p=0.0051) suppressed increase of blood levels of PAI-1 compared to the antibody-untreated group. This effect of suppressing increase of PAI-1 by anti-Sema 3A humanized antibody persisted even 9 hours after LPS inoculation and resulted in suppressing increase of blood levels of PAI-1 in both of antibody-treated before LPS inoculation group (Condition 9, p<0.0001) and antibody-treated after LPS inoculation group (Condition 10, p=0.0029) similarly to that of antibody-treated 3 hours after LPS inoculation group.

These results reveal that the produced anti-Sema 3A humanized antibody (humanized-2) in Example 2 has the action of suppressing the increase of blood level of PAI-1, which is one of aggravating factors of DIC.

Example 19: Effects of Anti-Sema 3A Humanized Antibody on Migration Ability of Cancer Cells Disseminated and distal metastases caused after surgical treatment or remission induction by chemical therapy are known to greatly decrease the survival rate of a cancer patient. Activation of migration ability of cancer cells allows to release cancer cells from primary tumor, resulting in disseminated and distal metastases and therefore, effects of anti-Sema 3A humanized antibody on malignant alteration of cancer cells induced by Sema 3A was examined.

1) Test Method

The produced anti-Sema 3A humanized antibody (Humanized-2) in Example 2 was used to evaluate effects on migration ability of cancer cells, which is induced by Sema 3A. Herein, cells of pancreatic cancer in which patients with high Sema 3A expression level have poor outcome were used to examine the effects. Particular experimental process was carried out as follows.

Fibronectin was diluted with PBS buffer to 0.1 mg/mL to prepare a fibronectin diluent and 10 µL of the fibronectin diluent was applied on a lower surface of a filter in a 24 well-type chamber (chemotaxicell chamber manufactured by KURABO INDUSTRIES LTD. 8 µm pore) and the filter was left to stand and dried at room temperature for one hour, a migration chamber provided with which was prepared.

Subsequently, the prepared migration chamber was set in a 24 well plate, to the outer layer of which was added 600 µL of DMEM medium containing 0.1% fetal bovine serum. To the inner layer of the chamber were added $2 \times 10^5$ cells/mL of human pancreatic cancer cell line (MIAPaCa-2) and 200 µL of serum-free DMEM medium containing additive components shown in Table 17, which was cultivated in the presence of 5% $CO_2$ at 37° C. for 4 hours. Subsequently, the chamber was removed and cancer cells in the inner layer of the chamber were drawn and removed. Furthermore, the residual cells in the chamber were removed using a cotton swab wetted with PBS buffer. Then, the chamber was immersed with a cell staining solution (Diff-Quick, SYSMEX INTERNATIONAL REAGENTS CO., LTD) for 10 minutes or more, followed by washing twice with ultrapure water and drying. After drying, cell counts migrated to the lower surface of the chamber filter were measured by a microscope.

TABLE 17

| | Final concentration of additive components in inner layer of chamber | | |
|---|---|---|---|
| | Human Sema 3A/Fc (ng/mL) | Anti-Sema 3A humanized antibody (Humanized-2) obtained in Example 2 (µg/mL) | Negative control human antibody (µg/mL) |
| Condition 1 | — | — | — |
| Condition 2 | 100 | — | — |
| Condition 3 | 100 | 0.1 | — |
| Condition 4 | 100 | 1 | — |
| Condition 5 | 100 | 10 | — |
| Condition 6 | 100 | — | 0.1 |
| Condition 7 | 100 | — | 1 |
| Condition 8 | 100 | — | 10 |

2) Statistical Analysis

With consideration for multiplicity, two-sided Dunnett's test was applied to Conditions 3 to 5 and Conditions 6 to 8 relative to Condition 2 to calculate p-values and when the p-values were significance level of 5% or lower, they were evaluated to indicate statistical significance.

3) Test Results

Figure 19:
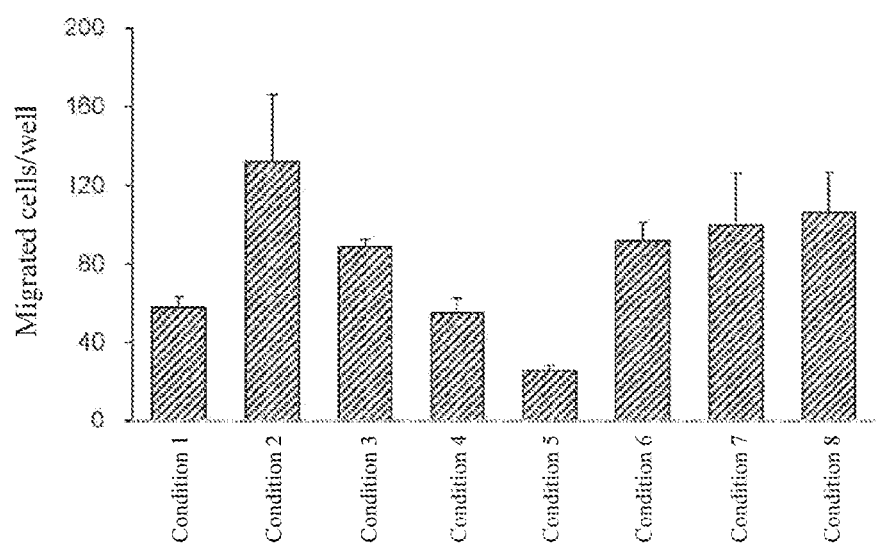
FIG. 19 shows a graph illustrating results of Example 19. The figure shows analyzed results of effects of Sema 3A protein and/or anti-Sema 3A humanized antibody for cell migration ability in human pancreatic cancer cells (MIAPaCa-2).

The obtained results are shown in FIG. 19. A migration activity of pancreatic cancer cell MIAPaCa-2 stimulated by human Sema 3A was enhanced two times or more (Condition 2). However, a migration activity of pancreatic cancer cells induced by Sema 3A was suppressed in the presence of anti-Sema 3A humanized antibody (Conditions 3 to 5). In anti-Sema 3A antibody 1 µg/ml-treated group (P=0.0031) and 10 µg/ml-treated group (P<0.001), migration of cancer cells were suppressed to the same level as Sema 3A-untreated group (Condition 1). On the other hand, in negative control group, cancer cell migration induced by Sema 3A was not suppressed (Conditions 6 to 8). That is, results reveal that anti-Sema 3A antibody containing CDR having a specific amino acid sequence specifically suppresses pancreatic cancer cell migration induced by Sema 3A.

Example 20: Effects of Anti-Sema 3A Humanized Antibody on Invasion Ability of Cancer Cells Cancer cells having activated migration ability lyse and invade the surrounding extracellular substrates and then destroys basal membrane to transfer to blood and lymph vessels, eventually transferring to distant organs. Suppression of invasion and metastasis of cancer cells leads to suppression of metastatic recurrence and therefore is considered to be useful for survival rate improvement of cancer patients. In addition to suppressing effects on enhancement of Sema 3A-induced migration ability examined in Example 19, effects of anti-Sema 3A humanized antibody on invasion ability of cancer cells was examined.

1) Test Method

Extracellular substrates removed growth factors (Becton, Dickinson and Company, Matrigel (trademark) Growth Factor Redused) was loaded in the inner layer of invasion chamber (Becton, Dickinson and Company, BioCoat (trademark), 8 µm pore, #354483), which was used to evaluate effects of anti-Sema 3A humanized antibody on invasion ability of cancer cells induced by Sema 3A. Particular experimental process was carried out as follows.

For cancer cells, human pancreatic cancer cell line (MIAPaCa-2), human glioblastoma line (U87MG) and mouse-derived lung cancer cell line (3LL) were used. Firstly, the extracellular substrates loaded in an invasion chamber were treated by swelling and then, the invasion chamber was set in a 24 well plate, to the outer layer of which was added 0.75 mL of DMEM medium containing 0.1% fetal bovine serum (1% fetal bovine serum for 3LL cells) and to the inner layer of which was added $2 \times 10^5$ cells/mL of cancer cells and 125 µL of serum-free DMEM medium containing additive components at concentrations shown in Table 18 and the chamber was cultivated in the presence of 5% $CO_2$ at 37° C. for 24 hours. Subsequently, the invasion chamber was removed, followed by removing residual cells in the inner layer of the invasion chamber in the same manner as Example 19 and then, the invaded cell counts, which transferred into the lower surface of the filter, were measured by a microscope.

TABLE 18

Components added to inner layer of invasion chamber

|  | Human Sema 3A (g/mL) | Anti-Sema 3A humanized antibody (Humanized-2) obtained in Example 2 (µg/mL) | Negative control human antibody (µg/mL) |
|---|---|---|---|
| Condition 1 | — | — | — |
| Condition 2 | — | 0.1 | — |
| Condition 3 | — | 1.0 | — |
| Condition 4 | — | 10.0 | — |
| Condition 5 | 100 | — | — |
| Condition 6 | 100 | 0.1 | — |
| Condition 7 | 100 | 1.0 | — |
| Condition 8 | 100 | 10.0 | — |
| Condition 9 | 100 | — | 0.1 |
| Condition 10 | 100 | — | 1.0 |
| Condition 11 | 100 | — | 10.0 |

2) Statistical Analysis

For inhibitory action of Sema 3A-induced invasion activity, with consideration for multiplicity, two-sided Dunnett's test was applied to Conditions 6 to 8 and Conditions 9 to 10 relative to Condition 5 to calculate p-values and when the p-values were significance level of 5% or lower, they were evaluated to indicate statistical significance. A list of p-values is shown in Table 19.

3) Test Results

Figure 20:
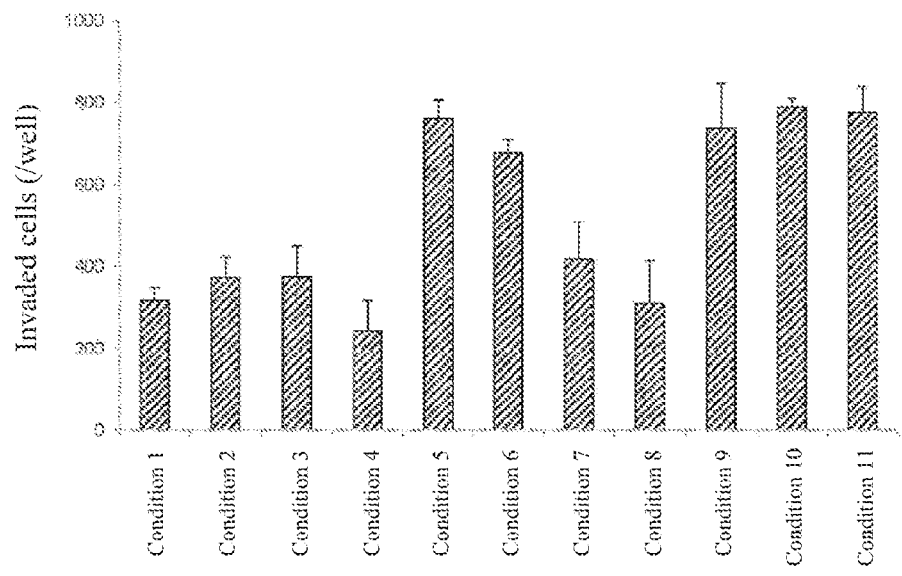
FIG. 20 shows a graph illustrating results of Example 20. The figure shows a graph illustrating results of cell invasion assay with human pancreatic cancer cell line (MIAPaCa-2).
Figure 21:
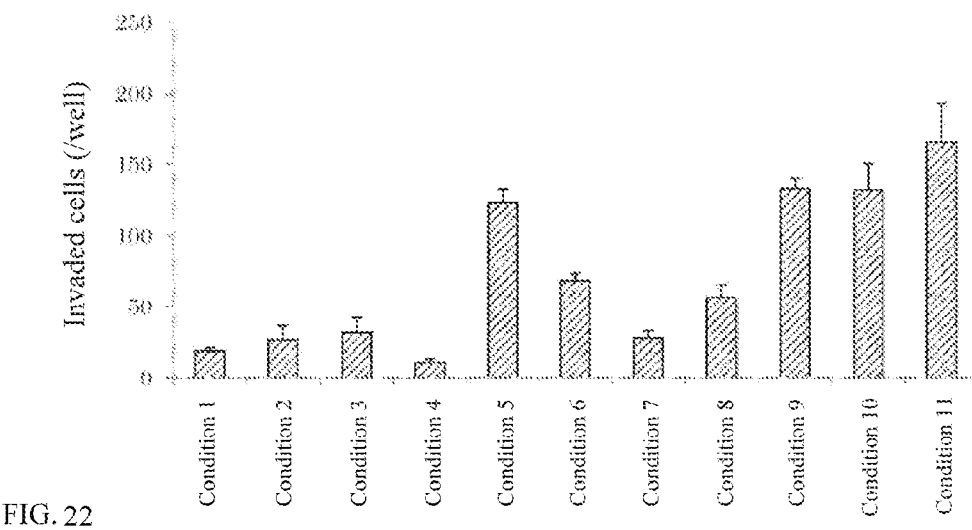
FIG. 21 shows a graph illustrating results of Example 20. The figure shows a graph illustrating results of cell invasion assay with human pancreatoblastoma cell line (U87MG).
Figure 22:
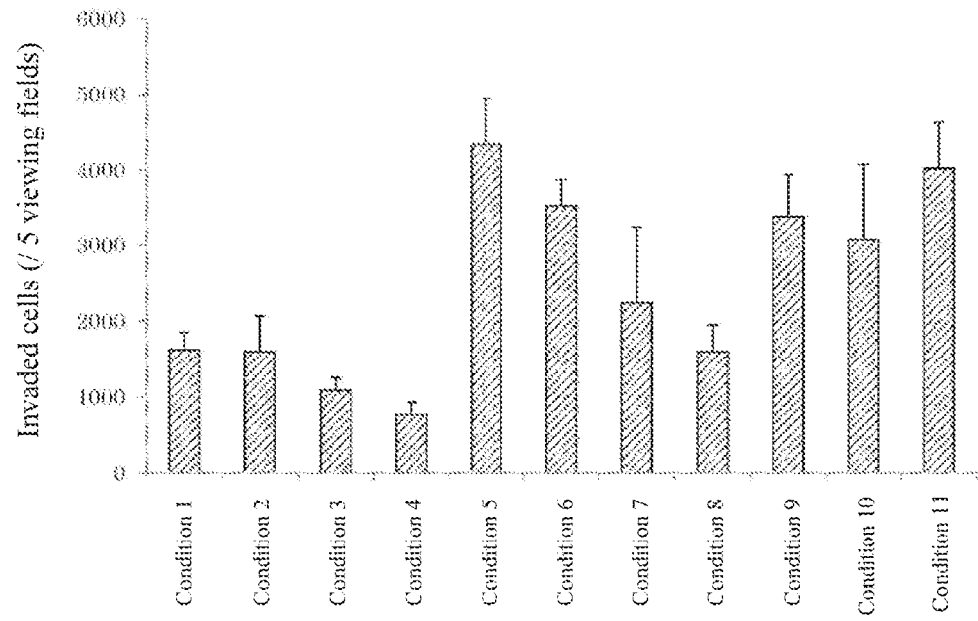
FIG. 22 shows a graph illustrating results of Example 20. The figure shows a graph illustrating results of cell invasion assay with mouse-derived lung cancer cell line (3LL).
Figure 23:
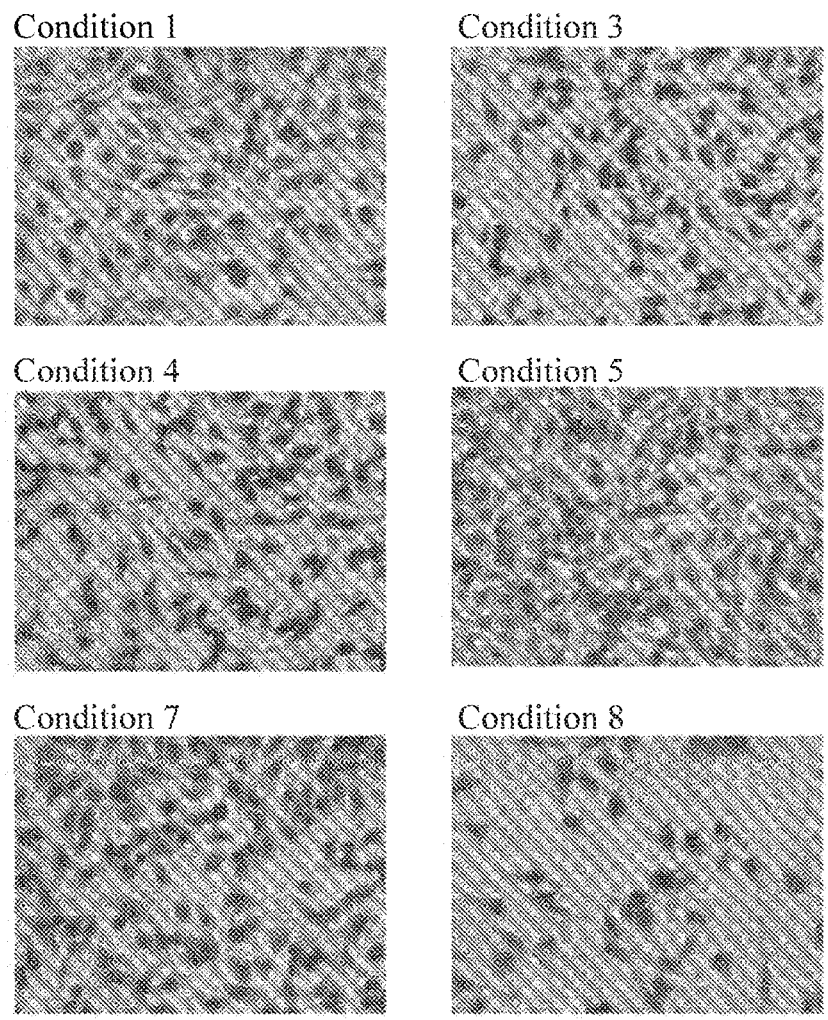
FIG. 23 shows photographic images illustrating results of Example 20. The figure shows microscopic images of invaded cells obtained by staining through cell invasion assay with mouse-derived lung cancer cell line (3LL).

Measured results of invaded cell counts are shown in FIG. 20 for MIAPaCa-2 cells, in FIG. 21 for U87MG cells and in FIG. 22 for 3LL cells under the above-mentioned Conditions. In the case of addition of Sema 3A (Condition 5), all cancer cell lines exhibited obviously-enhanced invasion ability compared to Sema 3A-unstimulated group (Condition 1). In the case of addition of human Sema 3A together with anti-Sema 3A humanized antibody, all cancer cell lines exhibited suppressed invasion to the same extent as Sema 3A-unstimulated group (Conditions 6 to 8). Under non Sema 3A-stimulated condition, surprising invasion-suppressing effects were not observed except 3LL (Conditions 1 to 4). On the other hand, in antibody-containing negative control group, enhancement of cancer cell invasion ability induced by Sema 3A was little suppressed (Conditions 9 to 11). FIG. 23 shows microscopic images of invaded 3LL cells. There are visually observed that in Condition 5 in which Sema 3A was added, cancer cells significantly invaded compared to Condition 1 in which Sema 3A was not added, and in Conditions 7 and 8 in which anti-Sema 3A humanized antibody was treated in the presence of Sema 3A, cancer cell invasion activity induced by Sema 3A was apparently suppressed. As apparently shown in these results, there is revealed that anti-Sema 3A antibody containing a CDR having a specific amino acid sequence has the action of suppressing cancer cell invasion activity induced by Sema 3A to the same extent as Sema 3A-unstimulated group.

TABLE 19

| | Results of Dunnett's test | | |
|---|---|---|---|
|  | MIAPaCa-2 | U87MG | 3LL |
| Condition 6 | p = 0.4339 | p < 0.001 | p = 0.3278 |
| Condition 7 | p = 0.0012 | p < 0.001 | p = 0.0091 |
| Condition 8 | p < 0.001 | p < 0.001 | p = 0.0022 |
| Condition 9 | p = 0.952 | p = 0.8182 | p = 0.302 |
| Condition 10 | p = 0.920 | p = 0.8676 | p = 0.142 |
| Condition 11 | p = 0.987 | p = 0.0046 | p = 0.903 |

Example 21: Effects of Anti-Sema 3A Humanized Antibody on Anticancer Agent-Unresponsiveness Induced by Sema 3A Pancreatic cancer is known to have very low 5 year-survival rate among cancer. The etiology includes: in pancreatic cancer tissue which is in a hypovascular state, the cancer cells can proliferate and develop even in such a nutrient starvation state and often have tolerance for an anticancer agent such as gemcitabine hydrochloride (hereinafter, referred to as GEM). That is, in pancreatic cancer treatment, overcoming unresponsiveness to an anticancer agent is an important subject and therefore, drug-tolerance induced by Sema 3A and removal action of the tolerance by anti-Sema 3A humanized antibody in the nutrient starvation state were evaluated.

1) Test Method

In a nutrient starvation state characteristic of pancreatic cancer, effects of humanized anti-Sema 3A antibody (the produced humanized-2 in Example 2) on GEM-unresponsiveness induced by Sema 3A was evaluated. Particular experimental process was carried out as follows.

A cell suspension in which $4 \times 10^4$ cells/mL of human pancreatic cells (MIAPaCa-2) was suspended in DMEM medium containing 10% fetal bovine serum was seeded into each well of a 96 well plate in an amount of 100 µL for each one. The plate was cultivated in the presence of 5% $CO_2$ at 37° C. for 24 hours and then the medium was replaced with 100 µL of DMEM medium containing 0.1% fetal bovine serum, followed by cultivation for another 24 hours. Subsequently, to each well was added 100 µL of DMEM medium containing 0.1% fetal bovine serum with given amounts of components shown in Table 20, followed by cultivation for 2 days. Then, the culture supernatant was removed from each well in an amount of 100 µL and to each well was added CellTiter reagent (CellTiter AQueous One Solution Proliferation Assay; Promega) of 20 µL followed by cultivation in the presence of 5% $CO_2$ at 37° C. for one hour and then the absorbance was measured at 490 nm.

TABLE 20

Final concentration of components in each well

| | Human Sema 3A/Fc (ng/mL) | Gemcitabine hydrochloride (nM) | Anti-Sema 3A humanized antibody (Humanized-2) obtained in Example 2 (μg/mL) | Negative control human antibody (μg/mL) |
|---|---|---|---|---|
| Condition 1 | — | — | — | — |
| Condition 2 | — | 10 | — | — |
| Condition 3 | 100 | 10 | — | — |
| Condition 4 | 100 | 10 | 0.1 | — |
| Condition 5 | 100 | 10 | 1 | — |
| Condition 6 | 100 | 10 | 10 | — |
| Condition 7 | 100 | 10 | — | 0.1 |
| Condition 8 | 100 | 10 | — | 1 |
| Condition 9 | 100 | 10 | — | 10 |

2) Statistical Analysis

With consideration for multiplicity, two-sided Dunnett's test was applied to Conditions 4 to 6 and Conditions 7 to 9 relative to Condition 3 to calculate p-values and when the p-values were significance level of 5% or lower, they were evaluated to indicate statistical significance. The p-values are shown in Table 21.

3) Test Results

Figure 24:
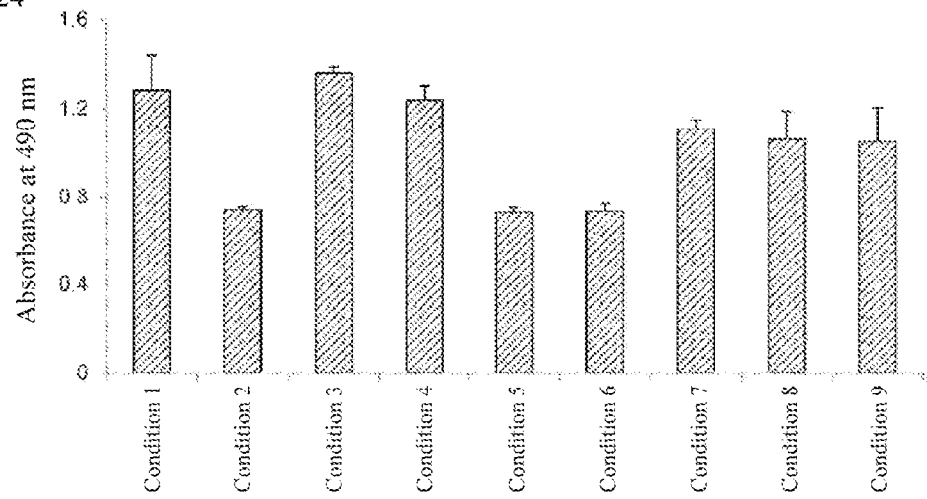
FIG. 24 shows a graph illustrating results of Example 21. The figure shows analyzed results of effect of Sema 3A protein and/or anti-Sema 3A humanized antibody on sensitivity to gemcitabine hydrochloride in human pancreatic cancer cells (MIAPaCa-2).

FIG. 24 shows results of assessment of pancreatic cell proliferation. GEM suppressed proliferation of pancreatic cells (Condition 2 relative to Condition 1), however, human Sema 3A reduced sensitivity to GEM and induced drug-unresponsiveness (Condition 3 relative to Condition 2). The GEM tolerance induced by Sema 3A was removed with anti-Sema 3A humanized antibody of 1 or 10 μg/ml. and GEM sensitivity was recovered to the same extent as a condition in the absence of Sema 3A (Conditions 4 to 6 relative to Condition 3). On the other hand, human antibody-containing negative control group was not able to recover GEM sensitivity to the same extent as a condition in the absence of Sema 3A (Conditions 7 to 9). Results reveal that the produced humanized anti-Sema 3A antibody in Example 2 has ability to remove anticancer agent tolerance induced by Sema 3A in such a nutrient starvation as pancreatic cancer tissue.

TABLE 21

| Antibody concentration μg/mL | Results of Dunnett's test | |
|---|---|---|
| | Anti-Sema 3A humanized antibody | Negative control human antibody |
| 0.1 | p = 0.0150 | p = 0.0414 |
| 1 | p < 0.001 | p = 0.0179 |
| 10 | p < 0.001 | p = 0.0147 |

Sequence Listing Free Text

SEQ ID NO: 1 is the amino acid sequence of heavy chain CDR1 of avian-mouse chimeric antibody (clone No. 4-2 strain-derived).

SEQ ID NO: 2 is the amino acid sequence of heavy chain CDR2 of avian-mouse chimeric antibody (clone No. 4-2 strain-derived).

SEQ ID NO: 3 is the amino acid sequence of heavy chain CDR3 of avian-mouse chimeric antibody (clone No. 4-2 strain-derived).

SEQ ID NO: 4 is the amino acid sequence of light chain CDR1 of avian-mouse chimeric antibody (clone No. 4-2 strain-derived).

SEQ ID NO: 5 is the amino acid sequence of light chain CDR2 of avian-mouse chimeric antibody (clone No. 4-2 strain-derived).

SEQ ID NO: 6 is the amino acid sequence of light chain CDR3 of avian-mouse chimeric antibody (clone No. 4-2 strain-derived).

SEQ ID NO: 7 is the amino acid sequence of heavy chain variable region of avian-human chimeric antibody (clone No. 4-2 strain-derived).

SEQ ID NO: 8 is the amino acid sequence of heavy chain variable region of avian-human chimeric antibody (clone No. 4-2 strain-derived).

SEQ ID NO: 9 is the amino acid sequence of light chain variable region of avian-human chimeric antibody (clone No. 4-2 strain-derived).

SEQ ID NO: 10 is the amino acid sequence of light chain variable region of avian-human chimeric antibody (clone No. 4-2 strain-derived).

SEQ ID NO: 11 is the amino acid sequence of heavy chain variable region of humanized antibody (clone No. 4-2 strain-derived).

SEQ ID NO: 12 is the amino acid sequence of light chain variable region of humanized antibody (Humanized-1) (clone No. 4-2 strain-derived).

SEQ ID NO: 13 is the amino acid sequence of light chain variable region of humanized antibody (Humanized-2) (clone No. 4-2 strain-derived).

SEQ ID NO: 14 is the nucleotide sequence encoding the amino acid sequence (SEQ ID NO: 7) of heavy chain variable region of avian-human chimeric antibody (clone No. 4-2 strain-derived).

SEQ ID NO: 15 is the nucleotide sequence encoding the amino acid sequence (SEQ ID NO: 8) of heavy chain variable region of avian-human chimeric antibody (clone No. 4-2 strain-derived).

SEQ ID NO: 16 is the nucleotide sequence encoding the amino acid sequence (SEQ ID NO: 9) of light chain variable region of avian-human chimeric antibody (clone No. 4-2 strain-derived).

SEQ ID NO: 17 is the nucleotide sequence encoding the amino acid sequence (SEQ ID NO: 10) of light chain variable region of avian-human chimeric antibody (clone No. 4-2 strain-derived).

SEQ ID NO: 18 is the nucleotide sequence encoding the amino acid sequence of heavy chain CDR1 of avian-mouse chimeric antibody (clone No. 4-2 strain-derived).

SEQ ID NO: 19 is the nucleotide sequence encoding the amino acid sequence of heavy chain CDR2 of avian-mouse chimeric antibody (clone No. 4-2 strain-derived).

SEQ ID NO: 20 is the nucleotide sequence encoding the amino acid sequence of heavy chain CDR3 of avian-mouse chimeric antibody (clone No. 4-2 strain-derived).

SEQ ID NO: 21 is the nucleotide sequence encoding the amino acid sequence of light chain CDR1 of avian-mouse chimeric antibody (clone No. 4-2 strain-derived).

SEQ ID NO: 22 is the nucleotide sequence encoding the amino acid sequence of light chain CDR2 of avian-mouse chimeric antibody (clone No. 4-2 strain-derived).

SEQ ID NO: 23 is the nucleotide sequence encoding the amino acid sequence of light chain CDR3 of avian-mouse chimeric antibody (clone No. 4-2 strain-derived).

SEQ ID NO: 24 is the nucleotide sequence encoding the amino acid sequence (SEQ ID NO: 11) of heavy chain variable region of humanized antibody (clone No. 4-2 strain-derived).

SEQ ID NO: 25 is the nucleotide sequence encoding the amino acid sequence (SEQ ID NO: 12) of light chain variable region of humanized antibody (Humanized-1) (clone No. 4-2 strain-derived).

SEQ ID NO: 26 is the nucleotide sequence encoding the amino acid sequence (SEQ ID NO: 13) of light chain variable region of humanized antibody (Humanized-2) (clone No. 4-2 strain-derived).

SEQ ID NO: 27 is the nucleotide sequence of primer-1.
SEQ ID NO: 28 is the nucleotide sequence of primer-2.
SEQ ID NO: 29 is the nucleotide sequence of primer-3.
SEQ ID NO: 30 is the nucleotide sequence of primer-4.
SEQ ID NO: 31 is the nucleotide sequence of primer-5.
SEQ ID NO: 32 is the nucleotide sequence of primer-6.
SEQ ID NO: 33 is the nucleotide sequence of primer-7.
SEQ ID NO: 34 is the nucleotide sequence of primer-8.
SEQ ID NO: 35 is the amino acid sequence of heavy chain of avian-mouse chimeric antibody (clone No. 4-2 strain-derived).

SEQ ID NO: 36 is the amino acid sequence of light chain of avian-mouse chimeric antibody (clone No. 4-2 strain-derived).

SEQ ID NO: 37 is the nucleotide sequence of primer-Aγ.
SEQ ID NO: 38 is the nucleotide sequence of primer-Bγ.
SEQ ID NO: 39 is the nucleotide sequence of primer-Cγ.
SEQ ID NO: 40 is the nucleotide sequence of primer-Dγ.
SEQ ID NO: 41 is the nucleotide sequence of primer-Eγ.
SEQ ID NO: 42 is the nucleotide sequence of primer-Fγ.
SEQ ID NO: 43 is the nucleotide sequence of primer-Gγ.
SEQ ID NO: 44 is the nucleotide sequence of primer-Hγ.
SEQ ID NO: 45 is the nucleotide sequence of primer-Iγ.
SEQ ID NO: 46 is the nucleotide sequence of primer-Jγ.
SEQ ID NO: 47 is the nucleotide sequence of primer-Kγ.
SEQ ID NO: 48 is the nucleotide sequence of primer-Lγ.
SEQ ID NO: 49 is the amino acid sequence of heavy chain of humanized antibodies (Humanized-1 and Humanized-2) (clone No. 4-2 strain-derived).

SEQ ID NO: 50 is the nucleotide sequence encoding the amino acid sequence of heavy chain of humanized antibodies (Humanized-1 and Humanized-2) (clone No. 4-2 strain-derived).

SEQ ID NO: 51 is the amino acid sequence of light chain of humanized antibody (Humanized-1) (clone No. 4-2 strain-derived).

SEQ ID NO: 52 is the nucleotide sequence encoding the amino acid sequence of light chain of humanized antibody (Humanized-1) (clone No. 4-2 strain-derived).

SEQ ID NO: 53 is the amino acid sequence of light chain of humanized antibody (Humanized-2) (clone No. 4-2 strain-derived).

SEQ ID NO: 54 is the nucleotide sequence encoding the amino acid sequence of light chain of humanized antibody (Humanized-2) (clone No. 4-2 strain-derived).

SEQ ID NO: 55 is the amino acid sequence of heavy chain of avian-human chimeric antibody (clone No. 4-2 strain-derived).

SEQ ID NO: 56 is the nucleotide sequence encoding the amino acid sequence of heavy chain of avian-human chimeric antibody (clone No. 4-2 strain-derived).

SEQ ID NO: 57 is the amino acid sequence of light chain of avian-human chimeric antibody (clone No. 4-2 strain-derived).

SEQ ID NO: 58 is the nucleotide sequence encoding the amino acid sequence of light chain of avian-human chimeric antibody (clone No. 4-2 strain-derived).

SEQ ID NO: 59 is the amino acid sequence of heavy chain variable region of avian-mouse chimeric antibody (clone No. 165 strain-derived).

SEQ ID NO: 60 is the amino acid sequence of heavy chain CDR1 of avian-mouse chimeric antibody (clone No. 165 strain-derived).

SEQ ID NO: 61 is the amino acid sequence of heavy chain CDR2 of avian-mouse chimeric antibody (clone No. 165 strain-derived).

SEQ ID NO: 62 is the amino acid sequence of heavy chain CDR3 of avian-mouse chimeric antibody (clone No. 165 strain-derived).

SEQ ID NO: 63 is the amino acid sequence of light chain variable region of avian-mouse chimeric antibody (clone No. 165 strain-derived).

SEQ ID NO: 64 is the amino acid sequence of light chain CDR1 of avian-mouse chimeric antibody (clone No. 165 strain-derived).

SEQ ID NO: 65 is the amino acid sequence of light chain CDR2 of avian-mouse chimeric antibody (clone No. 165 strain-derived).

SEQ ID NO: 66 is the amino acid sequence of light chain CDR3 of avian-mouse chimeric antibody (clone No. 165 strain-derived).

SEQ ID NO: 67 is the amino acid sequence of heavy chain variable region of avian-mouse chimeric antibody (clone No. 582 strain-derived).

SEQ ID NO: 68 is the amino acid sequence of heavy chain CDR1 of avian-mouse chimeric antibody (clone No. 165 strain-derived).

SEQ ID NO: 69 is the amino acid sequence of heavy chain CDR2 of avian-mouse chimeric antibody (clone No. 165 strain-derived).

SEQ ID NO: 70 is the amino acid sequence of heavy chain CDR3 of avian-mouse chimeric antibody (clone No. 165 strain-derived).

SEQ ID NO: 71 is the amino acid sequence of light chain variable region of avian-mouse chimeric antibody (clone No. 582 strain-derived).

SEQ ID NO: 72 is the amino acid sequence of light chain CDR1 of avian-mouse chimeric antibody (clone No. 582 strain-derived).

SEQ ID NO: 73 is the amino acid sequence of light chain CDR2 of avian-mouse chimeric antibody (clone No. 582 strain-derived).

SEQ ID NO: 74 is the amino acid sequence of light chain CDR3 of avian-mouse chimeric antibody (clone No. 582 strain-derived).

SEQ ID NO: 75 is the amino acid sequence of heavy chain variable region of avian antibody (clone No. 240-40 strain-derived).

SEQ ID NO: 76 is the amino acid sequence of heavy chain CDR1 of avian antibody (clone No. 240-40 strain-derived).

SEQ ID NO: 77 is the amino acid sequence of heavy chain CDR2 of avian antibody (clone No. 240-40 strain-derived).

SEQ ID NO: 78 is the amino acid sequence of heavy chain CDR3 of avian antibody (clone No. 240-40 strain-derived).

SEQ ID NO: 79 is the amino acid sequence of light chain variable region of avian antibody (clone No. 240-40 strain-derived).

SEQ ID NO: 80 is the amino acid sequence of light chain CDR1 of avian antibody (clone No. 240-40 strain-derived).

SEQ ID NO: 81 is the amino acid sequence of light chain CDR2 of avian antibody (clone No. 240-40 strain-derived).

SEQ ID NO: 82 is the amino acid sequence of light chain CDR3 of avian antibody (clone No. 240-40 strain-derived).

SEQ ID NO: 83 is the amino acid sequence of heavy chain variable region of avian antibody (clone No. 255-72 strain-derived).

SEQ ID NO: 84 is the amino acid sequence of heavy chain CDR1 of avian antibody (clone No. 255-72 strain-derived).

SEQ ID NO: 85 is the amino acid sequence of heavy chain CDR2 of avian antibody (clone No. 255-72 strain-derived).

SEQ ID NO: 86 is the amino acid sequence of heavy chain CDR3 of avian antibody (clone No. 255-72 strain-derived).

SEQ ID NO: 87 is the amino acid sequence of light chain variable region of avian antibody (clone No. 255-72 strain-derived).

SEQ ID NO: 88 is the amino acid sequence of light chain CDR1 of avian antibody (clone No. 255-72 strain-derived).

SEQ ID NO: 89 is the amino acid sequence of light chain CDR2 of avian antibody (clone No. 255-72 strain-derived).

SEQ ID NO: 90 is the amino acid sequence of light chain CDR3 of avian antibody (clone No. 255-72 strain-derived).

SEQ ID NO: 91 is the nucleotide sequence of primer-Mγ.

SEQ ID NO: 92 is the nucleotide sequence of primer-Nγ.

SEQ ID NO: 93 is the nucleotide sequence of primer-Oγ.

SEQ ID NO: 94 is the nucleotide sequence of primer-Pγ.

SEQ ID NO: 95 is the nucleotide sequence encoding the amino acid sequence of heavy chain constant region of humanized antibody.

SEQ ID NO: 96 is the nucleotide sequence encoding the amino acid sequence of light chain constant region of humanized antibody.

SEQ ID NO: 97 is the nucleotide sequence encoding the amino acid sequence (SEQ ID NO: 60) of heavy chain CDR1 of avian-mouse chimeric antibody (clone No. 165 strain-derived).

SEQ ID NO: 98 is the nucleotide sequence encoding the amino acid sequence (SEQ ID NO: 61) of heavy chain CDR2 of avian-mouse chimeric antibody (clone No. 165 strain-derived).

SEQ ID NO: 99 is the nucleotide sequence encoding the amino acid sequence (SEQ ID NO: 62) of heavy chain CDR3 of avian-mouse chimeric antibody (clone No. 165 strain-derived).

SEQ ID NO: 100 is the nucleotide sequence encoding the amino acid sequence (SEQ ID NO: 64) of light chain CDR1 of avian-mouse chimeric antibody (clone No. 165 strain-derived).

SEQ ID NO: 101 is the nucleotide sequence encoding the amino acid sequence (SEQ ID NO: 65) of light chain CDR2 of avian-mouse chimeric antibody (clone No. 165 strain-derived).

SEQ ID NO: 102 is the nucleotide sequence encoding the amino acid sequence (SEQ ID NO: 66) of light chain CDR3 of avian-mouse chimeric antibody (clone No. 165 strain-derived).

SEQ ID NO: 103 is the nucleotide sequence encoding the amino acid sequence (SEQ ID NO: 59) of heavy chain variable region of avian-mouse chimeric antibody (clone No. 165 strain-derived).

SEQ ID NO: 104 is the nucleotide sequence encoding the amino acid sequence (SEQ ID NO: 63) of flight chain variable region of avian-mouse chimeric antibody (clone No. 165 strain-derived).

SEQ ID NO: 105 is the nucleotide sequence encoding the amino acid sequence (SEQ ID NO: 68) of heavy chain CDR1 of avian-mouse chimeric antibody (clone No. 582 strain-derived).

SEQ ID NO: 106 is the nucleotide sequence encoding the amino acid sequence (SEQ ID NO: 69) of heavy chain CDR2 of avian-mouse chimeric antibody (clone No. 582 strain-derived).

SEQ ID NO: 107 is the nucleotide sequence encoding the amino acid sequence (SEQ ID NO: 70) of heavy chain CDR3 of avian-mouse chimeric antibody (clone No. 582 strain-derived).

SEQ ID NO: 108 is the nucleotide sequence encoding the amino acid sequence (SEQ ID NO: 72) of light chain CDR1 of avian-mouse chimeric antibody (clone No. 582 strain-derived).

SEQ ID NO: 109 is the nucleotide sequence encoding the amino acid sequence (SEQ ID NO: 73) of light chain CDR2 of avian-mouse chimeric antibody (clone No. 582 strain-derived).

SEQ ID NO: 110 is the nucleotide sequence encoding the amino acid sequence (SEQ ID NO: 74) of light chain CDR3 of avian-mouse chimeric antibody (clone No. 582 strain-derived).

SEQ ID NO: 111 is the nucleotide sequence encoding the amino acid sequence (SEQ ID NO: 67) of heavy chain variable region of avian-mouse chimeric antibody (clone No. 582 strain-derived).

SEQ ID NO: 112 is the nucleotide sequence encoding the amino acid sequence (SEQ ID NO: 71) of light chain variable region of avian-mouse chimeric antibody (clone No. 582 strain-derived).

SEQ ID NO: 113 is the nucleotide sequence encoding the amino acid sequence (SEQ ID NO: 76) of heavy chain CDR1 of avian antibody (clone No. 240-40 strain-derived).

SEQ ID NO: 114 is the nucleotide sequence encoding the amino acid sequence (SEQ ID NO: 77) of heavy chain CDR2 of avian antibody (clone No. 240-40 strain-derived).

SEQ ID NO: 115 is the nucleotide sequence encoding the amino acid sequence (SEQ ID NO: 78) of heavy chain CDR3 of avian antibody (clone No. 240-40 strain-derived).

SEQ ID NO: 116 is the nucleotide sequence encoding the amino acid sequence (SEQ ID NO: 80) of light chain CDR1 of avian antibody (clone No. 240-40 strain-derived).

SEQ ID NO: 117 is the nucleotide sequence encoding the amino acid sequence (SEQ ID NO: 81) of light chain CDR2 of avian antibody (clone No. 240-40 strain-derived).

SEQ ID NO: 118 is the nucleotide sequence encoding the amino acid sequence (SEQ ID NO: 82) of light chain CDR3 of avian antibody (clone No. 240-40 strain-derived).

SEQ ID NO: 119 is the nucleotide sequence encoding the amino acid sequence (SEQ ID NO: 75) of heavy chain variable region of avian antibody (clone No. 240-40 strain-derived).

SEQ ID NO: 120 is the nucleotide sequence encoding the amino acid sequence (SEQ ID NO: 79) of light chain variable region of avian antibody (clone No. 240-40 strain-derived).

SEQ ID NO: 121 is the nucleotide sequence encoding the amino acid sequence (SEQ ID NO: 84) of heavy chain CDR1 of avian antibody (clone No. 255-72 strain-derived).

SEQ ID NO: 122 is the nucleotide sequence encoding the amino acid sequence (SEQ ID NO: 85) of heavy chain CDR2 of avian antibody (clone No. 255-72 strain-derived).

SEQ ID NO: D123 is the nucleotide sequence encoding the amino acid sequence (SEQ ID NO: 86) of heavy chain CDR3 of avian antibody (clone No. 255-72 strain-derived).

SEQ ID NO: 124 is the nucleotide sequence encoding the amino acid sequence (SEQ ID NO: 88) of light chain CDR1 of avian antibody (clone No. 255-72 strain-derived).

SEQ ID NO: 125 is the nucleotide sequence encoding the amino acid sequence (SEQ ID NO: 89) of light chain CDR2 of avian antibody (clone No. 255-72 strain-derived).

SEQ ID NO: 126 is the nucleotide sequence encoding the amino acid sequence (SEQ ID NO: 90) of light chain CDR3 of avian antibody (clone No. 255-72 strain-derived).

SEQ ID NO: 127 is the nucleotide sequence encoding the amino acid sequence (SEQ ID NO: 83) of heavy chain variable region of avian antibody (clone No. 255-72 strain-derived).

SEQ ID NO: 128 is the nucleotide sequence encoding the amino acid sequence (SEQ ID NO: 87) of light chain variable region of avian antibody (clone No. 255-72 strain-derived).

What is claimed is:

1. An anti-semaphorin 3A antibody comprising a heavy chain variable region containing CDR1 having an amino acid sequence shown in SEQ ID NO:68, CDR2 having an amino acid sequence shown in SEQ ID NO:69, and CDR3 having an amino acid sequence shown in SEQ ID NO:70, and a light chain variable region containing CDR1 having an amino acid sequence shown in SEQ ID NO:72, CDR2 having an amino acid sequence shown in SEQ ID NO:73, and CDR3 having an amino acid sequence shown in SEQ ID NO:74
   or antibody fragment thereof containing an antigen binding region thereof.

2. The anti-semaphorin 3A antibody or antibody fragment thereof according to claim 1, wherein the antibody or antibody fragment thereof is a chimeric antibody, a humanized antibody or an antibody fragment thereof.

3. A pharmaceutical composition comprising the anti-semaphorin 3A antibody or antibody fragment thereof according to claim 1.

4. A method for treating Alzheimer's disease, comprising administrating the anti semaphorin 3A antibody or antibody fragment thereof according to claim 1 to a patient with Alzheimer's disease.

5. A method for measuring Sema 3A protein, comprising measuring Sema 3A protein in a sample using immunoassay with the anti-Sema 3A antibody or antibody fragment thereof according to claim 1.

6. A kit for measuring Sema 3A protein, comprising the anti-Sema 3A antibody or antibody fragment thereof according to claim 1.

* * * * *